(12) United States Patent
Morin et al.

(10) Patent No.: US 11,326,212 B2
(45) Date of Patent: *May 10, 2022

(54) BIOMARKERS FOR NON-HODGKIN LYMPHOMAS AND USES THEREOF

(71) Applicant: British Columbia Cancer Agency Branch, Vancouver (CA)

(72) Inventors: Ryan D. Morin, Coquitlam (CA); Marco A. Marra, Vancouver (CA); Andrew J. Mungall, Vancouver (CA); Martin Hirst, Delta (CA); Maria Mendez-Lago, Madrid (ES); Randy D. Gascoyne, Vancouver (CA); Joseph M. Connors, Vancouver (CA)

(73) Assignee: British Columbia Cancer Agency Branch, Vancouver (CA)

( * ) Notice: Subject to any disclaimer, the term of this patent is extended or adjusted under 35 U.S.C. 154(b) by 530 days.

This patent is subject to a terminal disclaimer.

(21) Appl. No.: 16/148,576

(22) Filed: Oct. 1, 2018

(65) Prior Publication Data

US 2019/0153540 A1    May 23, 2019

Related U.S. Application Data

(63) Continuation of application No. 14/282,837, filed on May 20, 2014, now Pat. No. 10,113,199, which is a continuation of application No. 13/805,504, filed as application No. PCT/CA2011/000724 on Jun. 23, 2011, now abandoned.

(60) Provisional application No. 61/420,065, filed on Dec. 6, 2010, provisional application No. 61/357,813, filed on Jun. 23, 2010.

(51) Int. Cl.
| | |
|---|---|
| *C12Q 1/6886* | (2018.01) |
| *G01N 33/574* | (2006.01) |
| *C07K 14/705* | (2006.01) |
| *C40B 30/04* | (2006.01) |

(52) U.S. Cl.
CPC .......... *C12Q 1/6886* (2013.01); *C07K 14/705* (2013.01); *C40B 30/04* (2013.01); *G01N 33/57407* (2013.01); *G01N 33/57426* (2013.01); *C12Q 2600/106* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,716,993 A | 2/1998 | Ozaki et al. | |
| 5,948,803 A | 9/1999 | Maeda et al. | |
| 6,689,583 B1 | 2/2004 | Jenuwein et al. | |
| 7,122,547 B1 | 10/2006 | Huth et al. | |
| 7,252,968 B2 | 8/2007 | Jenuwein et al. | |
| 7,442,685 B2 | 10/2008 | Zhang et al. | |
| 7,563,589 B2 | 7/2009 | Zhang et al. | |
| 7,745,391 B2 | 6/2010 | Mintz et al. | |
| 7,923,219 B2 | 4/2011 | Wang et al. | |
| 8,410,088 B2 | 4/2013 | Kuntz et al. | |
| 8,536,179 B2 | 9/2013 | Miller et al. | |
| 8,691,507 B2 | 4/2014 | Copeland et al. | |
| 8,765,732 B2 | 7/2014 | Kuntz et al. | |
| 8,895,245 B2 | 11/2014 | Copeland et al. | |
| 9,045,801 B2 | 6/2015 | Morin et al. | |
| 9,090,562 B2 | 7/2015 | Kuntz et al. | |
| 9,175,331 B2 | 11/2015 | Kuntz et al. | |
| 9,333,217 B2 | 5/2016 | Copeland et al. | |
| 9,334,527 B2 | 5/2016 | Kuntz et al. | |
| 9,522,152 B2 | 12/2016 | Kuntz et al. | |
| 9,549,931 B2 | 1/2017 | Kuntz et al. | |
| 9,688,665 B2 | 6/2017 | Knutson et al. | |
| 9,855,275 B2 | 1/2018 | Kuntz et al. | |
| 9,949,999 B2 | 4/2018 | Copeland et al. | |
| 10,098,888 B2 | 10/2018 | Kuntz et al. | |
| 10,113,199 B2 | 10/2018 | Morin et al. | |
| 10,301,290 B2 | 5/2019 | Keilhack et al. | |
| 2002/0183324 A1 | 12/2002 | Jacobson et al. | |
| 2003/0093819 A1 | 5/2003 | D'Andrea et al. | |
| 2004/0082619 A1 | 4/2004 | Tada et al. | |
| 2005/0059682 A1 | 3/2005 | Rubinfeld | |
| 2005/0089880 A1 | 4/2005 | Jenuwein et al. | |
| 2005/0266473 A1 | 12/2005 | Zbang et al. | |
| 2007/0269370 A1 | 11/2007 | Davis et al. | |
| 2008/0182844 A1 | 7/2008 | Bjergarde et al. | |

(Continued)

FOREIGN PATENT DOCUMENTS

| | | |
|---|---|---|
| CN | 1683526 A | 10/2005 |
| CN | 101365806 A | 2/2009 |

(Continued)

OTHER PUBLICATIONS

Bödör, C. et al. (Oct. 31, 2013) "EZH2 mutation are frequent and represent an early event in follicular lymphoma" *Blood*, 122(18):3165-3168.

(Continued)

*Primary Examiner* — Nancy J Leith

(74) *Attorney, Agent, or Firm* — Cooley LLP; Heidi A. Erlacher; Robert E. Powers

(57) ABSTRACT

The disclosure provides a method of identifying a subject as having B-cell non-Hodgkin lymphoma (NHL) such as testing a sample from a subject for a mutation in one or more biomarkers. Also described are methods for classifying or monitoring a subject having, or suspected of having, B-cell non-Hodgkin lymphoma comprising testing the sample for a mutation in one or more biomarkers.

12 Claims, 7 Drawing Sheets

Specification includes a Sequence Listing.

(56) References Cited

U.S. PATENT DOCUMENTS

| | | |
|---|---|---|
| 2008/0222741 A1 | 9/2008 | Chinnaiyan |
| 2008/0269289 A1 | 10/2008 | Frank et al. |
| 2008/0312292 A1 | 12/2008 | Yasui et al. |
| 2009/0012031 A1 | 1/2009 | Chinnaiyan et al. |
| 2009/0012175 A1 | 1/2009 | Bacopoulos et al. |
| 2009/0061443 A1 | 3/2009 | Zhang et al. |
| 2009/0203057 A1 | 8/2009 | Zhang et al. |
| 2010/0035912 A1 | 2/2010 | Debnath et al. |
| 2010/0113415 A1 | 5/2010 | Rajapakse et al. |
| 2011/0021362 A1 | 1/2011 | Trojer et al. |
| 2013/0102477 A1 | 4/2013 | Morin et al. |
| 2013/0195843 A1 | 8/2013 | Morin et al. |
| 2014/0275081 A1 | 9/2014 | Kuntz et al. |
| 2014/0378470 A1 | 12/2014 | Creasy et al. |
| 2015/0141362 A1 | 5/2015 | Copeland et al. |
| 2015/0368229 A1 | 12/2015 | Albrecht et al. |
| 2017/0065600 A1 | 3/2017 | Kuntz et al. |
| 2017/0065628 A1 | 3/2017 | Copeland et al. |
| 2018/0271892 A1 | 9/2018 | Copeland et al. |
| 2018/0280402 A1 | 10/2018 | Keilhack et al. |
| 2018/0311251 A1 | 11/2018 | Keilhack et al. |
| 2019/0255060 A1 | 8/2019 | Keilhack et al. |
| 2020/0016162 A1 | 1/2020 | Kuntz et al. |
| 2020/0022987 A1 | 1/2020 | Keilhack et al. |
| 2020/0323866 A1 | 10/2020 | Keilhack et al. |
| 2020/0397812 A1 | 12/2020 | Copeland et al. |
| 2021/0052595 A1 | 2/2021 | Blakemore et al. |
| 2021/0239710 A1 | 8/2021 | Plescia |

FOREIGN PATENT DOCUMENTS

| | | |
|---|---|---|
| EP | 1357111 A1 | 10/2003 |
| EP | 2914296 B1 | 5/2018 |
| JP | 7-33729 A | 2/1995 |
| KR | 20070029617 A | 3/2007 |
| WO | WO 1996/040100 A1 | 12/1996 |
| WO | WO 2000/018725 A1 | 4/2000 |
| WO | WO 2003/079788 A2 | 10/2003 |
| WO | WO 2005/018578 A2 | 3/2005 |
| WO | WO 2005/034845 A2 | 4/2005 |
| WO | WO 2006/116713 A1 | 11/2006 |
| WO | WO 2007/045462 A2 | 4/2007 |
| WO | WO 2007/050347 A1 | 5/2007 |
| WO | WO 2007/070818 A1 | 6/2007 |
| WO | WO 2007/072225 A2 | 6/2007 |
| WO | WO 2007/136592 A2 | 11/2007 |
| WO | WO 2008/073138 A2 | 6/2008 |
| WO | WO 2008/103277 A2 | 8/2008 |
| WO | WO 2008/104077 A1 | 9/2008 |
| WO | WO 2008/108825 A2 | 9/2008 |
| WO | WO 2008/113006 A1 | 9/2008 |
| WO | WO 2009/058298 A1 | 5/2009 |
| WO | WO 2009/077766 A1 | 6/2009 |
| WO | WO 2009/124137 A2 | 10/2009 |
| WO | WO 2010/018328 A1 | 2/2010 |
| WO | WO 2010/111653 A2 | 9/2010 |
| WO | WO 2011/082044 A1 | 7/2011 |
| WO | WO 2011/140324 A1 | 11/2011 |
| WO | WO 2011/140325 A1 | 11/2011 |
| WO | WO 2011/160206 A1 | 12/2011 |
| WO | WO 2012/005805 A1 | 1/2012 |
| WO | WO 2012/034132 A2 | 3/2012 |
| WO | WO 2012/068589 A2 | 5/2012 |
| WO | WO 2012/075080 A1 | 6/2012 |
| WO | WO 2012/075500 A2 | 6/2012 |
| WO | WO 2012/118812 A2 | 9/2012 |
| WO | WO 2012/142513 A1 | 10/2012 |
| WO | WO 2013/049770 A2 | 4/2013 |
| WO | WO 2013/120104 A2 | 8/2013 |
| WO | WO 2013/138361 A1 | 9/2013 |
| WO | WO 2013/155464 A1 | 10/2013 |
| WO | WO 2014/124418 A1 | 8/2014 |
| WO | WO 2017/100362 A2 | 6/2017 |
| WO | WO 2018/231973 A1 | 12/2018 |

OTHER PUBLICATIONS

Chase, A. et al. (2011) "Aberrations EZH2 in cancer" Clin Cancer Res, 17(9):2613-2618.

Knutson, S.K. et al. (May 7, 2013) "Durable tumor regression in genetically altered malignant rhabdoid tumors by inhibition of methyltransferase EZH2" PNAS, 110(19):7922-7927.

Vodolazhsky, D.I. and Timoshkina, N.N. (2009) "Molecular-genetic markers of a prostate cancer" Bulletin of the Southern Science Center (Вестник Южного научного центра. . Vestnik Yuzhnogo nauchnogo tsentra), 5(1):36-52 (Russian; English abstract on p. 52).

"Personalised Medicine Briefsheet" Cancer Research UK, Oct. 2010 [online]. Retrieved from www.cancerresearchuk.org, 2 pages.

"Sample overview for 1451273. GRCh38 COSMIC v84" [online]. Retrieved from: http://cancer.sanger.ac.uk/cosmic/sample/overview?id=1451273, accessed Mar. 15, 2018, 5 pages.

Barski et al. (2007) "High-Resolution Profiling of Histone Methylations in the Human Genome" Cell, 129(4):823-837.

Beisel et al. (2002) "Histone Methylation by the Drosophila Epigenetic Transcriptional Regulator Ash1" Nature. 419:857-862.

Bernstein et al. (2006) "A Bivalent Chromatin Structure Marks Key Developmental Genes in Embryonic Stem Cells" Cell. 125(2):315-326.

Bhanot, G. et al. (2005) "Robust diagnosis of non-Hodgkin lymphoma phenotypes validated on gene expression data from different laboratories" Genome Informatics, 16(1):233-244.

Bracken et al. (2003) "EZH2 is Downstream of the pRB-E2F Pathway, Essential for Proliferation and Amplified in Cancer" EMBO J. 22(20):5323-5335.

Braña et al. (1982) "Reaction of N-(2-Pyridylmethyl)-3,5-dimethylbenzamide and N-(3-Pyridylmethyl)-3,5-dimethylbenzamide N-Oxides With Acetic Anhydride." J. Het. Chem. 19(6):1297-1300.

Cahn, R.S. (1964) "An Introduction to the Sequence Rule" J Chem Educ, 41(3):116-125.

Cahn, R.S. and C.K. Ingold (1951) "Specification of Configuration about Quadricovalent Asymmetric Atoms" J Chem Soc, p. 612-622.

Cahn, R.S. et al. (1956) "The Specification of Asymmetric Configuration in Organic Chemistry" Experientia, 12:81-94.

Cahn, R.S. et al. (1966) "Specification of Molecular Chirality" Agnew Chem Inter Edit, 5(4):385-415.

Cao et al. (2002) "Role of Histone H3 Lysine 27 Methylation in Polycomb-Group Silencing" Science. 298:1039-1043.

Cao et al. (2004) "SUZ12 is Required for Both the Histone Methyltransferase Activity and the Silencing Function of the EED-EZH2 Complex" Mol. Cell. 15(1):57-67.

Cao et al. (2008) "Role of hPHF1 in H3K27 Methylation and Hox Gene Silencing" Mol. Cell. Biol. 28(5):1862-1872.

Chang, C. et al. (Feb. 2010) "Non-Hodgkin lymphoma (NHL) subtypes defined by common translations: utility of fluorescence in situ hybridization (FISH) in a case-control study" Leukemia Research, 34(2):190-195. NIH Public Access Author Manuscript, 16 pages.

Chen, H. et al. (1996) "Cloning of a Human Homolog of the Drosophila Enhancer of zeste Gene (EZH2) That Maps to Chromosome 21q22.2" Genomics, 38:30-37.

clinicaltrials.gov Archive (Nov. 10, 2016) "An Open-Label, Multicenter, Phase 1/2 Study of E7438 (EZH2 Histone Methyl Transferase [HMT] Inhibitor) as a Single Agent in Subjects With Advanced Solid Tumors or With B Cell Lymphomas" Clinical Trials Identifier: NCT01897571 [online]. Retrieved from: https://clinicaltrials.gov/archive/ NCT01897571/?V_17=View#StudyPageTop; retrieved on Oct. 2, 2019, 11 pages.

Compagno, M. et al. (Jun. 2009) "Mutations of multiple genes cause deregulation of NF-kappas in diffuse large B-cell lymphoma" Nature, 459:717-721, including Supplementary Information, 1 page.

Copeland et al. (2010) "Targeting Epigenetic Enzymes for Drug Discovery" Curr. Opin. Chem. Biol. 14(4):505-510.

Copeland, R.A. et al. (Sep. 2009) "Protein methyltransferases as a target class for drug discovery" Nature Reviews/DrugDiscovery, 8:724-732.

Cui et al. (2009) "Chromatin Signatures in Multipotent Human Hematopoietic Stem Cells Indicate the Fate of Bivalent Genes During Differentiation" Cell Stem Cell, 4(1):80-93.

(56) References Cited

OTHER PUBLICATIONS

Czermin et al. (2002) "*Drosphila* Enhancer of Zeste/ESC Complexes Have A Histone H3 Methyltransferase Activity That Marks Chromosomal Polycomb Sites" *Cell.* 111(2):185-196.
Da Cunha Santos, G. et al. (Oct. 25, 2010) "Targeted use of fluorescence in situ hybridization (FISH) in cytospin preparations. Results of 298 fine needle aspirates of B-cell non-Hodgkin lymphoma" *Cancer Cytopathology*, 118(5):250-258.
Dalgliesh, G.L. et al. (Jan. 21, 2010) "Systematic sequencing of renal carcinoma reveals inactivation of histone modifying genes" *Nature*, 463:360-363.
Davis, R.E. et al. (Jan. 7, 2010) "Chronic active B-cell-receptor signalling in diffuse large B-cell lymphoma" *Nature*, 463:88-92, including Supplemental Information, 2 pages.
De Paepe, P. et al. (2007) "Diffuse large b-cell lymphoma: a heterogenous group of non-Hodgkin lymphomas comprising several distinct clinicopathological entities" *Leukemia*, 21:37-43.
Declaration of Mr. Martin Brandt, dated Mar. 15, 2018. Submitted in Opposition to European Patent No. EP2614369, Application No. 11824247.8 on Mar. 15, 2018; 3 pages.
Erhardt et al. (2003) "Consequence of the Depletion of Zygotic and Embryonic Enhancer of Zeste 2 During Preimplantation Mouse Development" *Development*, 130:4235-4248.
Ernst, T. et al. (Aug. 2010) "Inactivating mutations of the histone methyltransferase gene EZH2 in myeloid disorders" *Nature Genetics*, vol. 42, pp. 722-726.
Fiskus et al. (2008) "Combined Epigenetic Therapy with the Novel Histone Methyl Transferase EZH2 Inhibitor 3-Deazaneplanocin and Histone Deacetylase Inhibitor Panobinostat Exerts Synergistic Activity against Human Mantle Cell Lymphoma Cells" *Blood* (ASH Annual Meeting Abstracts), 112: Abstract 3622.
Fiskus et al. (2009) "Combined epigenetic therapy with the histone methyltransferase EZH2 inhibitor 3-deazaneplanocin A and the histone deacetylase inhibitor panobinostat against human AML cells" *Blood*, 114(13):2733-2743.
Francis et al. (2001) "Mechanisms of Transcriptional Memory" *Nat Rev Mol Cell Biol*, 2:409-421.
Futreal, P.A. et al. (Mar. 2004) "A census of human cancer genes" *Nat Rev Cancer*, 4:177-183.
GENBANK Accession No. AF232001.1 (Jul. 14, 2016) "*Homo sapiens* MLL protein (MLL) mRNA, partial cds" National Center for Biotechnology Information (NCBI) [online]. Retrieved from: www.ncbi.nlm.nih.gov; retrieved on Mar. 28, 2019, 2 pages.
GENBANK Accession No. CAB02546 (Apr. 18, 2005) "histone H3 [*Homo sapiens*]" National Center for Biotechnology Information (NCBI) [online]. Retrieved from: www.ncbi.nlm.nih.gov; retrieved on Jul. 23, 2012, 2 pages.
GENBANK Accession No. NM_000038.5 (Nov. 17, 2018) "*Homo sapiens* APC, WNT signaling pathway regulator (APC), transcript variant 3, mRNA" National Center for Biotechnology Information (NCBI) [online], Retrieved from: www.ncbi.nlm.nih.gov; retrieved on Mar. 28, 2019, 13 pages.
GENBANK Accession No. NM_000044.3 (Jul. 9, 2016) "*Homo sapiens* androgen receptor (AR), transcript variant 1, mRNA" National Center for Biotechnology Information (NCBI) [online]. Retrieved from: www.ncbi.nlm.nih.gov; retrieved on Mar. 28, 2019, 10 pages.
GENBANK Accession No. NM_000051.3 (Mar. 24, 2019) "*Homo sapiens* ATM serine/threonine kinase (ATM), transcript variant 2, mRNA" National Center for Biotechnology Information (NCBI) [online]. Retrieved from: www.ncbi.nlm.nih.gov; retrieved on Mar. 28, 2019, 12 pages.
GENBANK Accession No. NM_000057.3 (Oct. 20, 2019) "*Homo sapiens* BLM RecQ like helicase (BLM), transcript variant 1, mRNA" National Center for Biotechnology Information (NCBI) [online]. Retrieved from: www.ncbi.nlm.nih.gov; retrieved on Mar. 28, 2019, 9 pages.
GENBANK Accession No. NM_000059.3 (Mar. 19, 2019) "*Homo sapiens* BRCA2 DNA repair associated (BRCA2), mRNA" National Center for Biotechnology Information (NCBI) [online]. Retrieved from: www.ncbi.nlm.nih.gov; retrieved on Mar. 28, 2019, 11 pages.
GENBANK Accession No. NM_000075.3 (Nov. 4, 2018) "*Homo sapiens* cyclin dependent kinase 4 (CDK4), mRNA" National Center for Biotechnology Information (NCBI) [online]. Retrieved from: www.ncbi.nlm.nih.gov; retrieved on Mar. 28, 2019, 5 pages.
GENBANK Accession No. NM_000123.3 (Feb. 24, 2019) "*Homo sapiens* ERCC excision repair 5, endonuclease (ERCC5), mRNA" National Center for Biotechnology Information (NCBI) [online]. Retrieved from: www.ncbi.nlm.nih.gov; retrieved on Mar. 28, 2019, 6 pages.
GENBANK Accession No. NM_000127.2 (Feb. 16, 2019) "*Homo sapiens* exostosin glycosyltransferase 1 (EXT1), mRNA" National Center for Biotechnology Information (NCBI) [online]. Retrieved from: www.ncbi.nlm.nih.gov; retrieved on Mar. 28, 2019, 6 pages.
GENBANK Accession No. NM_000141.4 (Feb. 21, 2019) "*Homo sapiens* fibroblast growth factor receptor 2 (FGFR2), transcript variant 1, mRNA" National Center for Biotechnology Information (NCBI) [online], Retrieved from: www.ncbi.nlm.nih.gov; retrieved on Mar. 28, 2019, 9 pages.
GENBANK Accession No. NM_000143.3 (Feb. 22, 2019) "*Homo sapiens* fumarate hydratase (FH), mRNA" National Center for Biotechnology Information (NCBI) [online]. Retrieved from: www.ncbi.nlm.nih.gov; retrieved on Mar. 28, 2019, 6 pages.
GENBANK Accession No. NM_000179.2 (Mar. 19, 2019) "*Homo sapiens* mutS homolog 6 (MSH6), transcript variant 1, mRNA" National Center for Biotechnology Information (NCBI) [online]. Retrieved from: www.ncbi.nlm.nih.gov; retrieved on Mar. 28, 2019, 7 pages.
GENBANK Accession No. NM_000215.3 (Mar. 12, 2019) "*Homo sapiens* Janus kinase 3 (JAK3), mRNA" National Center for Biotechnology Information (NCBI) [online]. Retrieved from: www.ncbi.nlm.nih.gov; retrieved on Mar. 28, 2019, 7 pages.
GENBANK Accession No. NM_000245.3 (Mar. 12, 2019) "*Homo sapiens* MET proto-oncogene, receptor tyrosine kinase (MET), transcript variant 2, mRNA" National Center for Biotechnology Information (NCBI) [online]. Retrieved from: www.ncbi.nlm.nih.gov; retrieved on Mar. 28, 2019; 6 pages.
GENBANK Accession No. NM_000249.3 (Mar. 25, 2019) "*Homo sapiens* mutL homolog 1 (MLH1), transcript variant 1, mRNA" National Center for Biotechnology Information (NCBI) [online]. Retrieved from: www.ncbi.nlm.nih.gov; retrieved on Mar. 28, 2019, 5 pages.
GENBANK Accession No. NM_000251.2 (Mar. 19, 2019) "*Homo sapiens* mutS homolog 2 (MSH2), transcript variant 1, mRNA" National Center for Biotechnology Information (NCBI) [online]. Retrieved from: www.ncbi.nlm.nih.gov; retrieved on Mar. 28, 2019, 5 pages.
GENBANK Accession No. NM_000264.3 (Jun. 26, 2017) "*Homo sapiens* patched 1 (PTCH1), transcript variant 1b, mRNA" National Center for Biotechnology Information (NCBI) [online]. Retrieved from: www.ncbi.nlm.nih.gov; retrieved on Mar. 28, 2019, 6 pages.
GENBANK Accession No. NM_000314.6 (Nov. 18, 2018) "*Homo sapiens* phosphatase and tensin homolog (PTEN), transcript variant 1, mRNA" National Center for Biotechnology Information (NCBI) [online], Retrieved from: www.ncbi.nlm.nih.gov; retrieved on Mar. 28, 2019, 9 pages.
GENBANK Accession No. NM_000321.2 (Feb. 17, 2019) "*Homo sapiens* RB transcriptional corepressor 1 (RB1), mRNA" National Center for Biotechnology Information (NCBI) [online]. Retrieved from: www.ncbi.nlm.nih.gov; retrieved on Mar. 28, 2019, 9 pages.
GENBANK Accession No. NM_000369.2 (Feb. 10, 2019) "*Homo sapiens* thyroid stimulating hormone receptor (TSHR), transcript variant 1, mRNA" National Center for Biotechnology Information (NCBI) [online], Retrieved from: www.ncbi.nlm.nih.gov; retrieved on Mar. 28, 2019, 7 pages.
GENBANK Accession No. NM_000377.2 (Mar. 12, 2019) "*Homo sapiens* WASP actin nucleation promoting factor (WAS), mRNA" National Center for Biotechnology Information (NCBI) [online]. Retrieved from: www.ncbi.nlm.nih.gov; retrieved on Mar. 28, 2019, 5 pages.
GENBANK Accession No. NM_000378.4 (Dec. 29, 2017) "*Homo sapiens* Wilms tumor 1 (WT1), transcript variant A, mRNA"

(56) References Cited

OTHER PUBLICATIONS

National Center for Biotechnology Information (NCBI) [online]. Retrieved from: www.ncbi.nlm.nih.gov; retrieved on Mar. 28, 2019, 6 pages.
GENBANK Accession No. NM_000380.3 (Mar. 12, 2019) "*Homo sapiens* XPA, DNA damage recognition and repair factor (XPA), transcript variant 1, mRNA" National Center for Biotechnology Information (NCBI) [online]. Retrieved from: www.ncbi.nlm.nih.gov; retrieved on Mar. 28, 2019, 4 pages.
GENBANK Accession No. NM_000435.2 (Nov. 4, 2018) "*Homo sapiens* notch 3 (NOTCH3), mRNA" National Center for Biotechnology Information (NCBI) [online]. Retrieved from: www.ncbi.nlm.nih.gov; retrieved on Mar. 28, 2019, 8 pages.
GENBANK Accession No. NM_000455.4 (Feb. 17, 2019) "*Homo sapiens* serine/threonine kinase 11 (STK11), mRNA" National Center for Biotechnology Information (NCBI) [online]. Retrieved from: www.ncbi.nlm.nih.gov; retrieved on Mar. 28, 2019; 6 pages.
GENBANK Accession No. NM_000489.4 (Apr. 9, 2018) "*Homo sapiens* ATRX, chromatin remodeler (ATRX), transcript variant 1, mRNA" National Center for Biotechnology Information (NCBI) [online]. Retrieved from: www.ncbi.nlm.nih.gov; retrieved on Mar. 28, 2019, 16 pages.
GENBANK Accession No. NM_000535.6 (Nov. 18, 2018) "*Homo sapiens* PMS1 homolog 2, mismatch repair system component (PMS2), transcript variant 1, mRNA" National Center for Biotechnology Information (NCBI) [online]. Retrieved from: www.ncbi.nlm.nih.gov; retrieved on Mar. 28, 2019, 5 pages.
GENBANK Accession No. NM_000545.6 (Mar. 4, 2019) "*Homo sapiens* HNF1 homeobox A (HNF1A), transcript variant 2, mRNA" National Center for Biotechnology Information (NCBI) [online]. Retrieved from: www.ncbi.nlm.nih.gov; retrieved on Mar. 28, 2019, 6 pages.
GENBANK Accession No. NM_000546.5 (Feb. 23, 2019) "*Homo sapiens* tumor protein p53 (TP53), transcript variant 1, mRNA" National Center for Biotechnology Information (NCBI) [online]. Retrieved from: www.ncbi.nlm.nih.gov; retrieved on Mar. 28, 2019, 10 pages.
GENBANK Accession No. NM_000551.3 (Mar. 19, 2019) "*Homo sapiens* von Hippel-Lindau tumor suppressor (VHL), transcript variant 1, mRNA" National Center for Biotechnology Information (NCBI) [online], Retrieved from: www.ncbi.nlm.nih.gov; retrieved on Mar. 28, 2019, 6 pages.
GENBANK Accession No. NM_000553.4 (Jul. 31, 2017) "*Homo sapiens* Werner syndrome RecQ like helicase (WRN), mRNA" National Center for Biotechnology Information (NCBI) [online]. Retrieved from: www.ncbi.nlm.nih.gov; retrieved on Mar. 28, 2019, 6 pages.
GENBANK Accession No. NM_000633.2 (Mar. 25, 2019) "*Homo sapiens* BCL2 apoptosis regulator (BCL2), transcript variant alpha, mRNA" National Center for Biotechnology Information (NCBI) [online]. Retrieved from: www.ncbi.nlm.nih.gov; retrieved on Mar. 28, 2019, 6 pages.
GENBANK Accession No. NM_000876.3 (Mar. 25, 2019) "*Homo sapiens* insulin like growth factor 2 receptor (IGF2R), mRNA" National Center for Biotechnology Information (NCBI) [online]. Retrieved from: www.ncbi.nlm.nih.gov; retrieved on Mar. 28, 2019, 14 pages.
GENBANK Accession No. NM_001007468.2 (Mar. 25, 2019) "*Homo sapiens* SWI/SNF related, matrix associated, actin dependent regulator of chomatin, subfamily b, member 1 (SMARCB1), transcript variant 2, mRNA" National Center for Biotechnology Information (NCBI) [online]. Retrieved from: www.ncbi.nlm.nih.gov; retrieved on Mar. 28, 2019; 4 pages.
GENBANK Accession No. NM_001007792.1 (Mar. 4, 2019) "*Homo sapiens* neurotrophic receptor tyrosine kinase 1 (NTRK1), transcript variant 3, mRNA" National Center for Biotechnology Information (NCBI) [online]. Retrieved from: www.ncbi.nlm.nih.gov; retrieved on Mar. 28, 2019, 5 pages.
GENBANK Accession No. NM_001014431.1 (Mar. 25, 2019) "*Homo sapiens* AKT serine/threonine kinase 1 (AKT1), transcript variant 3, mRNA" National Center for Biotechnology Information (NCBI) [online], Retrieved from: www.ncbi.nlm.nih.gov/nuccore; retrieved on Mar. 28, 2019; 7 pages.
GENBANK Accession No. NM_001014796.1 (Mar. 25, 2019) "*Homo sapiens* discoidin domain receptor tyrosine kinase 2 (DDR2), transcript variant 1" National Center for Biotechnology Information (NCBI) [online]. Retrieved from: www.ncbi.nlm.nih.gov; retrieved on Mar. 28, 2019, 7 pages.
GENBANK Accession No. NM_001024688.2 (Mar. 24, 2019) "*Homo sapiens* nibrin (NBN), transcript variant 2, mRNA" National Center for Biotechnology Information (NCBI) [online]. Retrieved from: www.ncbi.nlm.nih.gov; retrieved on Mar. 28, 2019, 5 pages.
GENBANK Accession No. NM_001024847.2 (Feb. 17, 2019) "*Homo sapiens* transforming growth factor beta receptor 2 (TGFBR2), transcript variant 1, mRNA" National Center for Biotechnology Information (NCBI) [online]. Retrieved from: www.ncbi.nlm.nih.gov; retrieved on Mar. 28, 2019, 5 pages.
GENBANK Accession No. NM_001033081.2 (Jun. 24, 2018) "*Homo sapiens* MYCL proto-oncogene, bHLH transcription factor (MYCL), transcript variant 1, mRNA" National Center for Biotechnology Information (NCBI) [online]. Retrieved from: www.ncbi.nlm.nih.gov; retrieved on Mar. 28, 2019, 4 pages.
GENBANK Accession No. NM_001042355.1 (Feb. 17, 2019) "*Homo sapiens* CYLD lysine 63 deubiquitinase (CYLD), transcript variant 2, mRNA" National Center for Biotechnology Information (NCBI) [online], Retrieved from: www.ncbi.nlm.nih.gov; retrieved on Mar. 28, 2019, 7 pages.
GENBANK Accession No. NM_001042492.2 (Feb. 22, 20192) "*Homo sapiens* neurofibromin 1 (NF1), transcript variant 1, mRNA" National Center for Biotechnology Information (NCBI) [online]. Retrieved from: www.ncbi.nlm.nih.gov; retrieved on Mar. 28, 2019, 13 pages.
GENBANK Accession No. NM_001042594.1 (Mar. 12, 2019) "*Homo sapiens* protection of telomeres 1 (POT1), transcript variant 4, mRNA" National Center for Biotechnology Information (NCBI) [online], Retrieved from: www.ncbi.nlm.nih.gov; retrieved on Mar. 28, 2019, 5 pages.
GENBANK Accession No. NM_001048171.1 (Feb. 17, 2019) "*Homo sapiens* mutY DNA glycosylase (MUTYH), transcript variant alpha3, mRNA" National Center for Biotechnology Information (NCBI) [online], Retrieved from: www.ncbi.nlm.nih.gov; retrieved on Mar. 28, 2019, 4 pages.
GENBANK Accession No. NM_001079668.2 (Mar. 12, 2019) "*Homo sapiens* NK2 homeobox 1 (NKX2-1), transcript variant 1, mRNA" National Center for Biotechnology Information (NCBI) [online]. Retrieved from: www.ncbi.nlm.nih.gov; retrieved on Mar. 28, 2019, 4 pages.
GENBANK Accession No. NM_001079846.1 (Mar. 4, 2019) "*Homo sapiens* CREB binding protein (CREBBP), transcript variant 2, mRNA" National Center for Biotechnology Information (NCBI) [online], Retrieved from: www.ncbi.nlm.nih.gov; retrieved on Mar. 28, 2019, 11 pages.
GENBANK Accession No. NM_001093772.1 (Mar. 25, 2019) "*Homo sapiens* KIT proto-oncogene, receptor tyrosine kinase (KIT), transcript variant 2, mRNA" National Center for Biotechnology Information (NCBI) [online]. Retrieved from: www.ncbi.nlm.nih.gov; retrieved on Mar. 28, 2019, 9 pages.
GENBANK Accession No. NM_001098209.1 (Mar. 19, 2019) "*Homo sapiens* catenin beta 1 (CTNNB1), transcript variant 2, mRNA" National Center for Biotechnology Information (NCBI) [online]. Retrieved from: www.ncbi.nlm.nih.gov; retrieved on Mar. 28, 2019, 8 pages.
GENBANK Accession No. NM_001105.4 (Mar. 25, 2019) "*Homo sapiens* activin A receptor type 1 (ACVR1), transcript variant 1, mRNA" National Center for Biotechnology Information (NCBI) [online]. Retrieved from: www.ncbi.nlm.nih.gov; retrieved on Mar. 28, 2019, 5 pages.
GENBANK Accession No. NM_001114636.1 (Feb. 20, 2019) "*Homo sapiens* FA complementation group L (FANCL), transcript variant 1, mRNA" National Center for Biotechnology Information (NCBI) [online], Retrieved from: www.ncbi.nlm.nih.gov; retrieved on Mar. 28, 2019, 4 pages.

(56) References Cited

OTHER PUBLICATIONS

GENBANK Accession No. NM_001122607.1 (Mar. 19, 2019) "*Homo sapiens* runt related transcription factor 1 (RUNX1), transcript variant 3, mRNA" National Center for Biotechnology Information (NCBI) [online], Retrieved from: www.ncbi.nlm.nih.gov; retrieved on Mar. 28, 2019, 4 pages.
GENBANK Accession No. NM_001130442.2 (Mar. 19, 2019) "*Homo sapiens* HRas proto-oncogene, GTPase (HRAS), transcript variant 3, mRNA" National Center for Biotechnology Information (NCBI) [online], Retrieved from: www.ncbi.nlm.nih.gov; retrieved on Mar. 28, 2019, 5 pages.
GENBANK Accession No. NM_001130867.1 (Feb. 18, 2019) "*Homo sapiens* ERCC excision repair 2, TFIIH core complex helicase subunit (ERCC2), transcript variant 2, mRNA" National Center for Biotechnology Information (NCBI) [online]. Retrieved from: www.ncbi.nlm.nih.gov; retrieved on Mar. 28, 2019, 4 pages.
GENBANK Accession No. NM_001135937.2 (Mar. 19, 2019) "*Homo sapiens* SMAD family member 2 (SMAD2), transcript variant 3, mRNA" National Center for Biotechnology Information (NCBI) [online], Retrieved from: www.ncbi.nlm.nih.gov; retrieved on Mar. 28, 2019, 7 pages.
GENBANK Accession No. NM_001141969.1 (Oct. 20, 2018) "*Homo sapiens* death domain associated protein (DAXX), transcript variant 1, mRNA" National Center for Biotechnology Information (NCBI) [online], Retrieved from: www.ncbi.nlm.nih.gov; retrieved on Mar. 28, 2019, 7 pages.
GENBANK Accession No. NM_001145104.1 (Mar. 24, 2019) "*Homo sapiens* SMAD family member 3 (SMAD3), transcript variant 4, mRNA" National Center for Biotechnology Information (NCBI) [online], Retrieved from: www.ncbi.nlm.nih.gov; retrieved on Mar. 28, 2019, 5 pages.
GENBANK Accession No. NM_001145306.1 (Feb. 20, 2019) "*Homo sapiens* cyclin dependent kinase 6 (CDK6), transcript variant 2, mRNA" National Center for Biotechnology Information (NCBI) [online], Retrieved from: www.ncbi.nlm.nih.gov; retrieved on Mar. 28, 2019, 8 pages.
GENBANK Accession No. NM_001145337.2 (Jun. 3, 2018) "*Homo sapiens* MDM2 proto-oncogene (MDM2), transcript variant 3, mRNA" National Center for Biotechnology Information (NCBI) [online]. Retrieved from: www.ncbi.nlm.nih.gov; retrieved on Mar. 28, 2019, 6 pages.
GENBANK Accession No. NM_001145662.1 (Mar. 4, 2019) "*Homo sapiens* GATA binding protein 2 (GATA2), transcript variant 3, mRNA" National Center for Biotechnology Information (NCBI) [online], Retrieved from: www.ncbi.nlm.nih.gov; retrieved on Mar. 28, 2019, 4 pages.
GENBANK Accession No. NM_001162427.1 (Feb. 23, 2019) "*Homo sapiens* TSC complex subunit 1 (TSC1), transcript variant 4, mRNA" National Center for Biotechnology Information (NCBI) [online]. Retrieved from: www.ncbi.nlm.nih.gov; retrieved on Mar. 28, 2019, 6 pages.
GENBANK Accession No. NM_001163147.1 (Jul. 15, 2018) "*Homo sapiens* ETS variant 1 (ETV1), transcript variant 2, mRNA" National Center for Biotechnology Information (NCBI) [online]. Retrieved from: www.ncbi.nlm.nih.gov; retrieved on Mar. 28, 2019, 6 pages.
GENBANK Accession No. NM_001163213.1 (Feb. 23, 2019) "*Homo sapiens* fibroblast growth factor 3 (FGFR3), transcript variant 3, mRNA" National Center for Biotechnology Information (NCBI) [online], Retrieved from: www.ncbi.nlm.nih.gov; retrieved on Mar. 28, 2019, 6 pages.
GENBANK Accession No. NM_001163287.1 (Mar. 4, 2019) "*Homo sapiens* EWS RNA binding protein 1 (EWSR1), transcript variant 5, mRNA" National Center for Biotechnology Information (NCBI) [online], Retrieved from: www.ncbi.nlm.nih.gov; retrieved on Mar. 28, 2019, 5 pages.
GENBANK Accession No. NM_001164619.1 (Feb. 23, 2019) "*Homo sapiens* glypican (GPC3), transcript variant 4, mRNA" National Center for Biotechnology Information (NCBI) [online]. Retrieved from: www.ncbi.nlm.nih.gov; retrieved on Mar. 28, 2019, 5 pages.
GENBANK Accession No. NM_001166049.1 (Feb. 23, 2019) "*Homo sapiens* ERCC excision repair 1, endonuclease non-catalytic subunit (ERCC1), transcript variant 3, mRNA" National Center for Biotechnology Information (NCBI) [online]. Retrieved from: www.ncbi.nlm.nih.gov; retrieved on Mar. 28, 2019, 5 pages.
GENBANK Accession No. NM_001172566.1 (Sep. 2, 2018) "*Homo sapiens* MYD88, innate immune signal transduction adaptor (MYD88), transcript variant 5, mRNA" National Center for Biotechnology Information (NCBI) [online]. Retrieved from: www.ncbi.nlm.nih.gov; retrieved on Mar. 28, 2019, 4 pages.
GENBANK Accession No. NM_001172567.1 (Sep. 2, 2018) "*Homo sapiens* MYD88, innate immune signal transduction adaptor (MYD88), transcript variant 1, mRNA" National Center for Biotechnology Information (NCBI) [online]. Retrieved from: www.ncbi.nlm.nih.gov; retrieved on Mar. 28, 2019, 4 pages.
GENBANK Accession No. NM_001172568.1 (Sep. 2, 2018) "*Homo sapiens* MYD88, innate immune signal transduction adaptor (MYD88), transcript variant 3, mRNA" National Center for Biotechnology Information (NCBI) [online]. Retrieved from: www.ncbi.nlm.nih.gov; retrieved on Mar. 28, 2019, 4 pages.
GENBANK Accession No. NM_001172569.1 (Sep. 2, 2018) "*Homo sapiens Homo sapiens* MYD88, innate immune signal transduction adaptor (MYD88), transcript variant 4, mRNA" National Center for Biotechnology Information (NCBI) [online]. Retrieved from: www.ncbi.nlm.nih.gov; retrieved on Mar. 28, 2019, 4 pages.
GENBANK Accession No. NM_001174065.1 (Mar. 12, 2019) "*Homo sapiens* fibroblast growth factor receptor 1 (FGFR1), transceipt variant 12, mRNA" National Center for Biotechnology Information (NCBI) [online]. Retrieved from: www.ncbi.nlm.nih.gov; retrieved on Mar. 28, 2019, 9 pages.
GENBANK Accession No. NM_001174087.1 (Feb. 23, 2019) "*Homo sapiens* nuclear receptor coactivator 3 (NCOA3), transcript variant 3, mRNA" National Center for Biotechnology Information (NCBI) [online], Retrieved from: www.ncbi.nlm.nih.gov; retrieved on Mar. 28, 2019, 10 pages.
GENBANK Accession No. NM_001178078.1 (Mar. 12, 2019) "*Homo sapiens* signal transducer and activator of transceiption 6 (STAT6), transcript variant 1, mRNA" National Center for Biotechnology Information (NCBI) [online]. Retrieved from: www.ncbi.nlm.nih.gov; retrieved on Mar. 27, 2019, 6 pages.
GENBANK Accession No. NM_001178079.1 (Mar. 12, 2019) "*Homo sapiens* signal transducer and activator of transceiption 6 (STAT6), transcript variant 3, mRNA" National Center for Biotechnology Information (NCBI) [online]. Retrieved from: www.ncbi.nlm.nih.gov; retrieved on Mar. 27, 2019, 6 pages.
GENBANK Accession No. NM_001178080.1 (Mar. 12, 2019) "*Homo sapiens* signal transducer and activator of transcription 6 (STAT6), transcript variant 4, mRNA" National Center for Biotechnology Information (NCBI) [online]. Retrieved from: www.ncbi.nlm.nih.gov; retrieved on Mar. 27, 2019, 6 pages.
GENBANK Accession No. NM_001178081.1 (Mar. 12, 2019) "*Homo sapiens* signal transducer and activator of transcription 6 (STAT6), transcript variant 5, mRNA" National Center for Biotechnology Information (NCBI) [online]. Retrieved from: www.ncbi.nlm.nih.gov; retrieved on Mar. 27, 2019, 6 pages.
GENBANK Accession No. NM_001178083.1 (Feb. 23, 2019) "*Homo sapiens* exostosin glycosyltransferase 2 (EXT2), transcript variant 3, mRNA" National Center for Biotechnology Information (NCBI) [online], Retrieved from: www.ncbi.nlm.nih.gov; retrieved on Mar. 27, 2019, 5 pages.
GENBANK Accession No. NM_001178133.1 (Mar. 12, 2019) "*Homo sapiens* SUFU negative regulator of hedgehog signaling (SUFU), transcript variant 2, mRNA" National Center for Biotechnology Information (NCBI) [online]. Retrieved from: www.ncbi.nlm.nih.gov; retrieved on Mar. 27, 2019, 5 pages.
GENBANK Accession No. NM_001193376.1 (Mar. 25, 2019) "*Homo sapiens* telomerase reverse transcriptase (TERT), transcript variant 2, mRNA" National Center for Biotechnology Information (NCBI) [online], Retrieved from: www.ncbi.nlm.nih.gov; retrieved on Mar. 27, 2019, 5 pages.
GENBANK Accession No. NM_001195132.1 (Feb. 10, 2019) "*Homo sapiens* cyclin dependent kinase inhibitor 2A (CDKN2A), transcript

(56) References Cited

OTHER PUBLICATIONS variant 5, mRNA" National Center for Biotechnology Information (NCBI) [online], Retrieved from: www.ncbi.nlm.nih.gov; retrieved on Mar. 27, 2019, 6 pages.

GENBANK Accession No. NM_001200001.1 (Feb. 10, 2019) "*Homo sapiens* notch receptor 2 (NOTCH2), transcript variant 2, mRNA" National Center for Biotechnology Information (NCBI) [online]. Retrieved from: www.ncbi.nlm.nih.gov; retrieved on Mar. 27, 2019, 5 pages.

GENBANK Accession No. NM_001203249.1 (Mar. 25, 2019) "*Homo sapiens* enhancer of zeste 2 polycomb repressive complex 2 subunit (EZH2), transcript variant 5, mRNA" National Center for Biotechnology Information (NCBI) [online]. Retrieved from: www.ncbi.nlm.nih.gov; retrieved on Mar. 27, 2019, 5 pages.

GENBANK Accession No. NM_001211.5 (Feb. 20, 2019) "*Homo sapiens* BUB1 mitotic checkpoint serine/threonine kinase B (BUB1B), mRNA" National Center for Biotechnology Information (NCBI) [online], Retrieved from: www.ncbi.nlm.nih.gov; retrieved on Mar. 27, 2019; 7 pages.

GENBANK Accession No. NM_001242466.1 (Feb. 10, 2019) "*Homo sapiens* phosphoinositide-3-kinase regulatory subunit 1 (PIK3R1), transcript variant 4, mRNA" National Center for Biotechnology Information (NCBI) [online]. Retrieved from: www.ncbi.nlm.nih.gov; retrieved on Mar. 27, 2019, 6 pages.

GENBANK Accession No. NM_001243027.2 (Feb. 3, 2019) "*Homo sapiens* AKT serine/threonine kinase 2 (AKT2), transcript variant 2, mRNA" National Center for Biotechnology Information (NCBI) [online], Retrieved from: www.ncbi.nlm.nih.gov/nuccore; retrieved on Mar. 27, 2019; 5 pages.

GENBANK Accession No. NM_001243744.1 (Feb. 23, 2019) "*Homo sapiens* FA complementation group C (FANCC), transcript variant 3, mRNA" National Center for Biotechnology Information (NCBI) [online]. Retrieved from: www.ncbi.nlm.nih.gov; retrieved on Mar. 27, 2019, 4 pages.

GENBANK Accession No. NM_001270508.1 (Nov. 17, 2018) "*Homo sapiens* TNF alpha induced protein 3 (TNFAIP3), transcript variant 1, mRNA" National Center for Biotechnology Information (NCBI) [online]. Retrieved from: www.ncbi.nlm.nih.gov; retrieved on Mar. 27, 2019, 7 pages.

GENBANK Accession No. NM_001276503.1 (Feb. 24, 2019) "*Homo sapiens* succinate dehydrogenase complex subunit D (SDHD), transcript variant 2, mRNA" National Center for Biotechnology Information (NCBI) [online]. Retrieved from: www.ncbi.nlm.nih.gov; retrieved on Mar. 27, 2019, 4 pages.

GENBANK Accession No. NM_001278433.1 (Feb. 24, 2019) "*Homo sapiens* protein kinase cAMP-dependent type I regulatory subunit alpha (PRKAR1A), transcript variant 6, mRNA" National Center for Biotechnology Information (NCBI) [online]. Retrieved from: www.ncbi.nlm.nih.gov; retrieved on Mar. 27, 2019, 6 pages.

GENBANK Accession No. NM_001278519.1 (Mar. 19, 2019) "*Homo sapiens* MDM4 regulator of p53 (MDM4), transcript variant 7, mRNA" National Center for Biotechnology Information (NCBI) [online], Retrieved from: www.ncbi.nlm.nih.gov; retrieved on Mar. 27, 2019, 6 pages.

GENBANK Accession No. NM_001280552.1 (Feb. 24, 2019) "*Homo sapiens* paired box 5 (PAX5), transcript variant 7, mRNA" National Center for Biotechnology Information (NCBI) [online]. Retrieved from: www.ncbi.nlm.nih.gov; retrieved on Mar. 27, 2019, 6 pages.

GENBANK Accession No. NM_001281435.1 (Dec. 23, 2018) "*Homo sapiens* mitogen-activated protein kinase kinase 4 (MAP2K4), transcript variant 2, mRNA" National Center for Biotechnology Information (NCBI) [online]. Retrieved from: www.ncbi.nlm.nih.gov; retrieved on Mar. 27, 2019, 5 pages.

GENBANK Accession No. NM_001282387.1 (Mar. 4, 2019) "*Homo sapiens* isocitrate dehydrogenase (NADP(+))1, cytosolic (IDH1), transcript variant 3, mRNA " National Center for Biotechnology Information (NCBI) [online]. Retrieved from: www.ncbi.nlm.nih.gov; retrieved on Mar. 27, 2019, 6 pages.

GENBANK Accession No. NM_001282418.1 (Mar. 21, 2019) "*Homo sapiens* stromal antigen 2 (STAG2), transcript variant 5, mRNA" National Center for Biotechnology Information (NCBI) [online]. Retrieved from: www.ncbi.nlm.nih.gov; retrieved on Mar. 27, 2019, 8 pages.

GENBANK Accession No. NM_001285829.1 (Feb. 24, 2019) "*Homo sapiens* CCAAT enhancer binding protein alpha (CEBPA), transcript variant 1, mRNA" National Center for Biotechnology Information (NCBI) [online], Retrieved from: www.ncbi.nlm.nih.gov; retrieved on Mar. 27, 2019, 4 pages.

GENBANK Accession No. NM_001286167.1 (Aug. 28, 2016) "*Homo sapiens* Fanconi anemia complementation group A (FANCA), transcript variant 3, mRNA" National Center for Biotechnology Information (NCBI) [online]. Retrieved from: www.ncbi.nlm.nih.gov; retrieved on Mar. 27, 2019, 5 pages.

GENBANK Accession No. NM_001287344.1 (Feb. 24, 2019) "*Homo sapiens* Bruton tyrosine kinase (BTK), transcript variant 3, mRNA" National Center for Biotechnology Information (NCBI) [online]. Retrieved from: www.ncbi.nlm.nih.gov; retrieved on Mar. 27, 2019, 6 pages.

GENBANK Accession No. NM_001288705.2 (Feb. 26, 2019) "*Homo sapiens* colony stimulating factor 1 receptor (CSF1R), transcript variant 2, mRNA" National Center for Biotechnology Information (NCBI) [online]. Retrieved from: www.ncbi.nlm.nih.gov; retrieved on Mar. 27, 2019, 9 pages.

GENBANK Accession No. NM_001289936.1 (Mar. 4, 2019) "*Homo sapiens* erb-b2 receptor tyrosine kinase 2 (ERBB2), transcript variant 3, mRNA" National Center for Biotechnology Information (NCBI) [online], Retrieved from: www.ncbi.nlm.nih.gov; retrieved on Mar. 27, 2019, 7 pages.

GENBANK Accession No. NM_001290114.1 (Feb. 24, 2019) "*Homo sapiens* isocitrate dehydrogenase (NADP(+)) 2, mitchondrial (IDH2), transcript variant 3, mRNA" National Center for Biotechnology Information (NCBI) [online]. Retrieved from: www.ncbi.nlm.nih.gov; retrieved on Mar. 27, 2019, 4 pages.

GENBANK Accession No. NM_001291241.1 (Mar. 19, 2019) "*Homo sapiens* estrogen receptor 1 (ESR1), transcript variant 6, mRNA" National Center for Biotechnology Information (NCBI) [online]. Retrieved from: www.ncbi.nlm.nih.gov; retrieved on Mar. 27, 2019, 7 pages.

GENBANK Accession No. NM_001291628.1 (Mar. 24, 2019) "*Homo sapiens* dicer 1, ribonuclease III (DICER1), transcript variant 5, mRNA" National Center for Biotechnology Information (NCBI) [online], Retrieved from: www.ncbi.nlm.nih.gov; retrieved on Mar. 27, 2019, 9 pages.

GENBANK Accession No. NM_001291847.1 (Mar. 4, 2019) "*Homo sapiens* IKAROS family zinc finger 1 (IKZF1), transcript variant 17, mRNA" National Center for Biotechnology Information (NCBI) [online]. Retrieved from: www.ncbi.nlm.nih.gov; retrieved on Mar. 27, 2019, 4 pages.

GENBANK Accession No. NM_001291858.1 (Mar. 19, 2019) "*Homo sapiens* insulin like growth factor 1 receptor (IGF1R), transcript variant 2, mRNA" National Center for Biotechnology Information (NCBI) [online]. Retrieved from: www.ncbi.nlm.nih.gov; retrieved on Mar. 27, 2019, 10 pages.

GENBANK Accession No. NM_001291970.1 (Dec. 16, 2018) "*Homo sapiens* DNA polymerase eta (POLH), transcript variant 3, mRNA" National Center for Biotechnology Information (NCBI) [online]. Retrieved from: www.ncbi.nlm.nih.gov; retrieved on Mar. 27, 2019, 8 pages.

GENBANK Accession No. NM_001293231.1 (Feb. 24, 2019) "*Homo sapiens* MYCN proto-oncogene, bHLH transcription factor (MYCN), transcript variant 3, mRNA" National Center for Biotechnology Information (NCBI) [online]. Retrieved from: www.ncbi.nlm.nih.gov; retrieved on Mar. 27, 2019, 4 pages.

GENBANK Accession No. NM_001300734.1 (Feb. 24, 2019) "*Homo sapiens* damage specific DNA binding protein 2 (DDB2), transcript variant D1, mRNA" National Center for Biotechnology Information (NCBI) [online]. Retrieved from: www.ncbi.nlm.nih.gov; retrieved on Mar. 27, 2019, 4 pages.

GENBANK Accession No. NM_001303418.1 (Mar. 4, 2019) "*Homo sapiens* ERCC excision repair 3, TFIIIH core complex helicase subunit (ERCC3), transcript variant 3, mRNA" National Center for

(56) References Cited

OTHER PUBLICATIONS

Biotechnology Information (NCBI) [online]. Retrieved from: www.ncbi.nlm.nih.gov; retrieved on Mar. 27, 2019, 5 pages.
GENBANK Accession No. NM_001308133.1 (Mar. 19, 2019) "*Homo sapiens* FA complementation group M (FANCM), transcript variant 2, mRNA" National Center for Biotechnology Information (NCBI) [online]. Retrieved from: www.ncbi.nlm.nih.gov; retrieved on Mar. 27, 2019, 7 pages.
GENBANK Accession No. NM_001308632.1 (Dec. 16, 2018) "*Homo sapiens* DNA polymerase delta 1, catalytic subunit (POLD1), transcript variant 4, mRNA" National Center for Biotechnology Information (NCBI) [online]. Retrieved from: www.ncbi.nlm.nih.gov; retrieved on Mar. 27, 2019, 5 pages.
GENBANK Accession No. NM_001308824.1 (Feb. 25, 2019) "*Homo sapiens* splicing factor 3b subunit 1 (SF3B1), transcript variant 3, mRNA" National Center for Biotechnology Information (NCBI) [online], Retrieved from: www.ncbi.nlm.nih.gov; retrieved on Mar. 27, 2019, 4 pages.
GENBANK Accession No. NM_001317186.1 (Mar. 25, 2019) "*Homo sapiens* cadherin 1 (CDH1), transcript variant 4, mRNA" National Center for Biotechnology Information (NCBI) [online]. Retrieved from: www.ncbi.nlm.nih.gov; retrieved on Mar. 27, 2019, 5 pages.
GENBANK Accession No. NM_001318832.1 (Mar. 24, 2019) "*Homo sapiens* TSC complex subunit 2 (TSC2), transcript variant 9, mRNA" National Center for Biotechnology Information (NCBI) [online]. Retrieved from: www.ncbi.nlm.nih.gov; retrieved on Mar. 27, 2019, 6 pages.
GENBANK Accession No. NM_001319984.1 (Mar. 4, 2019) "*Homo sapiens* FA complementation group D2 (FANCD2), transcript variant 3, mRNA" National Center for Biotechnology Information (NCBI) [online], Retrieved from: www.ncbi.nlm.nih.gov; retrieved on Mar. 27, 2019, 8 pages.
GENBANK Accession No. NM_001320893.1 (Mar. 24, 2019) "*Homo sapiens* DNA methyltransferase 3 alpha (DNMT3A), transcript variant 6, mRNA" National Center for Biotechnology Information (NCBI) [online], Retrieved from: www.ncbi.nlm.nih.gov; retrieved on Mar. 27, 2019, 5 pages.
GENBANK Accession No. NM_001321051.1 (Feb. 26, 2019) "*Homo sapiens* PMS1 homolog 1, mismatch repair system component (PMS1), transcript variant 13, mRNA" National Center for Biotechnology Information (NCBI) [online]. Retrieved from: www.ncbi.nlm.nih.gov; retrieved on Mar. 27, 2019, 3 pages.
GENBANK Accession No. NM_001321857.1 (Mar. 24, 2019) "*Homo sapiens* Janus kinase 1 (JAK1), transcript variant 8, mRNA" National Center for Biotechnology Information (NCBI) [online]. Retrieved from: www.ncbi.nlm.nih.gov; retrieved on Mar. 27, 2019, 6 pages.
GENBANK Accession No. NM_001322195.1 (Mar. 24, 2019) "*Homo sapiens* Janus kinase 2 (JAK2), transcript variant 3, mRNA" National Center for Biotechnology Information (NCBI) [online]. Retrieved from: www.ncbi.nlm.nih.gov; retrieved on Mar. 27, 2019, 7 pages.
GENBANK Accession No. NM_001322262.1 (Feb. 25, 2019) "*Homo sapiens* cyclin E1 (CCNE1), transcript variant 5, mRNA" National Center for Biotechnology Information (NCBI) [online]. Retrieved from: www.ncbi.nlm.nih.gov; retrieved on Mar. 27, 2019, 4 pages.
GENBANK Accession No. NM_001324162.1 (Feb. 26, 2019) "*Homo sapiens* FA complementation group B (FANCB), transcript variant 3, mRNA" National Center for Biotechnology Information (NCBI) [online]. Retrieved from: www.ncbi.nlm.nih.gov; retrieved on Mar. 27, 2019, 4 pages.
GENBANK Accession No. NM_001330437.1 (Mar. 24, 2019) "*Homo sapiens* protein tyrosine phosphatase non-receptor type 11 (PTPN11), transcript variant 3, mRNA" National Center for Biotechnology Information (NCBI) [online]. Retrieved from: www.ncbi.nlm.nih.gov; retrieved on Mar. 27, 2019, 7 pages.
GENBANK Accession No. NM_001346900.1 (Mar. 12, 2019) "*Homo sapiens* epidermal growth factor receptor (EGFR), transcript variant 8, mRNA" National Center for Biotechnology Information (NCBI) [online], Retrieved from: www.ncbi.nlm.nih.gov; retrieved on Mar. 27, 2019, 6 pages.
GENBANK Accession No. NM_001429.3 (Nov. 12, 2018) "*Homo sapiens* E1A binding protein p300 (EP300), transcript variant 1, mRNA" National Center for Biotechnology Information (NCBI) [online]. Retrieved from: www.ncbi.nlm.nih.gov; retrieved on Mar. 27, 2019, 11 pages.
GENBANK Accession No. NM_001982.3 (Mar. 4, 2019) "*Homo sapiens* erb-b2 receptor tyrosine kinase 3 (ERBB3), transcript variant 1, mRNA" National Center for Biotechnology Information (NCBI) [online], Retrieved from: www.ncbi.nlm.nih.gov; retrieved on Mar. 27, 2019, 8 pages.
GENBANK Accession No. NM_002020.4 (Mar. 19, 2019) "*Homo sapiens* fms related tyrosine kinase 4(FLT4), transcript variant 2, mRNA" National Center for Biotechnology Information (NCBI) [online]. Retrieved from: www.ncbi.nlm.nih.gov; retrieved on Mar. 27, 2019, 8 pages.
GENBANK Accession No. NM_002049.3 (Feb. 21, 2019) "*Homo sapiens* GATA binding protein 1 (GATA1), mRNA" National Center for Biotechnology Information (NCBI) [online]. Retrieved from: www.ncbi.nlm.nih.gov; retrieved on Mar. 27, 2019, 6 pages.
GENBANK Accession No. NM_002067.4 (Sep. 23, 2018) "*Homo sapiens* G protein subunit alpha 11 (GNA11), mRNA" National Center for Biotechnology Information (NCBI) [online]. Retrieved from: www.ncbi.nlm.nih.gov; retrieved on Mar. 27, 2019, 5 pages.
GENBANK Accession No. NM_002072.4 (Mar. 19, 2019) "*Homo sapiens* G protein subunit alpha q (GNAQ), mRNA" National Center for Biotechnology Information (NCBI) [online]. Retrieved from: www.ncbi.nlm.nih.gov; retrieved on Mar. 27, 2019, 5 pages.
GENBANK Accession No. NM_002107.4 (Nov. 11, 2018) "*Homo sapiens* H3 histone family member 3A (H3F3A), mRNA" National Center for Biotechnology Information (NCBI) [online]. Retrieved from: www.ncbi.nlm.nih.gov; retrieved on Mar. 27, 2019, 10 pages.
GENBANK Accession No. NM_002253.2 (Dec. 18, 2017) "*Homo sapiens* kinase insert domain receptor (KDR), mRNA" National Center for Biotechnology Information (NCBI) [online]. Retrieved from: www.ncbi.nlm.nih.gov; retrieved on Mar. 27, 2019, 7 pages.
GENBANK Accession No. NM_002467.4 (Aug. 7, 2017) "*Homo sapiens* MYC proto-oncogene, bHLH transcription factor (MYC), mRNA" National Center for Biotechnology Information (NCBI) [online]. Retrieved from: www.ncbi.nlm.nih.gov; retrieved on Mar. 27, 2019, 5 pages.
GENBANK Accession No. NM_002468.4 (Sep. 2, 2018) "*Homo sapiens* MYD88, innate immune signal transduction adaptor (MYD88), transcript variant 2, mRNA" National Center for Biotechnology Information (NCBI) [online]. Retrieved from: www.ncbi.nlm.nih.gov; retrieved on Mar. 27, 2019, 4 pages.
GENBANK Accession No. NM_002520.6 (Feb. 24, 2019) "*Homo sapiens* nucleophosmin 1 (NPM1), transcript variant 1, mRNA" National Center for Biotechnology Information (NCBI) [online]. Retrieved from: www.ncbi.nlm.nih.gov; retrieved on Mar. 27, 2019, 8 pages.
GENBANK Accession No. NM_002524.4 (Nov. 18, 2018) "*Homo sapiens* NRAS proto-oncogene, GTPase (NRAS), mRNA" National Center for Biotechnology Information (NCBI) [online]. Retrieved from: www.ncbi.nlm.nih.gov; retrieved on Mar. 27, 2019, 5 pages.
GENBANK Accession No. NM_002755.3 (Feb. 18, 2019) "*Homo sapiens* mitogen-activated protein kinase kinase 1 (MAP2K1), mRNA" National Center for Biotechnology Information (NCBI) [online]. Retrieved from: www.ncbi.nlm.nih.gov; retrieved on Mar. 27, 2019, 5 pages.
GENBANK Accession No. NM_002769.4 (Nov. 17, 2018) "*Homo sapiens* serine protease 1 (PRSS1), mRNA" National Center for Biotechnology Information (NCBI) [online]. Retrieved from: www.ncbi.nlm.nih.gov; retrieved on Mar. 27, 2019, 4 pages.
GENBANK Accession No. NM_002880.3 (Mar. 25, 2019) "*Homo sapiens* Raf-1 proto-oncogene, serine/threonine kinase (RAF1), transcript variant 2, mRNA" National Center for Biotechnology Information (NCBI) [online]. Retrieved from: www.ncbi.nlm.nih.gov; retrieved on Mar. 27, 2019; 7 pages.
GENBANK Accession No. NM_002944.2 (Mar. 25, 2019) "*Homo sapiens* ROS proto-oncogene 1, receptor tyrosine kinase (ROS1),

(56) References Cited

OTHER PUBLICATIONS mRNA" National Center for Biotechnology Information (NCBI) [online]. Retrieved from: www.ncbi.nlm.nih.gov; retrieved on Mar. 27, 2019, 10 pages.
GENBANK Accession No. NM_003153.4 (Oct. 21, 2018) "*Homo sapiens* signal transducer and activator of transcription 6 (STAT6), transcript variant 2, mRNA" National Center for Biotechnology Information (NCBI) [online]. Retrieved from: www.ncbi.nlm.nih.gov; retrieved on Mar. 27, 2019, 6 pages.
GENBANK Accession No. NM_003286.3 (Oct. 26, 2018) "*Homo sapiens* DNA topoisomerase I (TOP1), mRNA" National Center for Biotechnology Information (NCBI) [online]. Retrieved from: www.ncbi.nlm.nih.gov; retrieved on Mar. 27, 2019, 7 pages.
GENBANK Accession No. NM_003600.3 (Mar. 19, 2019) "*Homo sapiens* aurora kinase A (AURKA), transcript variant 2, mRNA" National Center for Biotechnology Information (NCBI) [online]. Retrieved from: www.ncbi.nlm.nih.gov; retrieved on Mar. 27, 2019, 5 pages.
GENBANK Accession No. NM_003745.1 (Mar. 4, 2019) "*Homo sapiens* suppressor of cytokine signaling 1 (SOCS1), mRNA" National Center for Biotechnology Information (NCBI) [online]. Retrieved from: www.ncbi.nlm.nih.gov; retrieved on Mar. 27, 2019, 4 pages.
GENBANK Accession No. NM_003797 (Jun. 27, 2012) "*Homo sapiens* embryonic ectoderm development (EED), transcript variant 1, mRNA" National Center for Biotechnology Information (NCBI) [online]. Retrieved from: www.ncbi.nlm.nih.gov; retrieved on Jul. 23, 2012, 5 pages.
GENBANK Accession No. NM_003924.3 (Jan. 13, 2019) "*Homo sapiens* paired like homeobox 2B (PHOX2B), mRNA" National Center for Biotechnology Information (NCBI) [online]. Retrieved from: www.ncbi.nlm.nih.gov; retrieved on Mar. 27, 2019, 4 pages.
GENBANK Accession No. NM_004064.4 (Mar. 12, 2019) "*Homo sapiens* cyclin dependent kinase inhibitor 1B (CDKN1B), mRNA" National Center for Biotechnology Information (NCBI) [online]. Retrieved from: www.ncbi.nlm.nih.gov; retrieved on Mar. 27, 2019, 5 pages.
GENBANK Accession No. NM_004119.2 (Mar. 4, 2019) "*Homo sapiens* fms related tyrosine kinase 3 (FLT3), transcript variant 1, mRNA" National Center for Biotechnology Information (NCBI) [online]. Retrieved from: www.ncbi.nlm.nih.gov; retrieved on Mar. 27, 2019, 8 pages.
GENBANK Accession No. NM_004260.3 (Feb. 22, 2019) "*Homo sapiens* RecQ like helicase 4 (RECQL4), mRNA" National Center for Biotechnology Information (NCBI) [online]. Retrieved from: www.ncbi.nlm.nih.gov; retrieved on Mar. 27, 2019, 5 pages.
GENBANK Accession No. NM_004304.4 (Nov. 4, 2018) "*Homo sapiens* ALK receptor tyrosine kinase (ALK), transcript variant 1, mRNA" National Center for Biotechnology Information (NCBI) [online]. Retrieved from: www.ncbi.nlm.nih.gov; retrieved on Mar. 27, 2019, 7 pages.
GENBANK Accession No. NM_004329.2 (Feb. 16, 2019) "*Homo sapiens* bone morphogenetic protein receptor type 1A (BMPR1A), mRNA" National Center for Biotechnology Information (NCBI) [online]. Retrieved from: www.ncbi.nlm.nih.gov; retrieved on Mar. 27, 2019, 5 pages.
GENBANK Accession No. NM_004333.4 (Jul. 17, 2017) "*Homo sapiens* B-Raf proto-oncogene, serine/threonine kinase (BRAF), mRNA" National Center for Biotechnology Information (NCBI) [online], Retrieved from: www.ncbi.nlm.nih.gov; retrieved on Mar. 27, 2019; 6 pages.
GENBANK Accession No. NM 004343.3 (Feb. 10, 2019) "*Homo sapiens* calreticulin (CALR), mRNA" National Center for Biotechnology Information (NCBI) [online]. Retrieved from: www.ncbi.nlm.nih.gov; retrieved on Mar. 27, 2019, 5 pages.
GENBANK Accession No. NM_004380.2 (Mar. 4, 2019) "*Homo sapiens* CREB binding protein (CREBBP), transcript variant 1, mRNA" National Center for Biotechnology Information (NCBI) [online]. Retrieved from: www.ncbi.nlm.nih.gov; retrieved on Mar. 27, 2019, 12 pages.
GENBANK Accession No. NM 004447.5 (Jun. 26, 2012) "*Homo sapiens* epidermal growth factor receptor pathway subsuate 8 (EPS8), mRNA" National Center for Biotechnology Information (NCBI) [online], Retrieved from: www.ncbi.nlm.nih.gov, retrieved on Jul. 23, 2012, 5 pages.
GENBANK Accession No. NM_004454.2 (Nov. 11, 2018) "*Homo sapiens* ETS variant 5 (ETV5), mRNA" National Center for Biotechnology Information (NCBI) [online]. Retrieved from: www.ncbi.nlm.nih.gov; retrieved on Mar. 27, 2019, 5 pages.
GENBANK Accession No. NM_004456.4 (Mar. 25, 2019) "*Homo sapiens* enhancer of zeste 2 polycomb repressive complex 2 subunit (EZH2), transcript variant 1, mRNA" National Center for Biotechnology Information (NCBI) [online]. Retrieved from: www.ncbi.nlm.nih.gov; retrieved on Mar. 27, 2019, 6 pages.
GENBANK Accession No. NM_004628.4 (Mar. 25, 2019) "*Homo sapiens* XPC complex subunit, DNA damage recognition and repair factor (XPC), transcript variant 1, mRNA" National Center for Biotechnology Information (NCBI) [online]. Retrieved from: www.ncbi.nlm.nih.gov; retrieved on Mar. 27, 2019, 7 pages.
GENBANK Accession No. NM_004629.1 (Mar. 25, 2019) "*Homo sapiens* FA complementation group G (FANCG), mRNA" National Center for Biotechnology Information (NCBI) [online]. Retrieved from: www.ncbi.nlm.nih.gov; retrieved on Mar. 27, 2019, 5 pages.
GENBANK Accession No. NM_004655.3 (May 13, 2018) "*Homo sapiens* axin2 (AXIN2), mRNA" National Center for Biotechnology Information (NCBI) [online]. Retrieved from: www.ncbi.nlm.nih.gov; retrieved on Mar. 27, 2019, 5 pages.
GENBANK Accession No. NM_004656.3 (Oct. 25, 2018) "*Homo sapiens* BRCA1 associated protein 1 (BAP1), mRNA" National Center for Biotechnology Information (NCBI) [online]. Retrieved from: www.ncbi.nlm.nih.gov; retrieved on Mar. 27, 2019, 6 pages.
GENBANK Accession No. NM_004958.3 (Mar. 25, 2019) "*Homo sapiens* mechanistic target of rapamycin kinase (MTOR), mRNA" National Center for Biotechnology Information (NCBI) [online]. Retrieved from: www.ncbi.nlm.nih.gov; retrieved on Mar. 27, 2019, 13 pages.
GENBANK Accession No. NM_005120.2 (Oct. 28, 2018) "*Homo sapiens* mediator complex subunit 12 (MED 12), mRNA" National Center for Biotechnology Information (NCBI) [online]. Retrieved from: www.ncbi.nlm.nih.gov; retrieved on Mar. 27, 2019, 9 pages.
GENBANK Accession No. NM_005157 (Mar. 12, 2019) "*Homo sapiens* ABL proto-oncogene 1, non-receptor tyrosine kinase (ABL1), transcript variant a, mRNA" National Center for Biotechnology Information (NCBI) [online]. Retrieved from: www.ncbi.nlm.nih.gov; retrieved on Mar. 27, 2019, 10 pages.
GENBANK Accession No. NM_005188.3 (Mar. 25, 2019) "*Homo sapiens* Cbl proto-oncogene (CBL), mRNA" National Center for Biotechnology Information (NCBI) [online]. Retrieved from: www.ncbi.nlm.nih.gov; retrieved on Mar. 27, 2019, 9 pages.
GENBANK Accession No. NM_005235.2 (Oct. 20, 2018) "*Homo sapiens* erb-b2 receptor tyrosine kinase 4 (ERBB4), transcript variant JM-a/CVT-1, mRNA" National Center for Biotechnology Information (NCBI) [online]. Retrieved from: www.ncbi.nlm.nih.gov; retrieved on Mar. 27, 2019; 9 pages.
GENBANK Accession No. NM_005236.2 (Feb. 21, 2019) "*Homo sapiens* ERCC excision repair 4, endonuclease catalytic subunit (ERCC4), mRNA" National Center for Biotechnology Information (NCBI) [online]. Retrieved from: www.ncbi.nlm.nih.gov; retrieved on Mar. 27, 2019, 6 pages.
GENBANK Accession No. NM_005321.2 (Feb. 16, 2019) "*Homo sapiens* histone cluster 1 H1 family member e (HIST1H1e), mRNA" National Center for Biotechnology Information (NCBI) [online]. Retrieved from: www.ncbi.nlm.nih.gov; retrieved on Mar. 27, 2019, 5 pages.
GENBANK Accession No. NM_005324.4 (Nov. 4, 2018) "*Homo sapiens* H3 histone family member 3B (H3F3B), mRNA" National Center for Biotechnology Information (NCBI) [online]. Retrieved from: www.ncbi.nlm.nih.gov; retrieved on Mar. 27, 2019, 11 pages.
GENBANK Accession No. NM_005359.5 (Feb. 20, 2019) "*Homo sapiens* SMAD family member 4 (SMAD4), mRNA" National Center for Biotechnology Information (NCBI) [online]. Retrieved from: www.ncbi.nlm.nih.gov; retrieved on Mar. 27, 2019, 7 pages.

(56) References Cited

OTHER PUBLICATIONS

GENBANK Accession No. NM_005373.2 (Feb. 20, 2019) "*Homo sapiens* MPL proto-oncogene, thrombopoietin receptor (MPL), mRNA" National Center for Biotechnology Information (NCBI) [online], Retrieved from: www.ncbi.nlm.nih.gov; retrieved on Mar. 27, 2019, 6 pages.
GENBANK Accession No. NM_005417.4 (Mar. 12, 2019) "*Homo sapiens* SRC proto-oncogene, non-receptor tyrosine kinase (SRC), transcript variant 1, mRNA" National Center for Biotechnology Information (NCBI) [online]. Retrieved from: www.ncbi.nlm.nih.gov; retrieved on Mar. 27, 2019, 5 pages.
GENBANK Accession No. NM 005610 (Jun. 27, 2012) "*Homo sapiens* retinoblastoma binding protein 4 (RBBP4), transcript variant 1, mRNA" National Center for Biotechnology Information (NCBI) [online], Retrieved from: www.ncbi.nlm.nih.gov; retrieved on Jul. 23, 2012, 7 pages.
GENBANK Accession No. NM_005631.4 (Sep. 30, 2018) "*Homo sapiens* smoothened, frizzled class receptor (SMO), mRNA" National Center for Biotechnology Information (NCBI) [online]. Retrieved from: www.ncbi.nlm.nih.gov; retrieved on Mar. 27, 2019, 5 pages.
GENBANK Accession No. NM_006015.4 (May 20, 2017) "*Homo sapiens* AT-rich interaction domain 1A (ARID1A), transcript variant 1, mRNA" National Center for Biotechnology Information (NCBI) [online]. Retrieved from: www.ncbi.nlm.nih.gov; retrieved on Mar. 27, 2019, 9 pages.
GENBANK Accession No. NM_006206.4 (Sep. 9, 2016) "*Homo sapiens* platelet derived growth factor receptor alpha (PDGFRA), mRNA" National Center for Biotechnology Information (NCBI) [online]. Retrieved from: www.ncbi.nlm.nih.gov; retrieved on Mar. 27, 2019, 6 pages.
GENBANK Accession No. NM_006218.3 (Nov. 18, 2018) "*Homo sapiens* phosphatidylinositol-4,5-bisphosphate 3-kinase catalytic subunit alpha (PIK3CA), mRNA" National Center for Biotechnology Information (NCBI) [online]. Retrieved from: www.ncbi.nlm.nih.gov; retrieved on Mar. 27, 2019, 7 pages.
GENBANK Accession No. NM_006231.3 (Feb. 26, 2019) "*Homo sapiens* DNA polymerase epsilon, catalytic subunit (POLE), mRNA" National Center for Biotechnology Information (NCBI) [online]. Retrieved from: www.ncbi.nlm.nih.gov; retrieved on Mar. 27, 2019, 8 pages.
GENBANK Accession No. NM_006297.2 (Mar. 12, 2019) "*Homo sapiens* X-ray repair cross complementing 1 (XRCC1), mRNA" National Center for Biotechnology Information (NCBI) [online]. Retrieved from: www.ncbi.nlm.nih.gov; retrieved on Mar. 27, 2019, 7 pages.
GENBANK Accession No. NM_007294.3 (Feb. 21, 2019) "*Homo sapiens* BRCA1 DNA repair associated (BRCA1), transcript variant 1, mRNA" National Center for Biotechnology Information (NCBI) [online], Retrieved from: www.ncbi.nlm.nih.gov; retrieved on Mar. 27, 2019, 12 pages.
GENBANK Accession No. NM_014757.4 (Sep. 2, 2018) "*Homo sapiens* mastermind like transcriptional coactivator 1 (MAML1), mRNA" National Center for Biotechnology Information (NCBI) [online]. Retrieved from: www.ncbi.nlm.nih.gov; retrieved on Mar. 27, 2019, 5 pages.
GENBANK Accession No. NM_015125.4 (Mar. 4, 2019) "*Homo sapiens* capicua transcriptional repressor (CIC), transcript variant 2, mRNA" National Center for Biotechnology Information (NCBI) [online]. Retrieved from: www.ncbi.nlm.nih.gov; retrieved on Mar. 27, 2019, 8 pages.
GENBANK Accession No. NM_015338.5 (Mar. 12, 2019) "*Homo sapiens* ASXL transcriptional regulator 1 (ASXL1), transcript variant 1, mRNA" National Center for Biotechnology Information (NCBI) [online]. Retrieved from: www.ncbi.nlm.nih.gov; retrieved on Mar. 27, 2019, 7 pages.
GENBANK Accession No. NM_015355.2 (Jun. 28, 2012) "*Homo sapiens* suppressor of zeste 12 homolog (*Drosophila*)(SUZ12), mRNA" National Center for Biotechnology Information (NCBI) [online]. Retrieved from: www.ncbi.nlm.nih.gov; retrieved on Jul. 23, 2012, 6 pages.
GENBANK Accession No. NM_016038.2 (Feb. 20, 2016) "*Homo sapiens* SBDS ribosome assembly guanine nucleotide exchange factor (SBDS), mRNA" National Center for Biotechnology Information (NCBI) [online], Retrieved from: www.ncbi.nlm.nih.gov; retrieved on Mar. 27, 2019, 3 pages.
GENBANK Accession No. NM_017617.4 (Mar. 29, 2018) "*Homo sapiens* notch 1 (NOTCH1), mRNA" National Center for Biotechnology Information (NCBI) [online]. Retrieved from: www.ncbi.nlm.nih.gov; retrieved on Mar. 27, 2019, 9 pages.
GENBANK Accession No. NM_017628.4 (Mar. 19, 2019) "*Homo sapiens* let methylcytosine dioxygenase 2 (TET2), transcript variant 2, mRNA" National Center for Biotechnology Information (NCBI) [online], Retrieved from: www.ncbi.nlm.nih.gov; retrieved on Mar. 27, 2019, 6 pages.
GENBANK Accession No. NM_017763.5 (Feb. 25, 2019) "*Homo sapiens* ring finger protein 43 (RNF43), transcript variant 1, mRNA" National Center for Biotechnology Information (NCBI) [online]. Retrieved from: www.ncbi.nlm.nih.gov; retrieved on Mar. 27, 2019, 6 pages.
GENBANK Accession No. NM_017841.2 (Feb. 23, 2019) "*Homo sapiens* succinate dehydrogenase complex assembly factor 2 (SDHAF2), mRNA" National Center for Biotechnology Information (NCBI) [online], Retrieved from: www.ncbi.nlm.nih.gov; retrieved on Mar. 27, 2019, 4 pages.
GENBANK Accession No. NM_018193.2 (Feb. 17, 2019) "*Homo sapiens* FA complementation group I (FANCI), transcript variant 2, mRNA" National Center for Biotechnology Information (NCBI) [online], Retrieved from: www.ncbi.nlm.nih.gov; retrieved on Mar. 27, 2019, 6 pages.
GENBANK Accession No. NM_018315.4 (Apr. 23, 2018) "*Homo sapiens* F-box and WD repeat domain containing 7 (FBXW7), transcript variant 2, mRNA" National Center for Biotechnology Information (NCBI) [online]. Retrieved from: www.ncbi.nlm.nih.gov; retrieved on Mar. 27, 2019, 5 pages.
GENBANK Accession No. NM_020732.3 (Feb. 23, 2019) "*Homo sapiens* AT-rich interaction domain 1b (ARID1B), transcript variant 2, mRNA" National Center for Biotechnology Information (NCBI) [online]. Retrieved from: www.ncbi.nlm.nih.gov; retrieved on Mar. 27, 2019, 9 pages.
GENBANK Accession No. NM_021922.2 (Feb. 17, 2019) "*Homo sapiens* FA complementation group E (FANCE), mRNA" National Center for Biotechnology Information (NCBI) [online]. Retrieved from: www.ncbi.nlm.nih.gov; retrieved on Mar. 27, 2019, 5 pages.
GENBANK Accession No. NM_022725.3. (Feb. 18, 2019) "*Homo sapiens* FA complementation group F (FANCF), mRNA" National Center for Biotechnology Information (NCBI) [online]. Retrieved from: www.ncbi.nlm.nih.gov; retrieved on Mar. 27, 2019, 4 pages.
GENBANK Accession No. NM_023067.3 (Sep. 30, 2018) "*Homo sapiens* forkhead box L2 (FOXL2), mRNA" National Center for Biotechnology Information (NCBI) [online]. Retrieved from: www.ncbi.nlm.nih.gov; retrieved on Mar. 27, 2019, 4 pages.
GENBANK Accession No. NM_024529.4 (Mar. 4, 2019) "*Homo sapiens* cell division cycle 73 (CDC73), mRNA" National Center for Biotechnology Information (NCBI) [online]. Retrieved from: www.ncbi.nlm.nih.gov; retrieved on Mar. 27, 2019, 6 pages.
GENBANK Accession No. NM_024675.3 (Mar. 12, 2019) "*Homo sapiens* partner and localizer of BRCA2 (PALB2), mRNA" National Center for Biotechnology Information (NCBI) [online]. Retrieved from: www.ncbi.nlm.nih.gov; retrieved on Mar. 27, 2019, 6 pages.
GENBANK Accession No. NM_032043.21 (Mar. 25, 2019) "*Homo sapiens* BRCA1 interacting protein C-terminal helicase 1 (BRIP1), mRNA" National Center for Biotechnology Information (NCBI) [online], Retrieved from: www.ncbi.nlm.nih.gov; retrieved on Mar. 27, 2019, 8 pages.
GENBANK Accession No. NM_033360.3 (Mar. 24, 2019) "*Homo sapiens* KRAS proto-oncogene, GTPase (KRAS), transcript variant a, mRNA" National Center for Biotechnology Information (NCBI) [online], Retrieved from: www.ncbi.nlm.nih.gov; retrieved on Mar. 27, 2019, 7 pages.
GENBANK Accession No. NM_053056.2 (Mar. 25, 2019) "*Homo sapiens* cyclin D1 (CCND1), mRNA" National Center for Biotechnology Information (NCBI) [online]. Retrieved from: www.ncbi.nlm.nih.gov; retrieved on Mar. 27, 2019, 5 pages.

(56) References Cited

OTHER PUBLICATIONS

GENBANK Accession No. NM_078487.2 (Mar. 4, 2019) "*Homo sapiens*" National Center for Biotechnology Information (NCBI) [online]. Retrieved from: www.ncbi.nlm.nih.gov; retrieved on Mar. 27, 2019, 5 pages.

GENBANK Accession No. NM_078626.2 (Nov. 10, 2018) "*Homo sapiens* cyclin dependent kinase inhibitor 2C (CDKN2C), transcript variant 2, mRNA" National Center for Biotechnology Information (NCBI) [online], Retrieved from: www.ncbi.nlm.nih.gov; retrieved on Mar. 28, 2019, 4 pages.

GENBANK Accession No. NM_080425.3 (Mar. 25, 2019) "*Homo sapiens* GNAS complex locus (GNAS), transcript variant 2, mRNA" National Center for Biotechnology Information (NCBI) [online]. Retrieved from: www.ncbi.nlm.nih.gov; retrieved on Mar. 28, 2019, 6 pages.

GENBANK Accession No. NM_130804.2 (Mar. 4, 2019) "*Homo sapiens* menin 1 (MEN1), transcript variant e1F1, mRNA" National Center for Biotechnology Information (NCBI) [online]. Retrieved from: www.ncbi.nlm.nih.gov; retrieved on Mar. 28, 2019, 5 pages.

GENBANK Accession No. NM_144606.5 (Jun. 4, 2017) "*Homo sapiens* folliculin (FLCN), transcript variant 2, mRNA" National Center for Biotechnology Information (NCBI) [online]. Retrieved from: www.ncbi.nlm.nih.gov; retrieved on Mar. 28, 2019, 4 pages.

GENBANK Accession No. NM_145862.2 (Mar. 12, 2019) "*Homo sapiens* checkpoint kinase 2 (CHEK2), transcript variant 2, mRNA" National Center for Biotechnology Information (NCBI) [online]. Retrieved from: www.ncbi.nlm.nih.gov; retrieved on Mar. 28, 2019, 4 pages.

GENBANK Accession No. NM_152998.2 (Mar. 25, 2019) "*Homo sapiens* enhancer of zeste 2 polycomb repressive complex 2 subunit (EZH2), transcript variant 2, mRNA" National Center for Biotechnology Information (NCBI) [online]. Retrieved from: www.ncbi.nlm.nih.gov; retrieved on Mar. 28, 2019, 5 pages.

GENBANK Accession No. NM_153207.4 (Jun. 30, 2012) "*Homo sapiens* AE binding protein 2 (AEBP2), transcript variant 1, mRNA" National Center for Biotechnology Information (NCBI) [online]. Retrieved from: www.ncbi.nlm.nih.gov; retrieved on Jul. 23, 2012, 5 pages.

GENBANK Accession No. NM_81042.4 (Mar. 12, 2019) "*Homo sapiens* polybromo 1 (PBRM1), transcript variant 4, mRNA" National Center for Biotechnology Information (NCBI) [online]. Retrieved from: www.ncbi.nlm.nih.gov; retrieved on Mar. 28, 2019, 7 pages.

GENBANK Accession No. NM_181831.2 (Mar. 25, 2019) "*Homo sapiens* neurofibromin 2 (NF2), transcript variant 13, mRNA" National Center for Biotechnology Information (NCBI) [online]. Retrieved from: www.ncbi.nlm.nih.gov; retrieved on Mar. 28, 2019, 6 pages.

GENBANK Accession No. NM_213647.2 (Oct. 21, 2018) "*Homo sapiens* fibroblast growth factor receptor 4 (FGFR4), transcript variant 3, mRNA" National Center for Biotechnology Information (NCBI) [online], Retrieved from: www.ncbi.nlm.nih.gov; retrieved on Mar. 28, 2019, 5 pages.

GENBANK Accession No. NR_103873.1 (Feb. 24, 2019) "*Homo sapiens* RAD51 paralog C (RAD51C), transcript variant 4, non-coding RNA" National Center for Biotechnology Information (NCBI) [online], Retrieved from: www.ncbi.nlm.nih.gov; retrieved on Mar. 28, 2019, 3 pages.

GENBANK Accession No. NR_134950.1 (Mar. 25, 2019) "*Homo sapiens* notch receptor 4 (NOTCH4), transcript variant 3, non-coding RNA" National Center for Biotechnology Information (NCBI) [online], Retrieved from: www.ncbi.nlm.nih.gov; retrieved on Mar. 28, 2019, 6 pages.

GENBANK Accession No. X02596.1 (Oct. 7, 2008) "Human mRNA for bcr (breakpoint cluster region) gene in Philadelphia chromosome" National Center for Biotechnology Information (NCBI) [online]. Retrieved from: www.ncbi.nlm.nih.gov; retrieved on Nov. 1, 2019, 3 pages.

GENPEPT Accession No. NP_001073315.1 (Mar. 4, 2019) "CREB-biding protein isoform b [*Homo sapiens*]" National Center for Biotechnology Information (NCBI) [online]. Retrieved from: www.ncbi.nlm.nih.gov; retrieved on Mar. 28, 2019, 7 pages.

GENPEPT Accession No. NP_001190178.1 (Mar. 25, 2019) "histone-lysine N-methyltransferase EZH2 isoform e [*Homo sapiens*" National Center for Biotechnology Information (NCBI) [online]. Retrieved from: www.ncbi.nlm.nih.gov; retrieved on Mar. 28, 2019, 3 pages.

GENPEPT Accession No. NP_001420.2 (Feb. 26, 2019) "histone acetyltransferase p300 isoform 1 [*Homo sapiens*]" National Center for Biotechnology Information (NCBI) [online]. Retrieved from: www.ncbi.nlm.nih.gov; retrieved on Mar. 28, 2019, 8 pages.

GENPEPT Accession No. NP_004371.2 (Mar. 4, 2019) "CREB-binding protein isoform a [*Homo sapiens*]" National Center for Biotechnology Information (NCBI) [online]. Retrieved from: www.ncbi.nlm.nih.gov; retrieved on Mar. 28, 2019, 7 pages.

GENPEPT Accession No. NP_004447.2 (Mar. 25, 2019) "histone-lysine N-methyltransferase EZH2 isoform a [*Homo sapiens*]" National Center for Biotechnology Information (NCBI) [online]. Retrieved from: www.ncbi.nlm.nih.gov; retrieved on Mar. 28, 2019, 4 pages.

GENPEPT Accession No. NP_694543.1 (Mar. 25, 2019) "histone-lysine N-methyltransferase EZH2 isoform b [*Homo sapiens*]" National Center for Biotechnology Information (NCBI) [online]. Retrieved from: www.ncbi.nlm.nih.gov; retrieved on Mar. 28, 2019, 3 pages.

Gura et al. (1997) "Systems for Identifying New Drugs are Often Faulty" *Science*. 278:1041-1042.

He, J. et al. (2011) "Structure of p300 bound to MEF2 on DNA reveals a mechanism of enhanceosome assembly" *Nucleic Acids Res*, 39(10):4464-4474. Advance Access publication, doi:10.1093/nar/gkr030, 11 pages.

Horning, S. (2006) "Targeted Therapy and Novel Therapies for Diffuse Large B0Cell Lymphoma" *Annals of Oncology*, 17(Suppl 9):ix46-ix47.

Horsman, D.E. et al. (2003) "Follicular lymphoma lacking the t(14;18)(q32;q21): identification of two disease subtypes" *Br J Haematol*, 120:424-433.

Iqbal, J. et al. (Jul. 2004) "BCL2 translocation defines a unique tumor subset within the germinal center B-cell-like diffuse large B-cell lymphoma" *Am J Pathol*, 165(1):159-166.

Johnson et al. (2001) "Relationships Between Drug Activity in NCI Preclinical in vitro and in vivo Models and Early Clinical Trials" *Brit. J. Cancer*. 84(10):1424-1431.

Kato, M. et al. (2009) "Frequent inactivation of A20 in B-cell lymphomas" *Nature*, 459:712-716.

Kirmizis et al. (2003) "Identification of the Polycomb Group Protein SU(Z)12 as a Potential Molecular Target for Human Cancer Therapy" *Mol Cancer Ther*. 2:113-121.

Kirmizis et al. (2004) "Silencing of Human Polycomb Target Genes is Associated With Methylation of Histone H3 Lys 27" *Genes Dev*. 18:1592-1605.

Kleer, C.G. et al. (Sep. 30, 2003) "EZH2 is a marker of aggressive breast cancer and promotes neoplastic transformation of breast epithelial cells" *PNAS*, 100(20):11606-11611.

Knutson, S.J. et al. (Apr. 1, 2014) "Selective Inhibition of EZH2 by EPZ-6438 Leads to Potent Antitumor Activity in EZH2-Mutant Non-Hodgkin Lymphoma" *Mol Cancer Ther*, 13(4):842-854.

Knutson, S.K. et al. (2012) "A selective inhibitor of EZH2 blocks H3K27 methylation and kills mutant lymphoma cells" *Nat Chem Biol*, 8:890-896.

Kubicek, S. et al. (2007) "Reversal of H3K9me2 by a Small Molecule Inhibitor for the G9a Histone Methyltransferase" *Mol. Cell*. 25:473-481.

Kuzmichev et al. (2002) "Histone Methyltransferase Activity Associated With a Human Multiprotein Complex Containing the Enhancer of Zeste Protein" *Genes Dev*. 16:2893-2905.

Lenz, G. and Staudt, L.M. (Apr. 15, 2010) "Aggressive lymphomas" *N Engl J Med*, 362:1417-1429.

Lenz, G. et al. "Molecular subtypes of diffuse large B-cell lymphoma arise by distinct genetic pathways." Proc Natl Acad Sci, 2008, USA 105, pp. 13520-13525.

Liu, X. et al. (2008) "The structural basis of protein acetylation by the p300/CBP transcriptional coactivator" *Nature*, 451:846-850.

(56) References Cited

OTHER PUBLICATIONS

Lohr et al. (Mar. 6, 2012) "Discovery and Prioritization of Somatic Mutations in Diffuse Large B-Cell Lymphoma (DLBCL) by Whole-Exome Sequencing" *PNAS.* 109(10):3879-3884. Epub Feb. 17, 2012.
Majer, C.R. et al. (Jul. 28, 2012)"A687V EZH2 is a gain-of-function mutation found in lymphoma patients" *FEBS Lett*, 586(19):3448-3451.
Mardis, E.R. et al. (2009) "Recurring mutations found by sequencing an acute myeloid leukemia genome" *N Engl J Med*, 361:1058-1066.
Martinez-Garcia, E. et al. (2011) "The MMSET Histone Methyl Transferase Switches Global Histone Methylation and Alters Gene Expression in t(4;14) Multiple Myeloma Cells" *Blood*, 117:211-220.
Martinez-Garcia et al. (Feb. 2010) "Deregulation of H3K27 methylation in cancer" *Nature Genetics*, 42(2):100-101.
Mccabe et al. "EZH2 Inhibition as a Therapeutic Strategy for Lymphoma With EZH2-Activating Mutations." *Nature*, doi:10.1038/nature11606; Epub: Oct. 10, 2012, 7 pages, including supplemental information. Final publication in: *Nature*, 492(7427):108-112.
Mccabe et al. (2012) "Mutation of A677 in Histone Methyltransferase EZH2 in Human B-Cell Lymphoma Promotes Hypertrimethylation of Histone H3 on Lysine 27 (H3K27)" *PNAS*, 109:8:2989-2994, including Supplemental Information.
Milne et al. (2002) "MLL Targets SET Domain Methyltransferase Activity to Hox Gene Promoters" *Mol. Cell*. 10(5):1107-1117.
Miranda, T.B. et al. (Jun. 2009) "DZNep Is a Global Histone Methylation Inhibitor that Reactivates Developmental Genes Not Silenced by DNA Methylation" *Mol Cancer Ther*, 8(6):1579-1588.
Molkentin, J.D. et al. (Jun. 1996) "Mutational analysis of the DNA binding, dimerization, and transcriptional activation domains of MEF2C" *Mol Cell Biol*, 16:2627-2636.
Molkentin, J.D. et al. (1996) "MEF2B Is a Potent Tranactivator Exressed in Early Myogenic Lineages" *Mol Cell Biol*, 16(7):3814-3824.
Morin, R.D. et al. (Feb. 2010) "Somatic mutations altering EZH2 (Tyr641) in follicular and duffuse large B-cell lymphomas of germinal-center origin" *Nature Genetics*, 42(2):181-185 (plus Supplementary Material, 2 pages).
Morin, R.D. et al. (2011) "Frequent mutation of histone-modifying genes in non-Hodgkin lymphoma" *Nature*, 476:298-303.
Müller et al. (2002) "Histone Methyltransferase Activity of a Drosophila Polycomb Group Repressor Complex" *Cell*. 111(2):197-208.
Mullighan, C.G. et al. (2011) "CREBBP mutations in relapsed acute lymphoblastic leukaemia" *Nature*, 471:235-239.
Nakamura et al. (2002) "ALL-1 Is a Histone Methyltransferase That Assembles a Supercomplex of Proteins Involved in Transcriptional Regulation" *Mol. Cell*. 10(5):1119-1128.
Ngo, V.N. et al. (2010) "Oncogenically active MYD88 mutations in human lymphoma" *Nature*, 470:115-119, including Supplemtary Information, 2 pages.
Olivier, M. (2010) "TP53 Mutations in Human Cancers: Origins, Consequences, and Clinical Use" *Cold Spring Harbor Perspective Biology*, 2010:a001008, 17 pages.
Ott, H.M. et al. (Dec. 2014) "A687V EZH2 is a driver of histone H3 lysine 27 (H3K27) hypertrimethylation" *Mol Cancer Ther*, 13(12):3062-3073.
Otte et al. (2003) "Gene Repression by Polycomb Group Protein Complexes: A Distinct Complex for Every Occasion?" *Curr. Opin. Genet. Dev.* 13(5):448-454.
Parsons, D.W. et al. (Jan. 28, 2011) "The Genetic Landscape of the Childhood Cancer Medulloblastoma" *Science*, 331:435-439.
Pasqualucci, L. et al. (2001) "Hypermutation of multiple proto-oncogenes in B-cell diffuse large-cell lymphomas" *Nature*, 412:341-346.
Pasqualucci, L. et al. (2003) "Mutations of the BCL6 proto-oncogene disrupt its negative autoregulation in diffuse large B-cell lymphoma" *Blood*, 101:2914-2923.
Pasqualucci, L. et al. (2004) "Aberrant Somatic Hypermutation Targets an Extensive Set of Genes in Diffuse Large B-Cell Lymphoma" *Blood* (*ASH Annual Meeting Abstracts*), 104:Abstract 1528.
Pasqualucci, L. et al. (Feb. 20, 2006) "Inactivation of the PRDM1/BLIMP1 gene in diffuse large B cell lymphoma" *J Exp Med*, 203:311-317.
Pasqualucci, L. et al. (Mar. 10, 2011) "Inactivating mutations of acetyltransferase genes in B-cell lymphoma" *Nature*, 471:189-195.
Patani, G.A. and Lavoie, E.J. (1996) "Bioisosterism: A Rational Approach in Drug Design" *Chem Rev*, 96:3147-3176.
Pearce et al. "Failure Modes in Anticancer Drug Discovery and Development" in *Cancer Drug Design and Discovery*. Neidle, ed. Boston: Elsevier., 2008; pp. 424-43 5.
Plath et al. (2003) "Role of Histone H3 Lysince 27 Methylation in X Inactivation" *Science*. 300:131-135.
Pleasance, E.D. et al. (2010) "A small-cell lung cancer genome with complex signatures of tobacco exposure" *Nature*, 463:184-190.
*PLoS One* Website Screen Shot showing article views of Wu; Mar. 15, 2018, 1 page.
Pollock et al. (2009) "Epigenetic approaches to cancer therapy" *Drug Discovery Today: Therapeutic Strategies*, 6(2):71-79.
Ribrag, V. et al. (Dec. 3, 2015) "Phase 1 Study of Tazemetostat (EPIZ-6438), an Inhibitor of Enhancer of Zest-Homolog 2 (EZH2): Preliminary Safety and Activity in Relapsed or Refractory Non-Hodgkin Lymphoma (NHL) Patients" 57th Annual Meeting of the American Society of Hematology, Orlando, FL, Dec. 5-8, 2015; Abstract 473 [online]. Retrieved from: https://ash.confex.com/ash/2015/webprogramscheduler/Paper78128.html; 2 pages.
Ri Chon, V. M. et al. (2010) "Lymphoma-Associated Mutations of EZH2 Result in a Change-of-Function" *Blood*, 116(21):312, Abstract 707, 5 pages.
Ryan, R.J.H. et al. (Dec. 14, 2011) "EZH2 Codon 641 Mutations Are Common in BCL2-Rearranged Germinal Center B Cell Lymphomas" *PLOSone*, 6(12):e28585, doi: 10.1371/journal.pone.0028585, 7 pages.
Sagaert, X. et al. (2006) "MALT1 and BCL10 aberrations in MALT lymphomas and their effect on the expression of BCL 10 in the tumour cells" *Modern Pathology*, 19(2):225-232.
Sarma, K. et al. (2008) "EZH2 Requires PHF1 to Efficiently Catalyze H3 Lysine 27 Trimethylation In Vivo" *Mol. Cell. Biol.* 28(8):2718-2731.
Schlegelberger, B. et al. (2001) "Cytogenetic subtyping of diffuse large B-cell lymphyomas" *Ann Hematol*, 80:B32-B34.
Scott, S.P. et al. (Sep. 24, 2002) "One-Step site-directed mutagenesis of ATM cDNA in large (20kb) plasmid consuucts" *Human Mutation, Mutation in Brief*, #539 [online]. Retrieved from: https://onlinelibrary.wiley.com/doi/pdf/10.1002/humu.9068, 4 pages.
Sculley, J.D. et al. (1953) "Some Amide Derivatives of Certain Aminomethylpyridines" *J Am Chem Soc*, 75(14):3400-3403.
Segalat, L. (Jul. 2, 2007) "Loss-of-function genetic diseases and the concept of pharmaceutical targets" *Orphanet Journal of Rare Diseases*, 2:30, doi:10.1186/1750-1172-2-30 [online]. Retrieved from: http://www.OJRD.com/content/2/1/30, 9 pages.
Shah, S.P. et al. (2009) "Mutational evolution in a lobular breast tumour profiled at single nucleotide resolution" *Nature*, 461:809-813.
Shen, X. et al. (2008) "EZH1 Mediates Methylation on Histone H3 Lysine 27 and Complements EZH2 in Maintaining Stem Cell Identity and Executing Pluripotency" *Mol Cell*, 32(4):491-502.
Siegel, R. et al. (2013) "Cancer Statistics, 2013" *CA Cancer J Clin*, 63(1):11-30.
Silva, J. et al. (2003) "Establishment of Histone H3 Methylation on the Inactive X Chromosome Requires Transient Recruitment of Eed-Enx1 Polycomb Group Complexes" *Dev Cell*, 4(4):481-495.
Simon, J.A. et al. (2008) "Roles of the EZH2 histone methyltransferase in cancer epigenetics" *Mutation Research*, 647:21-29.
Simone, J.V. "Oncology: Introduction" in *Cecil Textbook of Medicine. 20th Edition. vol. 1*. Bennett et al. (eds.) Philadelphia: W. B. Saunders Co., 1996; pp. 1004-1104.
Sneeringer, C.J. et al. (Dec. 7, 2010) "Coordinated activities of wild-type plus mutant EZH2 drive tumor-associated hypertrimethylation of lysine 27 on histone H3 (H3K27) in human B-cell lymphomas" *PNAS*, 107(49):20980-20985.

(56) References Cited

OTHER PUBLICATIONS

Tagawa, H. et al. (Sep. 1, 2005) "Comparison of genome profiles for identification of distinct subgroups of diffuse large B-cell lymphoma" *Blood*, 106(5):1770-1777.

Testoni, M. et al. (Jan. 20, 2015) "Genetic lesions in diffuse large B-cell lymphomas" *Annals of Oncology*, 26(6):1069-1080.

Townsend, A.P. et al. (2009) "New S-Adenosyl-L-Methionine Analogues: Synthesis and Reactivity Studies" *Org Lett*, 11(14):2976-2979.

UNIPROTEIN Swiss-Prot Accession No. Q15910 (Jul. 15, 1998) "Histone-lysine N-methyltransferase EZH2" [online]. Retrieved from: www.uniprot.org/uniprot/Q15910.txt?version=113; retrieved on Jul. 23, 2012, 10 pages.

Van Haaften, G. et al. (2009) "Somatic Mutations of the Histone H3K27 Demethylase Gene UTX in Human Cancer" *Nat Genet*, 41:521-523.

Varambally, S. et al. (Oct. 10, 2002) "The polycomb group protein EZH2 is involved in progression of prostate cancer" *Nature*, 419(6907):624-629.

Velichutina, I. et al. (Dec. 9, 2010) "EZH2-mediated epigenetic silencing in germinal center B cells contributes to proliferation and lymphomagenesis" *Blood*, 116(24):5247-5255.

Verma, S.K. et al. (Dec. 13, 2012) "Identification of Potent, Selective, Cell-Active Inhibitors of the Histone Lysine Methyltransferase EZH2" *ACS Med Chem Lett*, 3(12):1091-1096; doi: 10.1021/ml3003346 (published online Oct. 19, 2012).

Wang et al. (2004) "A Novel Human Homologue of *Drosophila* Polycomblike Gene Is Up-Regulated in Multiple Cancers" *Gene*, 343(1):69-78.

Wigle, T. et al. (2011) "The Y641C Mutation of EZH2 Alters Substrate Specificity for Histone H3 Lysine 27 Methylation States" *FEBS Lett*, 585(19):3011-3014.

Wilson et al. (2010) "Epigenetic Antagonism Between Polycomb and SWI/SNF Complexes During Oncogenic Transformation" *Cancer Cell*, 18:316-328.

Wright, G. et al. (Aug. 19, 2003) "A gene expression-based method to diagnose clinically distinct subgroups of diffuse large B cell lymphoma" *PNAS*, 100(17):9991-9996.

Wu, H. et al. (Jan. 11, 2010) "Structural Biology of Human H3K9 Methyltransferases" *PLoS One*, vol. 5, Issue 1, e8570 [online]. Retrieved from: https://doi.org/10.1371/journal.pone.0008570, 10 pages.

Yap, D.B. et al. (2011) "Somatic mutations at EZH2 Y641 act dominantly through a mechanism of selectively altered PRC2 catalytic activity, to increase H3K27 trimethylation" *Blood*, 117:2451-2459.

Yildiz, M. et al. (2015) "Activating STAT6 mutations in follicular lymphoma" *Blood*, 125(4):668-679.

Youn, H-D. et al. (Oct. 22, 1999) "Apoptosis of T cells mediated by Ca2+-induced release of the transcription factor MEF2" *Science*, 286:790-793.

Yu, Y-L. et al. (Mar. 18, 2011) "EZH2 Regulates Neuronal Differentiation of Mesenchymal Stem Cells through PIP5K1C-dependent Calcium Signaling" *J Biol Chem*, 286(11):9657-9667.

Zhang, G.-J. et al. (2004) "Cancer Genetics and Drug Target Selection" in *Molecular Cancer Therapeutics: Strategies for Drug Discovery and Development*. George C. Prendergast (Ed.), John Wiley & Sons, Inc.; pp. 42-53.

clinicaltrials.gov (Jan. 7, 2021) "An Open-Label, Multicenter, Phase 1/2 Study of Tazemetostat (EZH2 Histone Methyl Transferase [HMT] Inhibitor) as a Single Agent in Subjects With Advanced Solid Tumors or With B Cell Lymphomas and Tazemetostat in Combination With Prednisolone in Subjects With DLBCL" Clinical Trials Identifier: NCT01897571; first posted Jul. 12, 2013 [online]. Retrieved from: https://clinicaltrials.gov/ct2/show/ NCT01897571; retrieved on Jul. 3, 2021, 12 pages.

Copeland, R.A. et al. (Aug. 12, 2014) "EZH2 inhibitor EPZ-6438 (E7438) in Non-Hodgkin Lymphoma: Pre-Clinical Models and Early Clinical Observations" Presented at the ASH Lymphoma Biology Meeting [online], Retrieved from: https://www.epizyme.com/wp-content/uploads/2014/08/ASH-Lymphoma-Conference-Copeland-FINAL.pdf; 16 pages.

```
                        SEQUENCE LISTING

<160> NUMBER OF SEQ ID NOS: 4

<210> SEQ ID NO 1
<211> LENGTH: 66
<212> TYPE: PRT
<213> ORGANISM: Homo sapiens

<400> SEQUENCE: 1

Arg Lys Ser Lys Glu Ile Asp Lys Cys Leu Ser Arg Glu Lys Thr Tyr
1               5                   10                  15

Val Lys Arg Leu Val Lys Ile Leu Leu Leu Gly Ala Gly Glu Ser Gly
            20                  25                  30

Lys Ser Thr Phe Leu Lys Gln Met Arg Ile Ile His Gly Gln Asp Phe
        35                  40                  45

Asp Gln Arg Ala Arg Glu Glu Phe Arg Pro Thr Ile Tyr Ser Asn Val
    50                  55                  60

Ile Lys
65

<210> SEQ ID NO 2
<211> LENGTH: 16
<212> TYPE: DNA
<213> ORGANISM: Homo sapiens

<400> SEQUENCE: 2
gctggaggag tcaccc                                                      16

<210> SEQ ID NO 3
<211> LENGTH: 16
<212> TYPE: DNA
<213> ORGANISM: Homo sapiens

<400> SEQUENCE: 3
gtttggctgg gtccca                                                      16

<210> SEQ ID NO 4
<211> LENGTH: 66
<212> TYPE: PRT
<213> ORGANISM: Homo sapiens

<400> SEQUENCE: 4

Arg Lys Ser Lys Glu Ile Asp Lys Cys Leu Ser Arg Glu Lys Thr Tyr
1               5                   10                  15

Val Lys Arg Leu Val Lys Ile Leu Leu Leu Gly Ala Gly Glu Ser Gly
            20                  25                  30

Lys Ser Thr Phe Leu Lys Gln Met Arg Ile Ile His Gly Gln Asp Phe
        35                  40                  45

Asp Gln Arg Ala Arg Glu Glu Phe Arg Pro Thr Ile Tyr Ser Asn Val
    50                  55                  60

Ile Lys
65
```

BIOMARKERS FOR NON-HODGKIN LYMPHOMAS AND USES THEREOF

CROSS-REFERENCE TO RELATED APPLICATIONS

This application is a continuation of U.S. patent application Ser. No. 14/282,837, filed on May 20, 2014 (now allowed), which is a continuation of U.S. patent application Ser. No. 13/805,504, filed on Dec. 19, 2012, which is a U.S. national phase application filed under 35 U.S.C. § 371 claiming benefit to International Patent Application No. PCT/CA2011/000724, filed on Jun. 23, 2011, which in turn claims benefit pursuant to 35 U.S.C. § 119(e) of U.S. Provisional Patent Application No. 61/357,813 filed Jun. 23, 2010 and U.S. Provisional Application No. 61/420,065 filed Dec. 6, 2010, each of which application is hereby incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is EPIZ-047_C03US_SeqList-txt. The text file is 2,024 bytes, was created on Oct. 28, 2021, and is being submitted electronically via EFS-Web.

FIELD OF THE DISCLOSURE

The disclosure relates to methods of testing for cancer and more specifically to methods of testing samples for somatic mutations indicative of B-cell Non-Hodgkin Lymphomas (NHLs).

BACKGROUND OF THE DISCLOSURE

Non-Hodgkin lymphomas (NHLs) are cancers of B, T or natural killer lymphocytes. The two most common types of NHL, follicular lymphoma (FL) and diffuse large B-cell lymphoma (DLBCL), together comprise 60% of new B-cell NHL diagnoses each year in North America [1]. FL is an indolent and typically incurable disease characterized by clinical and genetic heterogeneity. DLBCL is aggressive and likewise heterogeneous, comprising at least two distinct subtypes that respond differently to standard treatments. Both FL and the germinal centre B-cell (GCB) cell of origin (COO) subtype of DLBCL derive from germinal centre B cells whereas the activated B-cell (ABC) variety, which exhibits a more aggressive clinical course, is thought to originate from B cells that have exited, or are poised to exit, the germinal centre [2]. Current knowledge of the specific genetic events leading to DLBCL and FL is limited to the presence of a few recurrent genetic abnormalities [2]. For example, 85-90% of FL and 30-40% of GCB DLBCL cases [3, 4] harbour t(14;18)(q32;q21), which results in deregulated expression of the BCL2 oncoprotein. Other genetic abnormalities unique to GCB DLBCL include amplification of the c-REL gene and of the miR-17-92 microRNA cluster [5]. In contrast to GCB cases, 24% of ABC DLBCLs harbour structural alterations or inactivating mutations affecting PRDM1, which is involved in differentiation of GCB cells into antibody-secreting plasma cells [6]. ABC-specific mutations also affect genes regulating NF-κB signalling [7-9], with TNFAIP3 (A20) and MYD88 [10] the most abundantly mutated in 24% and 39% of cases respectively.

Despite the disparity in response to therapy of the individual subtypes and the knowledge of clear genetic differences between the subtypes, clearly identifying B-cell NHLs remains challenging. Accordingly, there is a need for improved methods of identifying as well as classifying B-cell NHLs including GCB and ABC DLBCLs.

SUMMARY OF THE DISCLOSURE

In one aspect, the present disclosure is directed towards new and useful methods for the identification and/or classification of B-cell NHLs. As described herein, the inventors have (1) identified somatic mutations and (2) determined the prevalence, expression and focal recurrence of mutations in follicular lymphoma (FL) and diffuse large B-cell lymphoma (DLBCL) in order clarify the genetic architecture of B-cell NHLs. Using strategies and techniques applied to cancer genome and transcriptome characterization [11-13], tumour DNA and/or RNA was sequenced from 117 tumour samples and 10 cell lines and 651 genes were identified with evidence of somatic mutation in B-cell NHL. After validation, 109 genes were shown to be somatically mutated in 2 or more NHL cases. The frequency and nature of mutations within MLL2 and MEF2B, which were among the most frequently mutated genes with no previously known role in lymphoma are also described herein.

As set out in Example 1, a number of biomarkers useful for identifying samples with B-cell NHL have been identified. More specifically, the biomarkers listed in Table 1 have been confirmed as somatic mutations in tumour samples from subjects with B-Cell NHL and show significant evidence for positive selection. In another aspect of the disclosure, a number of biomarkers useful for classifying samples into subtypes of B-cell NHLs have been identified. Some biomarkers have been shown to be selectively mutated in either germinal centre B-cell (GCB) Diffuse Large B-cell Lymphoma (DLBCL) or Activated B-Cell (ABC) DLBCL and are therefore useful for classifying samples as belonging to either the GCB or ABC subtype of DLBCL. Thus, application of the methods described herein allows for the identification of those subjects with specific subtypes of B-cell NHL and enable improved disease management and pharmacological treatment with agents best suited to a particular disease subtype.

Remarkably, a number of the biomarkers associated with B-cell NHLs described herein are involved in histone modification. More specifically, the inventors have discovered that at least five biomarkers (MLL2, MEF2B, CREBBP, EP300, EZH2 and HDAC7) shown to be selectively mutated in B-cell NHLs are predicted to be involved in the process of histone modification. Post-translational modifications of histones, such as methylation and acetylation, can affect the accessibility of stretches of genomic DNA to transcription factors. Mutations in MLL2 are predicted to affect levels of histone methylation while mutations in MEF2B are predicted to affect histone acetylation. Moreover, mutations in MEF2B are predicted to affect the ability of MEF2B to regulate acetylation levels via these three enzymes (HDAC7, CREBBP and EP300). Testing a sample for mutations in histone modifying genes is therefore useful for the identification of B-cell NHLs.

Accordingly, in one aspect there is provided a method of identifying a subject as having B-cell non-Hodgkin lymphoma (NHL), the method comprising testing a sample from the subject for a mutation in one or more biomarkers listed in Table 1. In one embodiment, the presence of a mutation in the sample identifies the subject as having B-cell NHL. In one embodiment, the method comprises detecting one or more mutations in a nucleic acid molecule coding for a biomarker. In one embodiment, the method comprises detecting one or more mutations in a polypeptide or protein coding for a biomarker. In one embodiment, the method comprises detecting mutations in one or more histone modifying genes such as MLL2, MEF2B, CREBBP, EP300, EZH2 or HDAC7. In one embodiment, the biomarkers are selected from FOX01, CCND3, BTG2, B2M, TNFRS14, CREBBP, EP300, BCL10, BTG1, GNA13, SGK1, MLL2, MEF2B, CD79B and MYD88. Optionally, 2 or more, 3 or more, 4 or more, 5 or more or greater than 5 of the biomarkers listed in Table 1 or described herein are tested for mutations. The methods described herein also include testing the sample for one or more of the mutations described herein such as those listed in Table 3, Table 5, Table 6, Table 7 or Table 9. In one embodiment, the biomarker is MEF2B and the method comprises detecting a mutation in a nucleic acid molecule or polypeptide corresponding to a mutation at amino acid position K4, Y69, N81 or D83 of the MEF2B polypeptide.

In another aspect of the disclosure, there is provided a method of classifying a subject suspected of having, or having, B-cell non-Hodgkin lymphoma (NHL). In one embodiment, the method comprises testing a sample from the subject for a mutation in one or more biomarkers selected from MEF2B, SGK1, GNA13, and TNFRS14. In one embodiment, samples that have one or more mutations in one or more biomarkers selected from MEF2B, SGK1, GNA13, and TNFRS14 are classified as having germinal centre B-cell (GCB) Diffuse Large B cell lymphoma (DLBCL). Optionally, the method further comprises testing the sample for a mutation in BCL2, TP53 or EZH2.

In one aspect of the disclosure, there is provided a method of classifying a subject suspected of having, or having, B-cell non-Hodgkin lymphoma (NHL) comprising testing the sample for one or more mutations in MYD88 or CD79B. In one embodiment, samples that have a mutation in MYD88 or CD79B are classified as having activated B-cell (ABC) Diffuse Large B cell lymphoma. Optionally, the method for classifying a subject suspected of having, or having, B-cell non-Hodgkin lymphoma (NHL) includes testing for one or more of MEF2B, SGK1, GNA13, TNFRS14, MYD88 or CD79B.

The methods described herein are also useful for classifying a subject in order to select a suitable treatment for the subject. In one embodiment, the methods include selecting a treatment for a subject based on the classification of the sample as GCB DLBCL or ABC DLBCL. For example, in one embodiment the sample is classified as GCB DLBCL, and a treatment is selected that comprises administration of a histone deacetylase (HDAC) inhibitor-class drug. In one embodiment, the methods for classifying a subject described herein comprise testing a sample from the subject for one or more of the mutations listed in Table 3, Table 5, Table 6, Table 7 or Table 9.

In another aspect of the disclosure, there is provided a method of monitoring a subject with B cell non-Hodgkin lymphoma (NHL) comprising testing a first sample from the subject for a mutation in one or more biomarkers listed in Table 1 and comparing the results to a control. Optionally, the control represents results from testing a second sample taken from the subject at an earlier time point. In one embodiment, the method comprises testing one or more biomarkers selected from MLL2, MEF2B, CREBBP, EP300, EZH2, H3K27, FOX01, CCND3, BTG2, B2M, TNFRS14, BCL10, BTG1, GNA13, SGK1, MYD88 and CD79B. In one embodiment, the method comprises testing for one or more of the mutations listed in Table 3, Table 5, Table 6, Table 7 or Table 9.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

One or more embodiments of the present disclosure will now be described in relation to the drawings in which.

DETAILED DESCRIPTION OF THE DISCLOSURE

I. Definitions

Figure 1:
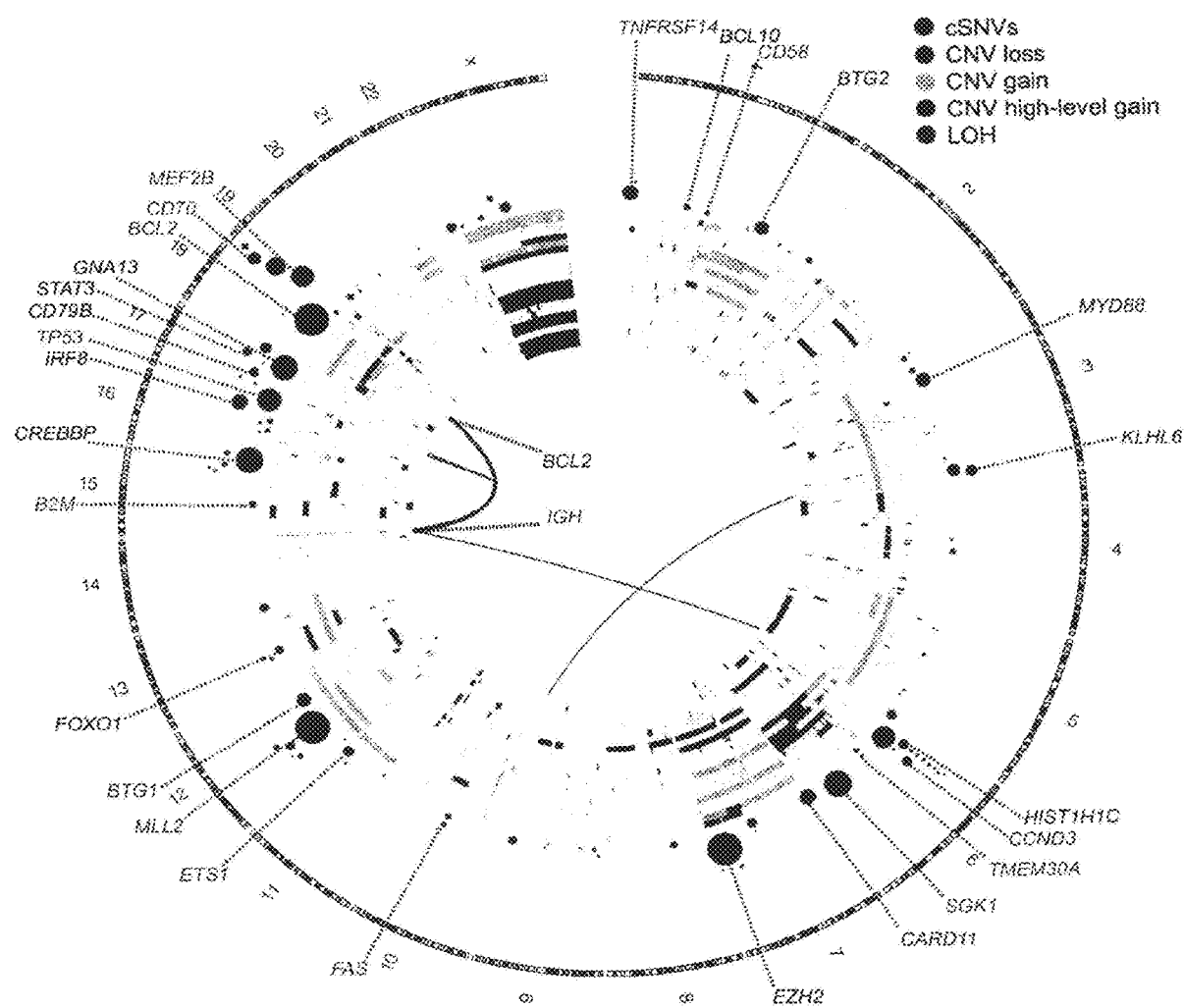
FIG. 1 shows a genome-wide visualization of somatic mutation targets in NHL. Overview of structural rearrangements and copy number variations (CNVs) in the 11 DLBCL genomes and protein-altering single nucleotide variants (coding SNVs; cSNVs) in the 109 recurrently mutated genes identified in our analysis. Inner arcs represent somatic fusion transcripts identified in one of the 11 genomes. The CNVs (copy number variants) and LOH (loss of heterozygosity) detected in each of the 11 DLBCL tumour/normal pairs are displayed on the concentric sets of rings. The inner 11 rings show regions of enhanced homozygosity plotted with blue (interpreted as LOH). The outer 11 rings show somatic CNVs. Purple circles indicate the position of genes with at least two confirmed somatic mutations with circle diameter proportional to the number of cases with cSNVs detected in that gene. Circles representing the genes with significant evidence for positive selection are labeled. Coincidence between recurrently mutated genes and regions of gain/loss are colour-coded in the labels (green=loss, red=gain). For example B2M, which encodes beta-2-microglobulin, is recurrently mutated and is deleted in two cases.

As used herein, "B-cell Non-Hodgkin Lymphoma" or "B-cell NHL" refers to any lymphoma of B-cells except those classified as Hodgkin lymphoma. As used herein, "lymphoma" refers to a cancer in the lymphatic cells of the immune system.

As used herein, "follicular lymphoma" or "FL" refers to a lymphoma of follicle center B-cells (centrocytes and centroblasts), which has at least a partially follicular pattern.

As used herein, "Diffuse Large B cell lymphoma" or "DLBCL" refers to a lymphoma of B-cells wherein the cells are generally about 4-5 times the diameter of small lymphocytes and typically have marked cell-to-cell variation in size and shape. Typically, their cytoplasm is basophilic and moderate in abundance.

Nucleoli can be small but conspicuous to large and prominent and may be peripheral and/or central.

As used herein "germinal centre B-cell lymphoma" or "GCB lymphoma" refers to a subtype of DLBCL wherein the lymphoma appears to arise from germinal centre B cells. Typically, GCB cells have a pattern of genetic expression that is similar to germinal center B cells and often a chromosomal translocation involving the gene bcl-2.

As used herein "activated B-Cell lymphoma" or "ABC lymphoma" refers to a subtype of DLBCL wherein the lymphoma appears to arise from postgerminal centre B cells that are arrested during plasmacytic differentiation.

The term "biomarker" as used herein can be any type of molecule corresponding to a gene listed in Table 1, or any type of molecule identified herein which can be used to distinguish samples with or without B-cell NHL or between subtypes of B-cell NHL. The term biomarker includes without limitation, a nucleic acid sequence including a gene, or corresponding RNA or cDNA, or a polypeptide, fragment thereof, or epitope that is differentially present, including differentially modified (e.g. differentially glycosylated), expressed, and/or soluble biomarkers e.g. biomarkers which are detectable in a biological fluid and which are differentially cleaved, secreted, released or shed in subjects with or without B-cell NHL. In one embodiment, detecting one or more mutations in one or more biomarkers in a sample from a subject indicates that the subject has B-cell NHL.

As used herein, the term "sample" refers to any biological fluid, cell or tissue sample from a subject which can be assayed for biomarkers (e.g. DNA, RNA and/or polypeptide products), such as soluble biomarkers in subjects having or not having B-cell NHL. Optionally, the sample comprises nucleic acids and/or proteins that have been isolated, purified or otherwise treated. For example, a sample may be fractionated (e.g. by centrifugation or using a column for size exclusion), concentrated or proteolytically processed such as trypsinized, depending on the method of testing for mutations in the biomarker employed.

The sample may be a biological fluid such as blood, serum, saliva, cerebrospinal fluid, plasma, or lymphatic fluid, a tissue sample or tissue biopsy. In one embodiment, the sample is a "tumour sample". As used herein "tumour sample" refers to a sample of cells from a subject that is undergoing uncontrolled cell division. In a preferred embodiment, the sample comprises all or part of one or more lymphoid cells, lymph nodes or a lymph node biopsy. In another preferred embodiment, the sample is a blood sample or plasma sample.

As used herein, the term "subject" refers to any member of the animal kingdom, and includes mammals such as humans. The term also includes subjects having cancer or suspected of having cancer, such as B-cell NHL. Optionally, the subject is symptomatic or asymptomatic of B-cell NHL.

As used herein the phrase "subject suspected of having B-cell non-Hodgkin lymphoma" refers to a subject for which information regarding whether or not the subject has B-cell NHL or a particular subtype of B-cell NHL is desired. Optionally, a subject suspected of having B-cell NHL may present with one or more symptoms such as: swollen, painless lymph nodes in the neck, armpits, or groin; sudden weight loss; coughing, trouble breathing, or chest pain; and/or pain or swelling in the abdomen.

As used herein "mutation" refers to a variant of biomarker that does not appear in a control sample that alters the presence, amount or biological activity of a biomarker as described herein. In one embodiment the control sample is from a subject that does not have B-cell NHL or from a sample that is not undergoing uncontrolled cell division. In one embodiment, the control sample is from the same subject as the test subject but is taken at a different point in time. In one embodiment, the mutation is a variant of the wild-type nucleic acid sequence or polypeptide sequence for that biomarker. In one embodiment, the mutation is a nonsense mutation, non-synonymous mutation, insertion or deletion. In one embodiment, the mutation is not known prior to testing the sample for a mutation. In one embodiment, the mutation is a coding Single Nucleotide Variant (cSNV). In one embodiment, the mutation is a copy number variant (CNV) or loss of heterozygozity (LOH). As used herein, the term "somatic mutation" refers to a mutation that is acquired after the formation of a zygote and is not found in the majority of cells in a subject. Examples of mutations include those listed herein in Tables 3, 5, 6, 7 and 9.

As used herein "testing a sample from the subject for a mutation" refers to analyzing the sample to determine the presence or absence of a mutation in a biomarker. In one embodiment, testing the sample for a mutation involves sequencing nucleic acid molecules that encode the biomarker or part of the biomarker. In another embodiment, testing the sample for a mutation involves detecting a mutant polypeptide such as by protein sequencing, use of selective antibodies, or the use of mass spectrometry based genotyping assays.

As used herein, "classifying a subject as having germinal centre B-cell lymphoma" refers to identifying the subject as being more likely to have germinal centre B-cell lymphoma than other types of B-cell NHL. In one embodiment, a subject classified as having GCB lymphoma is excluded from having ABC lymphoma.

As used herein, "classifying a subject as having activated B-cell lymphoma" refers to identifying the subject as being more likely to have Activated B-cell lymphoma than other types of B-cell NHL. In one embodiment, a subject classified as having ACB lymphoma is excluded from having GCB lymphoma.

As used herein "selecting a treatment" refers to determining a course of therapeutic action for a subject from a plurality of possible treatment options. For example, "selecting a treatment" may comprise selecting a specific pharmaceutical agent for administration to a subject with B-cell NHL in need thereof, as opposed to another pharmaceutical agent which may be ineffective for a particular subtype of B-cell NHL. Clinical trials that test the selective activity of therapies in ABC DLBCL are ongoing. These include the utility of drugs that reduce the activity of the transcription factor NFkB, thus reducing expression of NFkB target genes. Such drugs include Bortezomib and Lenalidomide [100; 101].

As used herein, "monitoring a subject with B-cell non Hodgkin lymphoma" refers to ascertaining the progression or remission of the B-cell NHL in a subject over time.

II. Methods

Methods for Identifying B-Cell NHLs

The present disclosure pertains to methods for detecting B-cell NHLs using biomarkers that have been shown to be mutated in samples from subjects with B-Cell NHL. As set out in Example 1, the biomarkers identified in Table 1 have been shown to be mutated in at least 2 or more cases of NHL and furthermore exhibit evidence for positive selection with either selective pressure for acquiring non-synonymous point mutations or truncating/nonsense mutations.

Accordingly, in one embodiment, there is provided a method of identifying a subject as having B-cell non-Hodgkin lymphoma comprising testing a sample from the subject for a mutation in one or more biomarkers listed in Table 1. A variety of methods known in the art may be used to test the sample to identify mutations in the biomarkers. For example, mutations may be detected in a nucleic acid molecule such as genomic DNA or mRNA. Alternatively, mutations may be detected in a polypeptide that corresponds to a biomarker listed in Table 1. In one embodiment, the mutation is listed in Tables 3, 5, 6, 7 or 9. In a preferred embodiment, the sample is tested for mutations by sequencing DNA coding for the biomarker. Optionally, the method involves amplifying the nucleic acid coding for the biomarker using PCR.

Various methods or techniques for identifying mutations in nucleic acid molecules that known in the art may be used in order to detect mutations in the biomarkers described herein. For example, embodiments include, but are not limited to, techniques such as primer extension, classical microarrays, sequencing or line probes. Methods of PCR product endpoint detection including, but not limited to, fluorescence, chemiluminescence, colourimetric techniques or measurement of redox potential may also be used with the embodiments described herein for detecting mutations in nucleic acid sequences. Optionally, the relative or absolute amount of a nucleic acid molecule corresponding to a biomarker is determined and compared to a control sample.

In another embodiment, various methods or techniques for identifying mutations in polypeptides that are known in the art may be used in order to detect mutations in the biomarkers described herein. For example, methods useful for detecting a mutation in a polypeptide corresponding to a biomarker as described herein, include mass spectrometry approaches, such as multiple reaction monitoring (MRM) and product-ion monitoring (PIM), and immunoassays such as Western blots, enzyme-linked immunosorbant assays (ELISA), and immunoprecipitation followed by sodium-dodecyl sulfate polyacrylamide gel electrophoresis (SDS-PAGE) immunocytochemistry and protein sequencing methods.

In one embodiment, antibodies or antibody fragments are used to detect a polypeptide of one or more biomarkers of the disclosure or the mutated forms a polypeptide of one or more biomarkers of the disclosure. Antibodies having specificity for a specific polypeptide, or a specific mutated polypeptide, such as the protein product of a biomarker gene of the disclosure, may be prepared by conventional methods. In an embodiment, the antibody or antibody fragment is labeled with a detectable marker. In a further embodiment, the antibody or antibody fragment is, or is derived from, a monoclonal antibody. A person skilled in the art will be familiar with the procedure for detecting the a polypeptide biomarker by using said antibodies or antibody fragments, for example, by contacting the sample from the subject with an antibody or antibody fragment labeled with a detectable marker, wherein said antibody or antibody fragment forms a complex with the biomarker. Optionally, the relative or absolute amount of a polypeptide corresponding to a biomarker is determined and compared to a control sample.

In one embodiment, the sample is from a subject having, or suspected of having, B-cell non-Hodgkin lymphoma. For example, in one embodiment the sample is a tumour sample from a subject with lymphoma. In one embodiment, the sample is a tumour biopsy of lymphoid tissue.

In one embodiment, the method comprises testing the sample for mutations in one or more biomarkers listed in Table 1. In one embodiment, the method comprises testing the sample for a plurality of the biomarkers listed in Table 1. For example, 2, 3, 4, 5, 6, 7, 8, 9, 10, 11, 12, 13, 14, 15, or 15 or more of the biomarkers may be tested for mutations.

In one embodiment the method comprises testing one or more histone modifying genes. For example, in one embodiment the method comprises testing one or more of MLL2, MEF2B, CREBBP, EP300, EZH2 or H3K27. In one embodiment, the method comprises testing one or more of FOX01, CCND3, BTG2 and B2M. In one embodiment, the method comprises testing one or more of BTG1, GNA13, SGK1, MLL2 and MEF2B. In one embodiment, the method comprises testing one or more of EZH2, TNFRS14, CREBP, BCL10, BTG1, GNA13, SGK1, MLL2 and MEF2B.

Methods for Classifying B-Cell NHLs

In another aspect of the disclosure there is provided a method of classifying a subject suspected of having, or having, B-cell non-Hodgkin lymphoma (NHL) comprising testing the sample for a mutation in one or more biomarkers selected from MEF2B, SGK1, GNA13, and TNFRS14. In one embodiment, samples that have a mutation in MEF2B, SGK1, GNA13, or TNFRS14 are classified as having germinal centre B-cell (GCB) diffuse large B cell lymphoma (DLBCL). Optionally, the method further comprises testing the sample for mutations in additional genes known to be mutated in GCB such as BCL2, TP53 or EZH2. Optionally, the method comprises testing the sample for mutations in one or more the biomarkers listed in Table 1. Optionally, the method comprises testing the sample for one or more of the mutations listed in Tables 3, 5, 6, 7 or 9.

In another embodiment, there is provided a method of classifying a subject having, or suspected of having, B-cell non-Hodgkin lymphoma (NHL) comprising testing a sample from the subject for a mutation in MYD88 or CD79B. In one embodiment, samples that have a mutation in MYD88 or CD79B are classified as having activated B-cell (ABC) diffuse large B cell lymphoma. Optionally, the method comprises testing the sample for mutations in one or more the biomarkers listed in Table 1. Optionally, the method comprises screening the sample for one or more of the mutations listed in Tables 3, 5, 6, 7 or 9.

Classifying subjects with B-cell NHL into subtypes provides a more specific clinical diagnosis and facilitates selecting therapeutic treatment options for patients. In one embodiment, the methods described herein can be used to select a treatment for the subject based on the classification of a sample form the subject as GCB DLBCL or ABC DLBCL. For example, in one embodiment, subjects are classified as having germinal centre B-cell (GCB) diffuse large B cell lymphoma (DLBCL) and the treatment that is selected comprises administration of a histone deacetylase (HDAC) inhibitor-class drugs.

In another embodiment, the methods described herein can be used to monitor a subject with B-cell NHL. For example, in one embodiment the biomarkers described herein can be used to test a first sample from a subject and compare the results to a second sample taken from the subject at an earlier or later time point. In one embodiment, an increase in the number of mutations in the biomarkers described herein overtime indicates a progression or worsening of the disease in the subject. In one embodiment, a reduction in the number of mutations in the biomarkers described herein overtime indicates an improvement or remission of the disease in the subject. Optionally, one or more of the biomarkers listed in Table 1, or any combination thereof, can be tested in the methods for identifying, classifying or monitoring a subject as described herein.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Sequences associated with accession numbers or other identifiers described herein including for example the Tables and Figures, are herein specifically incorporated by reference.

The following non-limiting example is illustrative of the present disclosure:

Example 1

Identification of Recurrently Mutated Genes

The genomes or exomes of 14 NHL cases were sequenced, all with matched constitutional DNA sequenced to comparable depths. After screening for single nucleotide variants followed by subtraction of known polymorphisms and visual inspection of the sequence read alignments, 717 nonsynonymous (coding single nucleotide variants, cSNVs) affecting 651 genes were identified. Between 20 and 135 cSNVs in each of these genomes were identified. Only 25 of the 651 genes with cSNVs were represented in the cancer gene census (December, 2010 release) [14].

RNA sequencing (RNA-seq) was performed on these 14 NHL cases and an expanded set of 113 samples comprising 83 DLBCL, 12 FL and 8 B-cell NHL cases with other histologies and 10 DLBCL-derived cell lines. These data were analysed to identify novel fusion transcripts and cSNVs (FIG. 1). 240 genes were identified with at least one cSNV in a genome/exome or an RNA-seq "mutation hot spot" (below), and with cSNVs in at least three cases in total. cSNVs were selected from each of these 240 genes for re-sequencing to confirm their somatic status. Genes with previously documented mutations in lymphoma (e.g. CD79B, BCL2) were not re-sequenced. The somatic status of 543 cSNVs in 317 genes was confirmed, with 109 genes having at least two confirmed somatic mutations. A selection of these mutations is presented for biomarkers for B-cell NHL in Table 3. Of the successfully re-sequenced cSNVs predicted from the genomes, 171 (94.5%) were confirmed somatic, 7 were false calls and 3 were present in the germ line. These 109 recurrently mutated genes were significantly enriched for genes implicated in lymphocyte activation ($P=8.3\times10^{-4}$; e.g. STAT6, BCL10), lymphocyte differentiation ($P=3.5\times10^{-3}$; e.g. CARD11), and regulation of apoptosis ($P=1.9\times10^{-3}$; e.g. BTG1, BTG2). Also significantly enriched were genes linked to transcriptional regulation ($P=5.4\times10^{-4}$; e.g. TP53) and genes involved in methylation ($P=2.2\times10^{-4}$) and acetylation ($P=1.2\times10^{-2}$), including histone methyltransferase (HMT) and acetyltransferase (HAT) enzymes known previously to be mutated in lymphoma (e.g. EZH2 [13] and CREBBP [15]).

Figure 4:
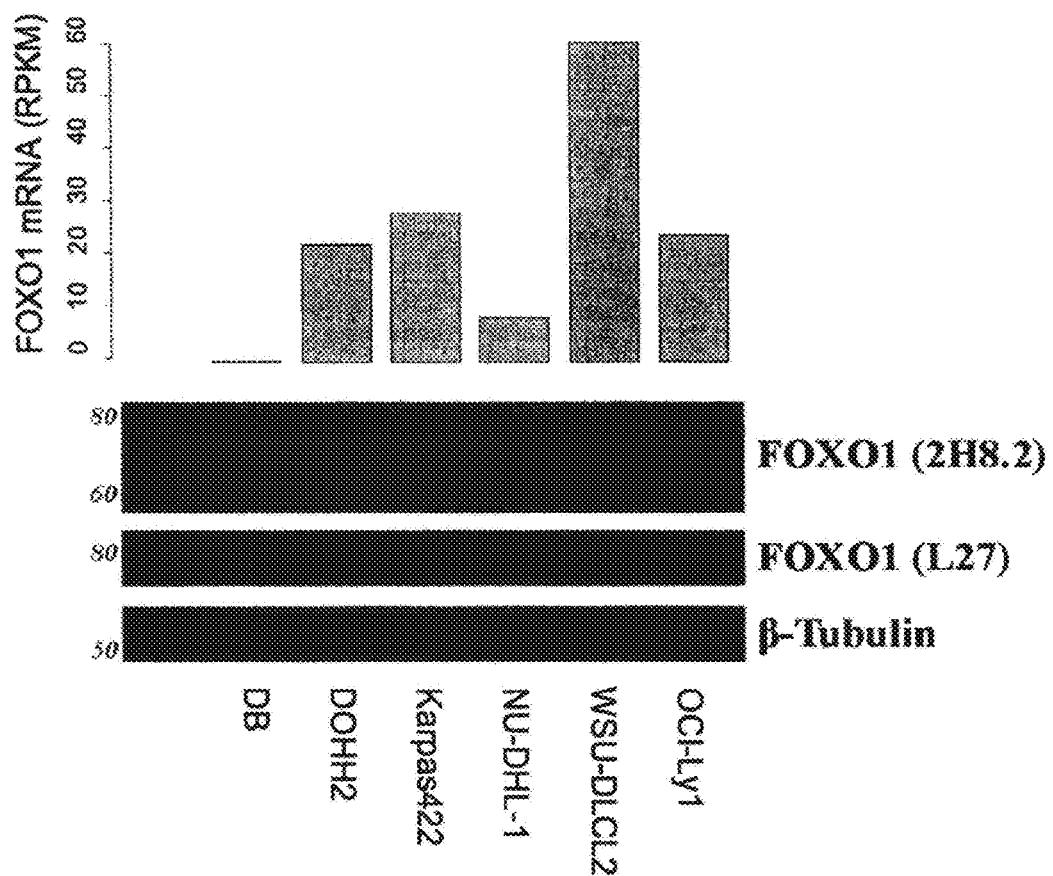
FIG. 4 shows the N-terminal truncation of FOXO1 protein with mutation affecting initial codon. (A) The RNA-seq data of cell lines and patient samples revealed mutations in 3 samples affecting the initial codon of FOXO1. To determine the effect of such mutations on FOXO1 protein, we assayed FOXO1 by Western blot in DLBCL cell lines using an antibody raised against full-length FOXO1 (2H8.2). In the cell line containing a mutation at the initiator methionine (OCI-Ly1), we observed a FOXO1 band of reduced molecular weight, compared to FOXO1 wild-type cell lines (size indicated in Kilodaltons on the left). The reduced size is consistent with the use of a second methionine codon in the FOXO1 gene, producing a protein shortened at the amino terminus by 70 amino acids. The same blot was also probed with an antibody that recognizes an N-terminal epitope (L27) and lack of a band in OCI-Ly1 cells is consistent with the notion that the lower band in this cell line corresponds to FOXO1 protein lacking its N-terminus. Absence of the protein in the DB cell line was noted, which showed significantly reduced mRNA levels as measured by RNA-seq (upper bar chart; RPKM=Reads Per Kilobase of gene model per Million mapped reads).

Mutation hot spots can result from mutations at sites under strong selective pressure and such sites have previously been identified using RNA-seq data [13]. Therefore, RNA-seq data was searched for genes with mutation hot spots, and 10 genes were identified that were not mutated in the 14 genomes (PIM1, FOXO1, CCND3, TP53, IRF4, BTG2, CD79B, BCL7A, IKZF3 and B2M), of which five (FOXO1, CCND3, BTG2, IKZF3 and B2M) were not previously known targets of point mutation in NHL (Table 4). FOXO1, BCL7A and B2M exhibited hot spots affecting their start codons. The effect of a FOXO1 start codon mutation, which was observed in three cases, was further studied using a cell line in which the initiating ATG was mutated to TTG. Western blots probed with a FOXO1 antibody revealed a band with a reduced molecular weight, indicative of a FOXO1 N-terminal truncation (FIG. 4) consistent with utilization of the next in-frame ATG for translation initiation. A second hot spot in FOXO1 at T24 was mutated in two cases. T24 is reportedly phosphorylated by AKT subsequent to B-cell receptor (BCR) stimulation [16] inducing FOXO1 nuclear export.

The RNA-seq data was analysed to determine whether any of the somatic mutations in the 109 recurrently mutated genes showed evidence for allelic imbalance with expression favouring one allele. Of 380 expressed heterozygous mutant alleles, preferential expression of the mutation was observed for 16.8% (64/380) and preferential expression of the wild-type was observed for 27.8% (106/380). Seven genes displayed evidence for significant preferential expression of the mutant allele in at least two cases: (BCL2, CARD11, CD79B, EZH2, IRF4, MEF2B and TP53). In 27 of 43 cases with BCL2 cSNVs, expression favoured the mutant allele, consistent with the previously-described hypothesis that the translocated (and hence, transcriptionally deregulated) allele of BCL2 is targeted by somatic hypermutation [17]. Examples of mutations at known oncogenic hot spot sites such as F123I in CARD11 [18] exhibited allelic imbalance favouring the mutant allele in some cases. Similarly, expression favouring two novel hot spot mutations in MEF2B (Y69 and D83) was observed and two sites in EZH2 not previously reported as mutated in lymphoma (A682G and A692V).

To distinguish new cancer-related mutations from passenger mutations, the approach proposed by Greenman et al. was used [19]. 26 genes were identified with significant evidence for positive selection (FDR 0.03, Methods), with either selective pressure for acquiring non-synonymous point mutations or truncating/nonsense mutations (Table 1). Included were known lymphoma oncogenes (BCL2, CD79B [9], CARD11 [18], MYD88 [10] and EZH2 [13]), all of which exhibited signatures indicative of selection for non-synonymous variants.

Evidence for Selection of Inactivating Changes

Figure 5:
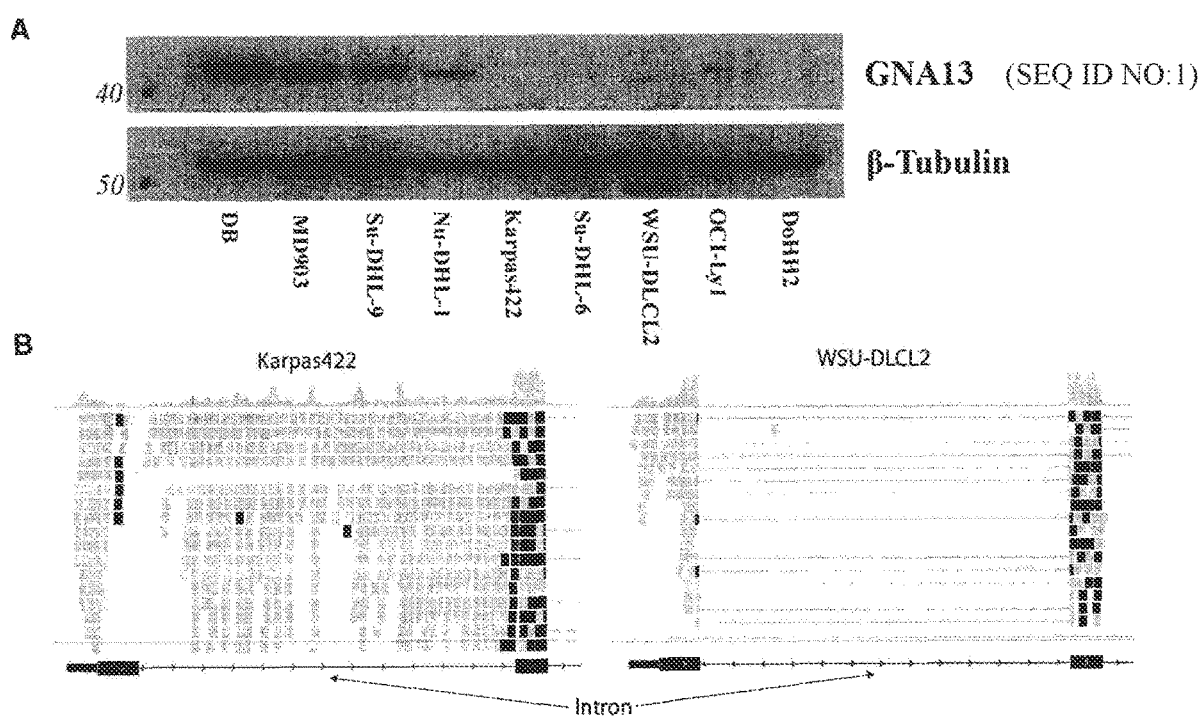
FIG. 5 shows the effect of GNA13 mutations at the protein level. (A) A western blot revealed the expected lack of GNA13 protein (SEQ ID NO: 1) in DOHH2, the cell line with a truncating point mutation detected in the RNA-seq data. The lack of protein in Karpas422, SU-DHL-6 and WSU-DLCL2 was surprising, as protein-truncating mutations were not detected in these cells. (B) Further analysis of the aligned sequence from these three cell lines and additional analysis utilizing a de-novo transcript assembly approach (Trans-ABySS; Methods), revealed multiple aberrations that may explain the lack of protein. Firstly, in Karpas422 reads were observed to map the first intron, suggesting that the intron is retained in a significant proportion of GNA13 transcripts (compare Karpas422 on the left to WSU-DLCL2 on the right). Inspection of sequence contigs from this case revealed the likely cause of intron reads to be a deletion of 87 nt that removes the canonical splicing donor from this exon (Panel C, top; SEQ ID NO: 4). Splicing still appears to occur to a lesser extent using a non-GT donor. Assembled reads from SU-DHL-6 revealed a 2 nt deletion and a large 1028 nt deletion. The former would affect the reading frame and the latter removes the terminal stop codon. Finally, in WSU-DLCL2, the splicing donor after the third exon was apparently mutated, converting the GT donor to a GC sequence (not shown). As in the Karpas422 case, there was clear evidence for retention of this intron in GNA13 transcripts in WSU-DLCL2. Intron retention has previously been linked to nonsense-mediated transcript degradation [76] and if that is the case here, could explain the lack of GNA13 protein in these cells.
Figure 5:
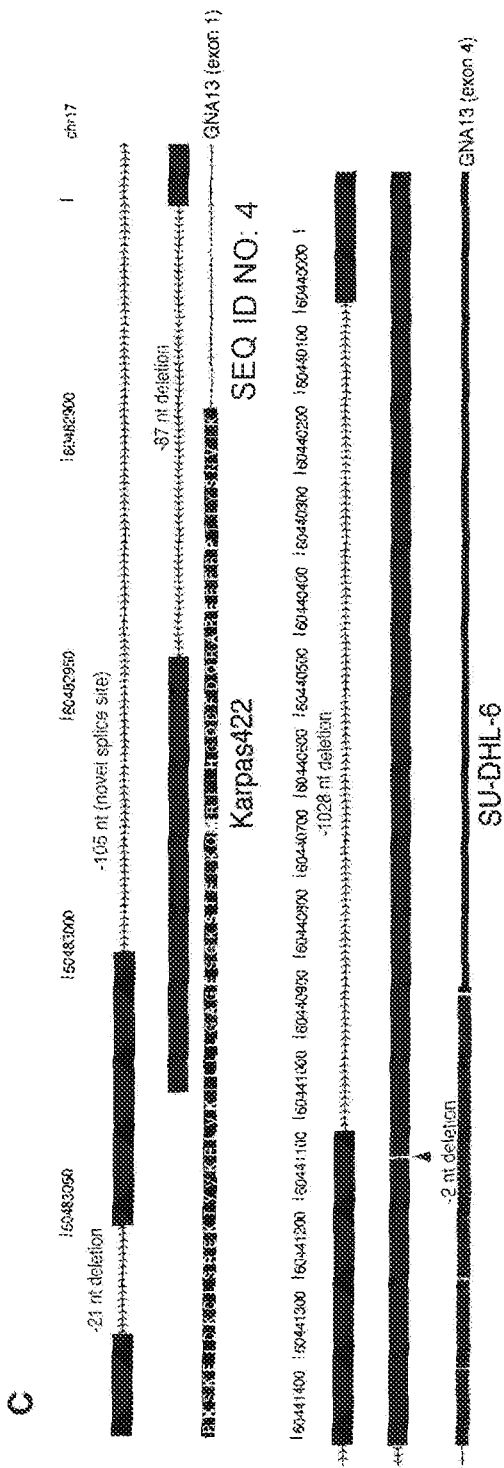

Tumour suppressor genes were expected to exhibit strong selection for the acquisition of nonsense mutations. The eight most significant genes included seven with strong selective pressure for nonsense mutations, including the known tumour suppressor genes TP53 and TNFRSF14 [20] (Table 1). CREBBP, recently reported as commonly inactivated in DLBCL [15], also showed some evidence for acquisition of nonsense mutations and cSNVs (Table 5). Enrichment was observed for nonsense mutations in BCL10, a positive regulator of NF-κB, in which oncogenic truncated products have been described in lymphomas [21]. The remaining strongly significant genes (BTG1, GNA13, SGK1 and MLL2) had no reported role in lymphoma. GNA13 was affected by mutations in 22 cases including multiple nonsense mutations. GNA13 encodes the alpha subunit of a heterotrimeric G-protein coupled receptor responsible for modulating RhoA activity [22]. Some of the mutated residues negatively impact its function [23, 24], including a T203A mutation, which also exhibited allelic imbalance favouring the mutant allele. GNA13 protein was reduced or absent on Western blots in cell lines harbouring either a nonsense mutation, a stop codon deletion, a frame shifting deletion, or changes affecting splice sites (FIG. 5).

Figure 2:
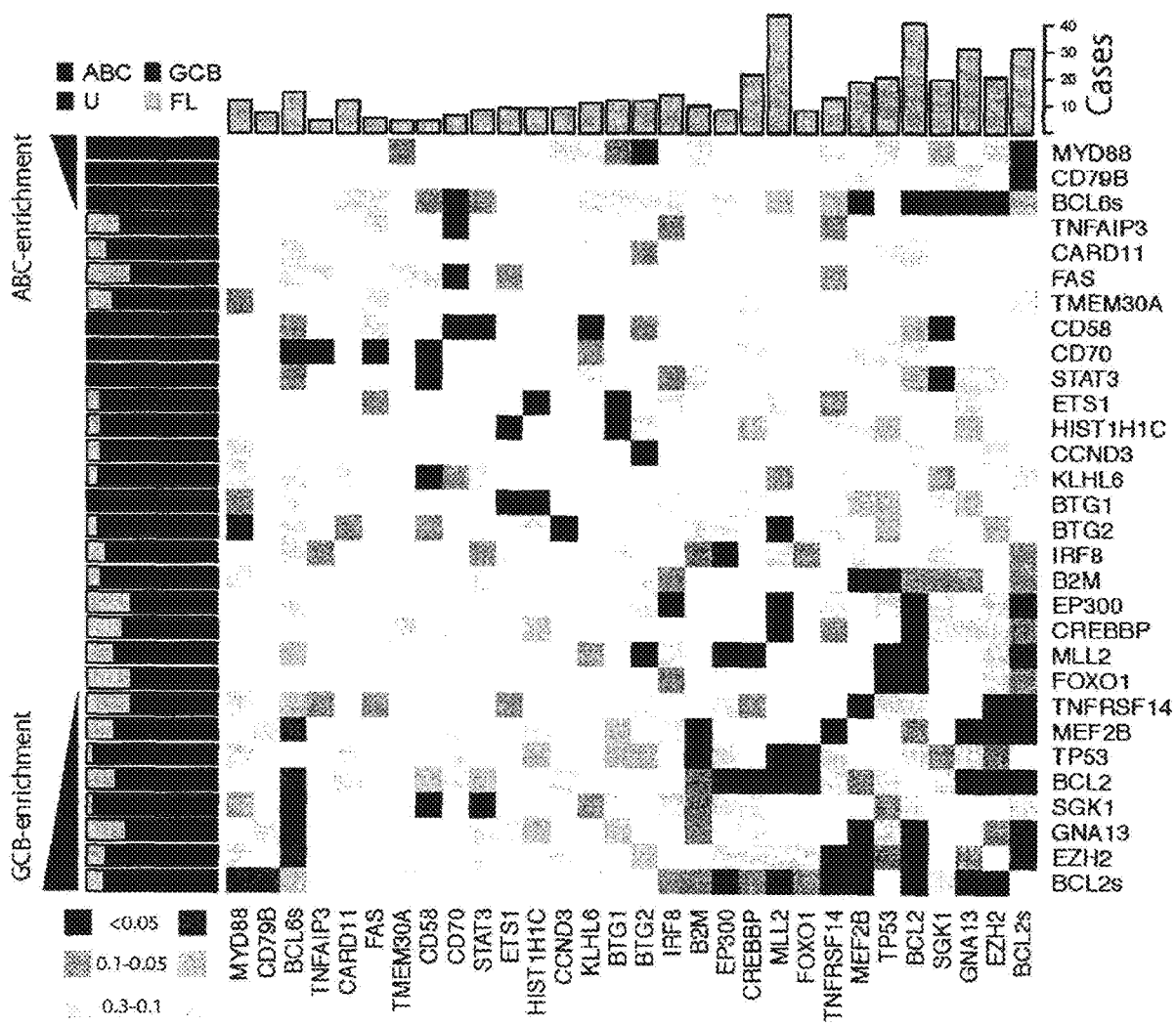
FIG. 2 shows an overview of mutations and potential cooperative interactions in NHL. This heat map displays possible trends towards co-occurrence (red) and mutual exclusion (blue) of somatic mutations and structural rearrangements. Colours were assigned by taking the minimum value of a left- and right-tailed Fisher exact test. To capture trends a P-value threshold of 0.3 was used, with the darkest shade indicating those meeting statistical significance (P<=0.05). The relative frequency of mutations in ABC (dark grey), GCB (darkest grey), unclassifiable (light grey) DLBCLs and FL (lightest grey) cases is shown on the left. Genes were arranged with those having significant (P<0.05, Fisher exact test) enrichment for mutations in ABC cases (dark grey triangle) towards the top (and left) and those with significant enrichment for mutations in GCB cases (darkest grey triangle) towards the bottom (and right). The total number of cases in which each gene contained either cSNVs or confirmed somatic mutations is shown at the top. The cluster of squares (upper-right) results from the mutual exclusion of the ABC-enriched mutations (e.g. MYD88, CD79B) from the GCB-enriched mutations (e.g. EZH2, GNA13, MEF2B, SGK1). Presence of structural rearrangements involving the two oncogenes BCL6 and BCL2 (indicated as BCL6s and BCL2s) was determined with FISH techniques utilizing break-apart probes.

SGK1 encodes a P13K-regulated kinase with functions including regulation of FOXO transcription factors [25], regulation of NF-κB by phosphorylating IκB kinase [26], and negative regulation of NOTCH signalling [27]. SGK1 also resides within a region of chromosome 6 commonly deleted in DLBCL (FIG. 1) [5]. The mechanism by which SGK1 and GNA13 inactivation may contribute to lymphoma is unclear but the strong degree of apparent selection towards their inactivation and their overall high mutation frequency (each mutated in 18 of 106 DLBCL cases) suggests that their loss contributes to B-cell NHL. Certain genes are known to be mutated more commonly in GCB DLBCLs (e.g. TP53 [28] and EZH2 [13]). Here, both SGK1 and GNA13 mutations were found only in GCB cases (P=1.93× 10−3 and 2.28×10−4, Fisher exact test, n=15 and 18, respectively) (FIG. 2). Two additional genes (MEF2B and TNFRSF14) with no previously described role in DLBCL showed a similar restriction to GCB cases (FIG. 2).

Inactivating MLL2 Mutations

MLL2 exhibited the most significant evidence for selection and the largest number of nonsense SNVs was MLL2. RNA-seq analysis indicated that 26.0% (33/127) of cases carried at least one MLL2 cSNV. To address the possibility that variable RNA-seq coverage of MLL2 failed to capture some mutations, the entire MLL2 locus (~36 kb) was PCR amplified in 89 cases (35 primary FLs, 17 DLBCL cell lines, and 37 DLBCLs). 58 of these cases were among the RNA-seq cohort. Illumina amplicon resequencing revealed 78 mutations, confirming the RNA-seq mutations in the overlapping cases and identifying 33 additional mutations. The somatic status of 46 variants was confirmed using Sanger sequencing (Table 6), and showed that 20 of the 33 additional mutations were insertions or deletions (indels). Three SNVs at splice sites were also detected, as were 10 new cSNVs that had not been detected by RNA-seq.

The somatic mutations were distributed across MLL2 (FIG. 3A). 37% (n=29/78) of these were nonsense mutations, 46% (n=36/78) were indels that altered the reading frame, 8% (n=6/78) were point mutations at splice sites and 9% (n=7/78) were non-synonymous amino acid substitutions (Table 2). Four of the somatic splice site mutations had effects on MLL2 transcript length and structure. For example, two heterozygous splice site mutations resulted in the use of a novel splice donor site and an intron retention event.

Approximately half of the NHL cases sequenced had two MLL2 mutations (Table 6). BAC clone sequencing was used in eight FL cases to show that in all eight cases the mutations were in trans, affecting both MLL2 alleles. This observation is consistent with the notion that there is a complete, or near-complete, loss of MLL2 in the tumour cells of such patients.

With the exception of two primary FL cases and two DLBCL cell lines (Pfeiffer and SU-DHL-9), the majority of MLL2 mutations appeared to be heterozygous. Analysis of Affymetrix 500k SNP array data from two FL cases with apparent homozygous mutations revealed that both tumours exhibited copy number neutral loss of heterozygosity (LOH) for the region of chromosome 12 containing MLL2 (Methods). Thus, in addition to bi-allelic mutation, LOH is a second, albeit less common mechanism by which MLL2 function is lost.

MLL2 was the most frequently mutated gene in FL, and among the most frequently mutated genes in DLBCL (FIG. 2). MLL2 mutations were confirmed in 31 of 35 FL patients (89%), in 12 of 37 DLBCL patients (32%), in 10 of 17 DLBCL cell lines (59%) and in none of the eight normal centroblast samples sequenced. The analysis predicted that the majority of the somatic mutations observed in MLL2 were inactivating (91% disrupted the reading frame or were truncating point mutations), suggesting that MLL2 is a tumour suppressor of significance in NHL.

Recurrent Point Mutations in MEF2B

Figure 3:
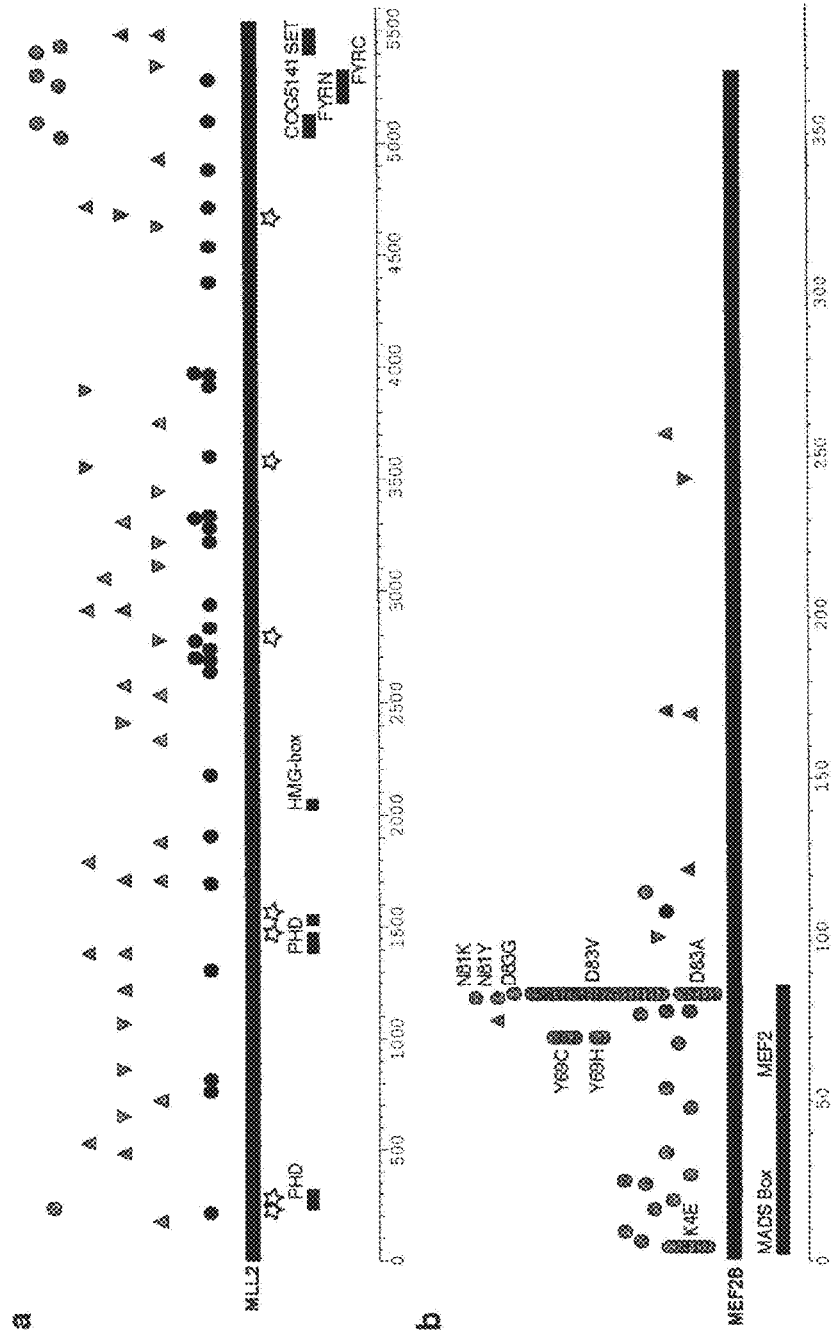
FIG. 3 shows a summary and effect of somatic mutations affecting MLL2 and MEF2B. (A) Re-sequencing the MLL2 locus in 89 samples revealed mainly nonsense (dark grey circles) and frameshift-inducing indel mutations (triangles). A smaller number of non-synonymous somatic mutations (light grey circles) and point mutations or deletions affecting splice sites (stars) were also observed. All of the non-synonymous point mutations affected a residue within either the catalytic SET domain, the FYRC domain ("FY-rich C-terminal domain") or PHD zinc finger domains. The effect of these splice site mutations on MLL2 splicing was also explored. (B) The cSNVs and somatic mutations found in MEF2B in all FL and DLBCL cases sequenced are shown with the same symbols. Only the amino acids with variants in at least two patients are labelled. cSNVs were most prevalent in the first two protein coding exons of MEF2B (exons 2 and 3). The crystal structure of MEF2 bound to EP300 supports that two of the four hot spots (N67 and Y69) are important in the interaction between these proteins [50].

Selective pressure analysis also revealed genes with stronger pressure for acquisition of amino acid substitutions than for nonsense mutations. One such gene was MEF2B, which had not previously been linked to lymphoma. 20 (15.7%) cases had MEF2B cSNVs and 4 (3.1%) cases had MEF2C cSNVs. All cSNVs detected by RNA-seq affected either the MADS box or MEF2 domains. To determine the frequency and scope of MEF2B mutations, exons 2 and 3 were Sanger-sequences in 261 primary FL samples; 259 DLBCL primary tumours; 17 cell lines; 35 cases of assorted NHL (IBL, composite FL and PBMCL); and eight non-malignant centroblast samples. A capture strategy was also used to sequence the entire MEF2B coding region in the 261 FL samples, revealing six additional variants outside exons 2 and 3. 69 cases (34 DLBCL; 12.67% and 35 FL; 15.33%) were identified with MEF2B cSNVs or indels; novel variants in other NHL and non-malignant samples were not observed. 55 (80%) of the variants affected residues within the MADS box and MEF2 domains encoded by exons 2 and 3 (Table 7; FIG. 3B). Each patient generally had a single MEF2B variant and relatively few (8 total, 10.7%) truncation-inducing SNVs or indels were observed. Non-synonymous SNVs were by far the most common type of change observed, with 59.4% of detected variants affecting K4, Y69, N81 or D83. In 12 cases MEF2B mutations were shown to be somatic, including representative mutations at each of K4, Y69, N81 and D83 (Table 8). Mutations in ABC cases were not detected, indicating that somatic mutations in MEF2B play a role unique to the development of GCB DLBCL and FL (FIG. 2).

Discussion

In this study of genome, transcriptome and exome sequences from 127 B-cell NHL cases, 109 genes were identified with clear evidence of somatic mutation in multiple individuals. Significant selection appears to act on at least 26 of these for the acquisition of either nonsense or missense mutations. The majority of these genes do not appear to have previously been associated with any cancer type. An enrichment of somatic mutations was observed affecting genes involved in transcriptional regulation and, more specifically, chromatin modification.

MLL2 emerged from the analysis as a major tumour suppressor locus in NHL. It is one of six human H3K4-specific methyltransferases in the MLL family, all of which share homology with the *Drosophila* trithorax gene [29]. Trimethylated H3K4 (H3K4me3) is an epigenetic mark associated with the promoters of actively transcribed genes. By laying down this mark, MLLs are responsible for the transcriptional regulation of developmental genes including the homeobox (Hox) gene family [30] which collectively control segment specificity and cell fate in the developing embryo [31,32]. Each MLL family member is thought to target different subsets of Hox genes [33] and in addition, MLL2 is known to regulate the transcription of a diverse set of genes [34]. Recently, MLL2 mutations were reported in a small-cell lung cancer cell line [35] and in renal carcinoma [36] but the frequency of nonsense mutations affecting MLL2 in these cancers was not established in these reports. Parsons and colleagues recently reported inactivating mutations in MLL2 or MLL3 in 16% of medulloblastoma patients [37] further implicating MLL2 as a cancer gene.

The data in this example link MLL2 somatic mutations to B-cell NHL. The reported mutations are likely to be inactivating and in eight of the cases with multiple mutations, it was confirmed that both alleles were affected, presumably resulting in essentially complete loss of MLL2 function. The high prevalence of MLL2 mutations in FL (89%) equals the frequency of the t(14;18)(q32;q21) translocation, which is considered the most prevalent genetic abnormality in FL [3]. In DLBCL tumour samples and cell lines, MLL2 mutation frequencies were 32% and 59% respectively, also exceeding the prevalence of the most frequent cytogenetic abnormalities, such as the various translocations involving 3q27, which occur in 25-30% of DLBCLs and are enriched in ABC cases [38]. Importantly, MLL2 was found mutated in both DLBCL subtypes (FIG. 2). Analyses thus indicate that MLL2 acts as a central tumour suppressor in FL and both DLBCL subtypes.

The MEF2 gene family encodes four related transcription factors that recruit histone-modifying enzymes including histone deacetylases (HDACs) and HATs in a calcium-regulated manner. Although truncating variants were detected in MEF2 gene family members, the present analysis suggests that, in contrast to MLL2, MEF2 family members tend to selectively acquire non-synonymous amino acid substitutions. In the case of MEF2B, 59.4% of all the cSNVs were found at four sites within the protein (K4, Y69, N81 and D83), and all four of these sites were confirmed to be targets of somatic mutation. 39% of the MEF2B alterations affect D83, resulting in replacement of the charged aspartate with any of alanine, glycine or valine. Although the specific the consequences of these substitutions on protein function is unknown, it seems likely that their effect would impact the ability of MEF2B to facilitate gene expression and thus play a role in promoting the malignant transformation of germinal centre B cells to lymphoma.

Figure 6:
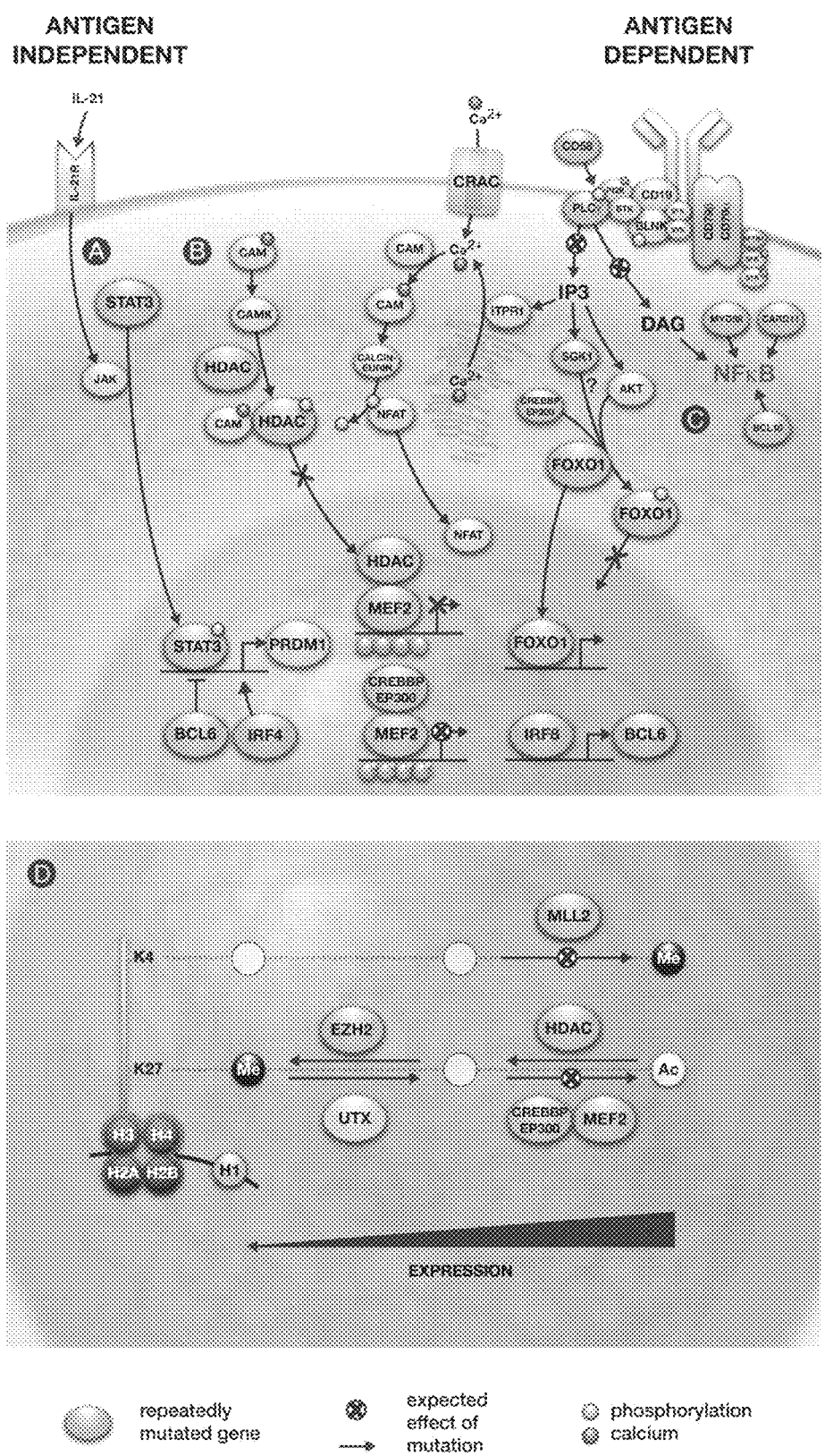
FIG. 6 shows the predicted impact of recurrently mutated genes on BCR signalling and downstream messengers. (A) Autocrine and paracrine stimulation of IL-21R induces the dimerization and activation of STAT3, a positive regulator of PRDM1 expression [77]. Mutations affecting the DNA binding domain of STAT3 are known to act as dominant negatives, which would predict the inability to induce PRDM1 expression following IL-21 stimulation. (B) Multiple mutations predicted to directly alter BCR signalling or alter the normal events subsequent to BCR-induced influx of the secondary messenger $Ca^{2+}$. Cross-linking of CD58 has been shown to result in the phosphorylation of BLNK, Syk and PLC-gamma and lead to Akt activation [78]. Various mutations are expected to alter the ability of B cells to induce the expression of MEF2 target genes in response to the $Ca^{2+}$ influx. The role of MEF2 gene family members in mediating epigenetic alterations downstream of the BCR has been inferred from a knockout study in which MEF2C was shown to be required for mediating calcium-dependent response to BCR signaling [79] and the involvement of CREBBP/EP300 in this process has been inferred from MEF2-mediated transcriptional regulation in other cell types including T cells [80]. This model predicts that influx of $Ca^{2+}$ after BCR stimulation would result in the displacement of HATs by activated Calmodulin-dependent protein kinase (CAMK), allowing HDAC activity via CREBBP/EP300 thus enabling transcription at MEF2 target loci. In this model, mutation of any of these three genes and potentially the S155F mutation in HDAC7 would diminish this effect and suppress the induction of MEF2 target loci after BCR stimulation. (C) Multiple mutations may affect the regulation of the activity of FOXO proteins following BCR stimulation. FOXO1 is a downstream target of the kinase AKT, which is activated during BCR signalling. SGK, a related kinase (mutated in B-cell NHLs as described herein), is known to phosphorylate FOXO3a in a similar way [25] and the present applicants predict it to also phosphorylate FOXO1. Thus, mutations affecting the FOXO1 phosphorylation site or SGK1 could affect the regulation of FOXO1 nuclear localization and hence, its transactivation activity. The shortened FOXO1 protein produced by mutation of the initial codon (FIG. 4) would not contain this phosphorylation site and hence those mutations may also result in altered subcellular localization. Various mutations affecting NF-κB activity, which have been previously described, were also observed here [9-10, 18, 21]. (D) Many of the recurrently mutated genes in B-NHL are involved in histone modification or themselves encode histone proteins (i.e. HIST1H1C, one of multiple genes that encode histone protein H1). CREBBP/EP300 and MLL2 each produce activating chromatin marks (H3K27Ac and H3K4me3, respectively). HDAC (e.g. HDAC7) and EZH2 produce inactivating marks by removing acetyl groups and trimethylating H3K27, respectively. As heterozygous EZH2 Y641 mutations are known to effectively enhance PRC2 activity [43], then each of the individual mutations may result in suppression of gene expression. It have not been confirmed whether EZH2 and MLL2 regulate the expression of the same genes as MEF2B/CREBBP/EP300.

MEF2B mutations can be linked to CREBBP and EP300 mutations, and to recurrent Y641 mutations in EZH2 [13]. One target of CREBBP/EP300 HAT activity is H3K27, which is methylated by EZH2 to repress transcription. There is evidence that the action of EZH2 antagonizes that of CREBBP/EP300 [39]. One function of MEF2 is to recruit either HDACs or CREBBP/EP300 to target genes [40], and it has been suggested that HDACs compete with CREBBP/EP300 for the same binding site on MEF2 [41]. Under normal $Ca^{2+}$ levels, MEF2 is bound by type IIa HDACs, which maintain the tails of histone proteins in a deacetylated repressive chromatin state [42]. Increased cytoplasmic $Ca^{2+}$ levels induce the nuclear export of HDACs, enabling the recruitment of HATs such as CREBBP/EP300, facilitating transcription at MEF2 target genes. Mutation of CREBBP, EP300 or MEF2B may impact expression of MEF2 target genes owing to reduced acetylation of nucleosomes near these genes (FIG. 6). In light of the recent finding that heterozygous EZH2 Y641 mutations enhance overall H3K27 trimethylation activity of PCR2 [43, 44], it is possible that mutation of both MLL2 and EZH2 could cooperate in reducing the expression of some of the same target genes. The data in this example show that (1) post-transcriptional modification of histones is of key importance in germinal centre B cells and (2) deregulated histone modification due to these mutations likely results in reduced acetylation and enhanced methylation and acts as a core driver event in the development of NHL (FIG. 6).

It is thought that GCB and ABC DLBCLs arise due to distinct genetic events [5] and it is widely accepted that the aggressive nature of the latter results from the acquisition of mutations that mimic stimulation of the B cell receptor by antigen or those that more directly induce constitutive activation of NF-κB [2]. This example provides other important modulators or components of BCR signalling and regulators of B cell differentiation or survival as targets of repeated and recurrent mutation, including MEF2B/C [79], SGK [5], IRF4 [82], STAT3 [77], STAT6 [83], RFTN1 [84], CCND3 [85], PLCG2, FOXO1 [86], CARD11 [18], CD79B [9] and MYD88 [10] and IKZF3 [87]. There were notable differences in mutation patterns among these genes. For example, MEF2B/C and STAT3, each of which function as dimers, showed strong evidence for selectively acquiring nonsynonymous (rather than truncating) mutations, whereas SGK1 and CCND3 appeared to be preferentially truncated in NHL. The previously characterized CARD11 [18], CD79B [9] and MYD88 [10] all act upstream of NF-κB, leading to its deregulation, typically in ABC DLBCLs. In the present Example, only CD79B and MYD88 (in addition to structural rearrangements involving BCL6) showed a significant enrichment for mutations in ABC cases (FIG. 2) and the point mutations observed largely corresponded to the known hot spots in these two genes [9, 10] (Table 4).

The remaining genes listed above encode proteins that are either activated or inhibited as a result of BCR stimulation, but not directly involved in regulating NF-κB. PRDM1 has been termed the plasma cell master differentiation gene as it orchestrates terminal differentiation of germinal centre B cells into plasma cells [88]. Importantly STAT3 [77], found here to be commonly mutated in DLBCL, regulates the activity or expression of PRDM1 in response to IL-21 stimulation. Of interest, inherited mutations in STAT3 are the primary cause of an immune disorder known as hyper IgE syndrome and it has been shown that in these cases mutant STAT3 acts in a dominant negative manner [89]. Strikingly, some of the somatic mutations reported here affect the same residues found mutated in the constitutional DNA of hyper IgE patients. This leads to a prediction that mutant cells may be unable to induce PRDM1 transcription following IL-21 stimulation (FIG. 6A). In particular, as many of these mutations were found in both GCB DLBCL and FL, the data suggests that malignant transformation of germinal centre B cells relies on components of BCR signalling separate from those utilized in ABC DLBCL (i.e. NF-κB) but also that altered regulation of PRDM1, previously thought to be a feature unique to ABC DLBCL, may be of general importance in NHL.

Mutations affecting CREBBP and EP300 were recently reported in DLBCL [15], and ALL [90]. Similar to the observations reported in these studies, the data shows a preference for accumulation of truncating SNVs (n=4, 16.7% of mutated cases) but also include non-synonymous SNVs in many cases (20 cases with cSNVs, Table 5). EP300 also contained multiple cSNVs (8 cases total). 3 EP300 cSNVs and 9 CREBBP cSNVs were confirmed as somatic mutations. Cases with multiple cSNVs in either gene were rarely observed (one cell line and three patients) consistent with the commonly held notion that both genes are haplo-insufficient [91]. The cSNVs that were not predicted to result in protein truncation were mainly found within the HAT domain of these two proteins. These included four codons that are apparent mutation hot spots (Tables 4 and 5). Of these, three correspond to residues that have been reported to be homologous between the two proteins [75] (Table 5). Representative cSNVs corresponding to three of these hot spots in CREBBP and one in EP300 were confirmed as somatic. Three of the EP300 somatic non-synonymous mutations observed affected residues previously shown to reduce acetyltransferase activity in an in vitro acetyltransferase assay[75]. CREBBP (but not EP300) was confirmed to have a significant signature of selective pressure to acquire both truncating and missense mutations (Table 1), but the lack of significance for the latter may owe to limited statistical power due to its reduced mutation prevalence relative to CREBBP. Taken together, these data suggest that reduction or loss of either CREBBP or EP300 may promote lymphomagenesis. Of note, in contrast to a recent report [15], a significant difference was not observed in CREBBP or EP300 mutation frequency in the two subtypes (P=0.5656 for CREBBP and 0.6607 for EP300; Fisher exact test).

MEF2 proteins can act as transcriptional co-activators or co-repressors by recruiting two classes of enzymes that alter the acetylation state of histone tails, namely HATs and HDACs. MEF2 dimers are known to associate with the two HATs CREBBP and EP300 [30] and it has been suggested that HDACs and CREBBP/EP300 compete for the same binding site on MEF2 [41]. Under normal levels of intracellular $Ca^{2+}$, MEF2 is bound by one of several type IIa HDACs, which maintain the tails of histone proteins in a deacetylated repressive chromatin state [42]. Increased cytoplasmic $Ca^{2+}$ levels induce the nuclear export of the bound HDAC, thus enabling MEF2 dimers to recruit a HAT enzyme such as CREBBP/EP300, which facilitate transcription at MEF2 target genes by catalysing the addition of acetyl groups to the tails of core histone proteins including lysine 27 on histone H3 (H3K27) [40, 41] (FIG. 6D).

$Ca^{2+}$-mediated induction of MEF2 target genes is utilised in diverse developmental processes including muscle and neuronal cell differentiation [92] as well as the maturation of B and T cells [80]. For example, during negative selection, upon T-cell-receptor (TCR) stimulation, the resulting $Ca^{2+}$ influx results in MEF2-mediated induction of the pro-apoptosis NR4A1 (NUR77), which, in turn drives apoptosis of self-reactive T cells [80]. It has also been shown in T cells that MEF2D interacts directly with nuclear NFAT, another $Ca^{2+}$/CaM-regulated protein, and recruits EP300 to MEF2 target genes [93]. In murine B cells, it was recently demonstrated that MEF2C is required to mediate gene expression events following BCR stimulation, but this study did not discuss a possible overlapping role of MEF2B in this process nor was there a conclusive identification of the MEF2C-regulated genes important to this process [79]. That mutations in MEF2C were also observed at a lower frequency in NHL samples supports the interpretation that these proteins share a related function in this cellular context. The MEF2B dimer has previously been co-crystallized with three of its interacting partners, namely Cabin1 [81], HDAC9 [41] and EP300 [50] and, informed by these structures, one could predict that many of the recurrent mutations would negatively impact the function of MEF2B. For example, at least three of the mutated residues (K5, K23 and R24) are required for mediating the binding of MEF2 to DNA [94]. Because MEF2 proteins can heterodimerize [95], mutations that impact the function of MEF2 are known to produce a dominant effect on the overall function of any MEF2-family protein by occupying a significant proportion of MEF2-containing complexes [96]. In fact one of the residues found mutated in this study (K24) was previously demonstrated to act as a dominant negative when ectopically expressed [96]. Further, the mutation hot spot Y69 was recently shown to be involved in multiple interactions in a solved crystal structure of MEF2B bound to EP300 [50], suggesting the possibility that this mutation may impact the ability of these two proteins to interact. Although the impact of the individual MEF2B mutations on MEF2 function requires further study, the recurrence of these mutations among a limited set of residues suggests the action of positive selection for these mutations during cancer progression.

When one considers the high frequency of mutations detected that affect genes encoding MEF2 proteins, it is striking that inactivating mutations affecting both CREBBP and EP300 are common in NHL, as these are both known effectors of the induction of MEF2-regulated genes. Notably, with one exception, all of the truncation-inducing mutations identified in CREBBP and EP300 are predicted to remove the histone acetyltransferase (HAT) domain of the protein [81]. Moreover, comparison of the positions mutated in CREBBP to those mutated in EP300 reveals that some homologous residues within the HAT domains are affected in both proteins. Based on the crystal structure of EP300, five of these recurrently mutated residues were previously identified as important for mediating substrate interaction [75]. In that study, three of these residues were mutated and showed loss (or reduction) of HAT activity in vitro, suggesting that many of the cSNVs observed in these two proteins also negatively impact their function in vivo. Further, CREBBP/EP300 are both known to regulate the function of FOXO1 [97], another gene found recurrently mutated in this study. Thus it is also possible that the mutation of these genes in addition their potential effect on MEF2-mediated transactivation, could impact the normal AKT-mediated nuclear exclusion of FOXO1 (FIG. 6C).

The data presented herein is consistent with a model wherein the induction of MEF2 target genes in response to BCR stimulation is inhibited by mutations that reduce the function of MEF2 complexes, potentially in a dominant negative fashion, or mutations that inactivate either of their transcriptional co-activators CREBBP or EP300 (FIG. 6D). Another mutation identified herein in a single case is also consistent with this model, namely the mutation of S155 to phenylalanine in HDAC7. This serine residue is known to be phosphorylated by CAMK following TCR stimulation, facilitating nuclear export of HDAC7 in response to $Ca^{2+}$ influx [98]. In the cited study, mutation of this residue resulted in impaired export of HDAC7 following TCR stimulation thereby inhibiting MEF2-mediated induction of NUR77 expression and hence, inhibiting NUR77-mediated apoptosis. Thus, this mutant could potentially produce a nuclear-restricted protein that leads to constitutive suppression of MEF2 target genes regardless of intracellular $Ca^{2+}$ levels. This would be a similar effect that would be expected for loss-of-function mutations of MEF2B, CREBBP or EP300. Though an increase in cytoplasmic $Ca^{2+}$ is one downstream signal following BCR stimulation, the NFAT transcription factors, key downstream mediators of this signal that promote survival, were not mutated and thus are expected to function normally. Also, pathways such as NF-κB and events modulated by AKT do not rely on the $Ca^{2+}$ messenger and should therefore be unaffected by these mutations. Interestingly, a recent report suggests that SGK1 (found here to be commonly inactivated in DLBCL) may also play a role in modulating $Ca^{2+}$ levels by regulating the turnover of the $Ca^{2+}$ channel protein Orai [99]. Thus, this model predicts that mutations directly affecting MEF2 function (i.e. those in MEF2B, MEF2C, HDAC7, CREBBP or EP300) or other genes involved in regulating cytoplasmic calcium levels would diminish the cell's ability to induce MEF2 target genes in response to BCR stimulation while leaving other downstream signals intact.

Methods

Sample Acquisition

Lymphoma samples were classified by an expert haematopathologist (R.D.G) according to the World Health Organization criteria of 2008. Benign specimens included reactive pediatric tonsils or purified CD77-positive centroblasts sorted from reactive tonsils using Miltenyi magnetic beads (Miltenyi Biotec, CA). The tumour specimens were collected as part of a research project approved by the University of British Columbia-British Columbia Cancer Agency Research Ethics Board (BCCA REB) and are in accordance with the Declaration of Helsinki.

For all DLBCL samples profiled by RNA-seq, genome or exome sequencing in this study, tumour content was greater than 50% as assessed by: a) immunophenotyping using flow cytometry to detect the level of coexpression of CD19 and light chain restriction, or b) a pathologist review of an H&E-stained frozen section taken adjacent to the tissue that was cut and used for nucleic acid extraction. All other specimens used in this study were obtained at the time of diagnosis and were derived from archived fresh-frozen tissue or frozen tumour cell suspensions. Constitutional DNA was obtained from peripheral blood or from B cell-negative sorted tumour cell suspensions (fraction eluted from cells captured by B Cell Isolation Kit II or CD19 MicroBeads (Miltenyi Biotec, CA)).

Cell Lines

DB [51], DOHH-2 [52], Karpas422 [53], NU-DHL-1 [54], NU-DUL-1 [55], SU-DHL-6 and WSU-DLCL2 [56] are cell lines obtained from DSMZ. Pfeiffer and Toledo were obtained from ATCC and all OCI-Ly [57] lines (1, 3, 7, 10 and 19) were obtained from Louis Staudt (US National Institutes of Health). The cell lines MD903, SU-DHL-9 and RIVA were obtained from Martin Dyer (University of Leicester, UK).

Preparation and Sequencing of RNA-Seq, Genome and Exon Capture Illumina Libraries Genomic DNA for construction of genome and exome libraries was prepared from biopsy materials using the Qiagen AllPrep DNA/RNA Mini Kit (Qiagen). DNA quality was assessed by spectrophotometry (260 nm/280 nm and 260 nm/230 nm absorption ratios) and gel electrophoresis before library construction. DNA was sheared for 10 minutes using a Sonic Dismembrator 550 with a power setting of "7" in pulses of 30 seconds interspersed with 30 seconds of cooling (Cup Horn, Fisher Scientific) and then analysed on 8% PAGE gels. The 200 to 300 bp DNA size fraction was excised and eluted from the gel slice overnight at 4° C. in 300 µL of elution buffer (5:1 (vol/vol) LoTE buffer (3 mM Tris-HCl, pH 7.5, 0.2 mM EDTA)/7.5 M ammonium acetate) and was purified using a Spin-X Filter Tube (Fisher Scientific) and ethanol precipitation. Genome libraries were prepared using a modified paired-end protocol supplied by Illumina Inc. This involved DNA end-repair and formation of 3' adenosine overhangs using the Klenow fragment of DNA polymerase I (3'-5' exonuclease minus) and ligation to Illumina PE adapters (with 5' overhangs). Adapter-ligated products were purified on QIAQUICK® spin columns (Qiagen) and PCR-amplified using PHUSION® DNA polymerase (NEB) and ten cycles with the PE primer 1.0 and 2.0 (Illumina). PCR products of the desired size range were purified from adapter ligation artifacts using 8% PAGE gels. DNA quality was assessed and quantified using an Agilent DNA 1000 series II assay (Agilent) and Nanodrop 7500 spectrophotometer (Nanodrop), and DNA was subsequently diluted to 10 nM. The final concentration was confirmed using a QUANT-IT™ dsDNA HS assay kit and Qubit fluorometer (Invitrogen).

For genomic DNA sequencing, clusters were generated on the Illumina cluster stations using v1 cluster reagents. Paired-end reads were generated using v3 sequencing reagents on the Illumina GAIIx platform following the manufacturer's instructions. Image analysis, base-calling and error calibration were performed using v1.0 of Illumina's Genome analysis pipeline. The DLBCL genomes were sequenced with 100 nucleotide paired-end reads using the HiSeq2000 platform. For RNA-seq analysis, a modified method was used similar to the protocol previously described [13]. Briefly, RNA was extracted from 15×20 µm sections cut from fresh-frozen lymph node biopsies using the MACS mRNA isolation kit (Miltenyi Biotec), from 5-10 µg of DNase I-treated total RNA as per the manufacturer's instructions. Double-stranded cDNA was synthesized from the purified poly(A)$^+$ RNA using the SUPERSCRIPT® Double-Stranded cDNA Synthesis kit (Invitrogen) and random hexamer primers (Invitrogen) at a concentration of 5 µM. The cDNA was fragmented by sonication and a paired-end sequencing library prepared following the Illumina paired-end library preparation protocol (Illumina).

For exome sequencing, genomic DNA was extracted following the protocol supplied in the Qiagen AllPrep DNA/RNA Mini Kit (Cat #80204), and quantified using a QUANT-IT™ dsDNA HS assay kit and a Qubit fluorometer (Invitrogen). Approximately 500 ng DNA was sheared for 75 seconds at duty cycle "20%" and intensity of "5" using a Covaris E210, and run on an 8% PAGE gel. A 200 to 250 bp DNA size fraction was excised and eluted from the gel slice, and was ligated to Illumina paired-end adapters following a standard protocol as previously described [13]. The adapter ligated DNA was amplified for 10 cycles using the PE primer set (Illumina) and purified as a pre-exome capture library. The DNA was assessed using an Agilent DNA 1000 Series II assay, and 500 ng DNA was hybridized to the 38 Mb Human exon probe using the All Exon Kit (Cat #G3362) following the Agilent SureSelect Paired-End Target Enrichment System Protocol (Version 1.0, September 2009). The captured DNA was purified using a Qiagen MinElute column, and amplified for 12 cycles using PE primer set. The PCR products were run on an 8% PAGE gel, the desired size range (320 to 370 bp) was excised and purified, and was then assessed using an Agilent DNA 1000 series II assay and diluted to 10 nM. The final library DNA concentration was confirmed using a QUANT-IT™ dsDNA HS assay kit and Qubit fluorometer. Clusters were generated on the Illumina cluster station and paired-end reads generated using an Illumina Genome Analyzer ($GA_{IIx}$) following the manufacturer's instructions.

Alignment-Based Analysis of Tumour DNA and RNA Sequence for Somatic Point Mutations All reads were aligned to the human reference genome (hg18) or (for RNA-seq) to a genome file that was augmented with a set of all exon-exon junction sequences using BWA version 0.5.4 [46]. RNA-seq libraries were aligned with an in-house modified version of BWA that is aware of exon junction reads and considers them when determining pairing distance in the "sampe" (read pairing) phase of alignment. Candidate single-nucleotide variants (SNVs) were identified in the aligned genomic sequence reads and the transcriptome (RNA-seq) reads using an approach similar to one we previously described [13]. One key difference in the variant calling in this study was the application of a Bayesian SNV identification algorithm ('SNVmix') [47]. This approach is able to identify SNVs with a minimum coverage of two high-quality (Q20) bases. SNVs were retained if they had a SNVmix probability of at least 0.99 and had support from reads mapping to both genomic strands. Any SNV near gapped alignments or exactly overlapping sites assessed as being polymorphisms (SNPs) were disregarded, including variants matching a position in dbSNP or the sequenced personal genomes of Venter [58], Watson [59] or the anonymous Asian [60] and Yoruban [61] individuals. For paired samples with matched constitutional DNA sequence, all variants with evidence (a SNVmix probability of at least 0.99 and 2 or more high quality base calls matching the SNV) in the constitutional DNA were considered germline variants and were no longer considered cSNVs. Mutations were annotated on genes using the Ensembl transcripts (version 54), except in the cases of MEF2B and MLL2, for which the Ensembl annotations were deemed inferior to the Refseq. Because situations were observed where exons were represented in Ensembl transcripts that were not also represented in a Refseq, candidate mutations are only reported in exons shared by both annotations (e.g. in Supplementary Table S4). Candidate mutations were subsequently reviewed visually in the integrative genomics viewer (IGV) [62] and those appearing to be artefacts or with some evidence (2 or more reads) visible in the constitutional DNA sequence were removed.

Validation of Candidate Somatic Mutations Using Illumina Sequencing

Validation was accomplished by designing primers to amplify a 200 to 300 bp region around the targeted variant with one primer within reach of a single read (i.e. maintaining the sum of the primer length and distance to variant less than 100 bp, depending on read length used). Amplicons were generated for both tumour and normal DNA. Two pools of amplicons were generated, one for tumour and one for normal DNA, with equal volumes from each PCR reaction (or increased volume for amplicons that resulted in faint bands in an agarose gel) and an Illumina paired-end sequencing library was constructed from the pool. For variants common to more than one patient, a 6 nt index, which was added to the 5' end of each primer, was assigned for each patient. These index sequences were trimmed from sequence reads prior to alignment and subsequently used to associate the data with individual patients. Reads were aligned using BWA and variants were visually confirmed for validity and somatic status in IGV [63](absence from constitutional DNA). Variants with primer design or PCR failures were scored as 'unvalidated'.

Validation of cSNVs by Sanger Sequencing

The majority of candidate cSNVs were validated by Sanger sequencing of the region surrounding each mutation. These included all cSNVs identified in the two DLBCL exomes and the FL genome/exome (i.e. DLBCL-PatientA, DLBCL-PatientB and FL-PatientA). For the additional DLBCL genomes, cSNVs were selected for validation only if there were three or more cSNVs in that gene in the entire cohort. To do so, primers were designed to amplify 350-1200 bp regions by PCR (most amplicons were ~400 bp). Forward and reverse primers were tailed with T7 and M13Reverse 5' priming sites, respectively. PCR conditions used were 94° C. for 2 minutes, 30 cycles of 94° C. for 30 seconds, 60° C. for 30 seconds and 72° C. for 1 minute, and a final extension at 72° C. for 8 minutes. To determine the somatic or germ line origin of the mutations, mutations were re-sequenced in both tumour and constitutional DNA, the latter obtained from peripheral blood or negative-sort cells (see section entitled Sample Acquisition). The sequencing reactions consisted of 50 cycles of 96° C. for 10 seconds, 43° C. (for M13Reverse) or 48° C. (T7) for 5 seconds and 60° C. for 4 minutes and were analysed using an AB 3730XL. All capillary traces were analysed using the Staden Package [64] and all somatic variants were visually inspected to confirm their presence in tumour and absence from germ line traces. Some regions that failed to amplify in the first attempt were re-addressed with the addition of 5% DMSO and 5% betaine to the sequencing reactions, but otherwise maintaining the PCR conditions. SNVs in certain genes, such as BCL7A and HDAC7, repeatedly failed to amplify and for these, it was not possible to address whether the mutations in these genes were somatically acquired or were present in the germ line. Validation was not performed for variants in BCL2 or CD79B as their somatic mutation status in DLBCL is well established.

Detection of Enrichment of Functional Gene Classes within Frequently Mutated Genes Significant functional classes represented in the cSNV list were identified using the DAVID Functional Annotation tool. Reported P values were corrected for multiple testing using the Benjamini method.

Detection of Mutations with Imbalanced/Skewed Expression

The analysis of imbalanced expression was restricted to (1) confirmed somatic nonsynonymous point mutations along with (2) previously published hot spot mutations. In total, there were 381 such mutations in 99 of the 109 genes represented in the RNA-seq data. For each mutated gene, the number of aligned reads supporting the reference and mutant allele was determined. For genes with multiple mutations in the same patient (e.g. BCL2), the sum of all reads supporting each of the non-reference alleles in that patient was used instead (assuming that all mutations were restricted to the same allele). Significant imbalance/skew was computed using the binomial exact test and P values were corrected using the Bonferroni method.

Calculation of Selective Pressure

To determine if mutational patterns were indicative of selective pressure, both synonymous and non-synonymous cSNVs were considered across the patient cohort (excluding those found to be present in the germ line or false positives after validation). Selection can be inferred when the type of mutations in a gene differs from those expected by chance given a specific mutation profile. To analyse the significance of this deviation, methods described by Greenman and colleagues [20] were applied to identify genes with signatures of selection. This analysis was performed on the 101 (of 109 total) genes that had, in addition to 2 or more confirmed somatic mutations, more than 2 cSNVs in total. The coding sequence of each gene (using the longest Refseq annotation for that gene) was scanned for all possible silent and non-silent mutations (missense and truncating) matching six types of sequence changes (C>A, C>G, C>T, T>A, T>C, T>G). The separation of mutations into different strata allows the model to consider the overall effect that cancer specific mutation mechanisms may have on the mutation profile. A null-selection mutation profile is estimated via the synonymous mutations, under the assumption that they do not confer an advantage to the tumour. A score statistic describing the selective pressure was then calculated by comparing the expected mutations of each type to the observed ones. Statistical significance was then determined by constructing an empirical distribution of scores from 100,000 Monte Carlo simulations under the null hypothesis of no selection. The number of Monte Carlo iterations was increased to a maximum of 14,600,000 for genes that did not obtain a p-value at the default 100,000 simulations. The type and strength of the selective pressure the genes were under were also estimated using the models described by Greenman et al. [20]. This is represented by a quantitative value of less than, equal to, or larger than 1 for negative, null, or positive selection respectively (Table 1, other data not shown).

Several genes in the list have previously been identified as targets of somatic hypermutation (SHM), which is mediated by the enzyme AICDA (also known as AID) and targets a limited number of genes in DLBCL [65, 66]. In an attempt to avoid biasing the selective pressure model with the distinct mutational signature caused by somatic hypermutation, the genes were split into two sets. The hypermutation set contained genes previously reported to be targets of SHM (BCL2 [17], BCL6, IRF4, PIM1, and CIITA) and the non-hypermutation set contained the remaining 95 genes. The effect of the different mutational profiles of both sets can be appreciated by considering the BCL2 case. When inserted into the model with the rest of the genes BCL2 presented the highest selective pressure of all genes (65.65); however, when the selective pressure model was applied to the hypermutated genes separately, BCL2 selective pressure was estimated at 3.78.

Identifying Genes with Mutation Hot Spots

Hot spots were identified by searching for clustered mutations in the cSNVs identified by RNA-seq. Owing to the lack of constitutional DNA sequence from some patient samples, whether the variants detected only by RNA-seq were present in the germ line could not necessarily be discerned. Cases were sought in which codons were recurrently mutated. To find hot spots in the RNA-seq data, a search was performed for sets of distinct variants producing non-synonymous changes affecting the same codon in different tumours. The genes that met this criterion (Table 4) included known targets of recurrent mutation (EZH2, CARD11 [18] and CD79B [9]) and three hot spots in MEF2B. Also among these genes were known targets of aberrant somatic hypermutation in DLBCL, including BCL2, IRF4 [65], PIM1 [66], BCL6 [67], and BCL7A [65].

Analysis of Aligned Genomic DNA Sequence for Copy Number Alterations and LOH

For the identification of copy number variations (CNVs), sequence quality filtering was used to remove all reads of low mapping quality (Q≤10). Due to the varying numbers of sequence reads from each sample, aligned reference reads were first used to define genomic bins of equal reference coverage to which depths of alignments of sequence from each of the tumour samples were compared. This resulted in a measurement of the relative number of aligned reads from the tumours and reference in bins of variable length along the genome, where bin width is inversely proportional to the number of mapped reference reads. After an estimate of differential GC bias was used to reduce noise, an HMM was used to classify and segment continuous regions of copy number loss, neutrality, or gain using methodology outlined previously [68].

Loss of heterozygosity was determined for each sample using the lists of genomic SNPs that were identified through the BWA/SNVMix pipeline. This analysis allows for classification of each SNP as either heterozygous or homozygous based on the reported SNP probabilities. For each sample, genomic bins of consistent SNP coverage were used by an HMM to identify genomic regions of consistent rates of heterozygosity. The HMM partitioned each tumour genome into three states: normal heterozygosity, increased homozygosity (low), and total homozygosity (high). It can be inferred that a region of low homozygosity either represents a state where only a portion of the cellular population had lost a copy of a chromosomal region or the signal was convoluted due to contaminating normal cells in the tumour. Both states of reduced homozygosity are displayed in blue in FIG. 1, generated by Circos [69].

Assembly-Based Analysis of Tumour DNA and RNA Sequence

Reads from the individual RNA-seq libraries were assembled using ABySS as previously described [70] using multiple values of k. Iterative pairwise alignments of the contigs from the individual kmer assemblies resulted in a merged contig set that was aligned against the reference Human genome (hg18) using BLAT as described [48]. Putative fusions were identified from contigs that had alignments to two distinct genomic locations. The putative events were filtered using evidence from alignment of reads to contigs using Bowtie and alignments of reads to the genome using BWA. Those events with at least four read pairs from the reads-to-genome alignment and two supporting reads from the reads-to-contig alignment (i.e. across the fusion breakpoint) were manually curated to produce a final list of putative fusions. The genomic breakpoints for the transcriptome predicted events were identified manually from the alignments of the reads to the genome using IGV. The genomic breakpoints were later confirmed by assembly using ABySS.

Putative indels were identified from alignment of the contigs to hg18 using BLAT when contiguous unmatched base(s) were found in either the contig (insertion) or reference (deletion) sequences. The events were filtered for read support with events requiring three or more reads to be considered in the filtered set. The filtered set was then screened against dbSNP130 to find putative novel events. The resulting set was manually inspected using read alignments (against both the genome and contigs) to visually confirm candidates. This approach revealed the deletion in GNA13 shown in FIG. 5.

The splicing alterations in MLL2 (FIGS. 3B and C) and GNA13 (FIG. 5) were identified from pairwise alignments of the contigs to hg18 using BLAT. The contig alignments were then matched against the four known gene models to identify novel splice junctions. The putative novel splice junctions were filtered where two or more reads were required across the novel junction for the event to be considered. Manual inspection using read alignments (against both the genome and contigs) was performed to visually confirm candidates.

Cell of Origin Subtype Assignment Using RNA-Seq Expression Values

Global gene expression signatures measured with microarrays are the standard method for classifying DLBCL samples into the two molecular subtypes (GCB and ABC). The Bayesian method described by Wright et al. [50] was adapted to allow classification to be accomplished with the expression values obtained from RNA-seq data. To accomplish this, expression values for each Ensembl gene model (version 54) were computed as FPKM (fragments per kilobase gene model per million, rather than RPKM to account for the use of paired-end reads) and log-transformed. The current standard approach for routinely classifying samples using Affymetrix U133 arrays employs 186 probesets (George Wright, personal communication). The 165 Ensembl genes that correspond to these probesets were used for classification by RNA-seq. The classifier was trained using the 43 cases previously classified as GCB and 21 classified as ABC using Affymetrix data. The FPKM values for these genes were compared between the samples with known subtypes using the T test and those producing a P value <0.01 were used for the classifier. The robustness of this approach was tested using leave-one-out cross-validation, which resulted in no mis-classifications. Similarly, no samples were mis-classified when all cases with known COO (based on Affymetrix data) were used to produce the classifier however there were some cases that were defined as unclassifiable (U) by one method and given a subtype assignment by the other method. In such cases, the subtype assignment (rather than U) was used.

Targeted MEF2B Resequencing Using Biotinylated RNA Capture Probes

The following strategy was used to sequence the entire MEF2B locus in multiple patient samples in multiplex. Four exonic regions of the MEF2B gene were amplified from a template consisting of a pool of DNAs from three bacterial artificial chromosomes (BACs) containing the MEF2B locus (M. Nefedov, P. J. de Jong and U Surtiby, unpublished) using PCR. PCR reactions consisting of 0.5 Units PHUSION® DNA Polymerase (New England Biolabs, Pickering, Ont.), 0.25 mM dNTPs, 3% DMSO, 0.4 µM of the forward and reverse primer and 5 pmol template were cycled on a MJR Pelletier Thermocycler (model PTC-225) for 30 seconds at 980° C.; 25×{10 seconds at 98° C., 30 seconds at 65° C., 30 seconds at 72° C.}; 5 minutes at 720° C. The resulting PCR amplicons, ranging in size from 342 to 474 bp, were size selected on an 8% NOVEX®-TBE gel (Invitrogen Canada Inc., Burlington, Ont.), excised and eluted into 300 µL of elution buffer containing 5:1 (vol/vol) LoTe (3 mM Tris-HCl, pH7.5, 0.2 nM EDTA)/7.5 M ammonium acetate. The eluates were purified from gel slurries by centrifugation through Spin-X centrifuge tube filters (Fisher Scientific Ltd., Nepean, Ont.), and EtOH precipitated. Purified amplicon DNAs were quantified using an Agilent DNA 1000 Series II assay (Agilent Technologies Canada Inc., Mississauga, Ont.). Individual amplicons were pooled (equimolar) and sheared using the Covaris S2 focused ultra-sonicator (Covaris Inc., Woburn, Mass.) with the following settings; 10% Duty cycle, 5% Intensity, and 200 Cycles per burst for 180 seconds. The resulting products were size fractioned on an 8% NOVEX® TBE gel (Invitrogen Canada Inc.) and the 75 to 125 bp fraction isolated, purified and quantified as above. 30 ng of resulting DNA was end-repaired, 3-prime modified with Adenosine overhangs, and ligated to custom adapters containing T7 and T3 promoter sequences as described [71]. Adapter-ligated products were enriched by PCR as above using T3 and T7 sense strand-specific primers and the following cycling conditions; 1 min. at 980 C; 8×{10 seconds at 98° C., 30 seconds at 60° C., 30 seconds at 72° C.}; 5 minutes at 720° C. The amplified products were separated from excess adapter on an 8% NOVEX® TBE gel (Invitrogen Canada Inc.), purified, and quantified using the Qubit QUANT-IT™ assay and Qubit Fluorometer (Invitrogen Canada Inc.). An in vitro transcription reaction was carried out using 100 ng of purified adapter-ligated DNA as per the manufacturer's specifications (AMPLISCRIBE™ T7-FLASH™ Biotin-RNA Transcription Kit; Intersciences Inc., Markham, Ont.). The reaction mixture was incubated at 37° C. for 60 minutes, DNase-I treated for 15 minutes at 37° C., and then incubated at 70° C. for 5 minutes to inactivate DNaseI. Transcription products were precipitated with 1 volume of 5M NH4Ac, and size fractioned on a 10% NOVEX® TBE-Urea gel (Invitrogen Canada Inc.). The 100 to 150 bp fraction was isolated from the gel, eluted into 0.3M NaCl, and EtOH-precipitated after extraction of the eluate from the gel slurry by centrifugation through a Spin-X Filter centrifuge tube filter (Fisher Scientific Ltd.). The biotinylated RNA was resuspended in 20 µl nuclease-free water and quantified using an Agilent RNA Nano assay (Agilent Technologies Canada Inc.).

Indexed libraries of patient genomic DNA were pooled from 96 well plates in groups ranging from 36 to 47 libraries per pool [72]. A 250 to 350 bp size fraction from each pool was size-selected by gel purification from an 8% NOVEX® TBE gel as above (Invitrogen Canada Inc.). The protocol described by Gnirke and colleagues [73] was followed for the hybridization reaction and subsequent washes, with an additional oligonucleotide block consisting of standard Illumina PCR primers PE1 and PE2 included in the hybridization reaction mixture to prevent cross-hybridization between library fragments. The incubation of the library fragments with the RNA probe pool was carried out for 24 hours at 65° C., followed by binding to M-280 Streptavidin DYNA-BEADS® (Invitrogen Canada Inc.), washes, and elution of the captured library fragments. The eluted fragments were amplified by PCR using primers that anneal upstream of the adapter index sites and subjected to cluster generation and sequencing as described above.

Targeted MLL2 Resequencing Using Long-Range PCR and Sample Indexing

Due to the presence of inactivating mutations in different positions within the MLL2 gene, the entire MLL2 locus (chr12:47,699,025-47,735,374; hg18) was sequenced in a cohort of 35 FL and 37 DLBCL primary tumours, in 17 DLBCL derived cell lines and, as a control, in 8 centroblast samples. Genomic DNA from individual samples was normalized to 5 ng/µl, and 12.5 ng of each sample was PCR amplified using LA Taq DNA polymerase (TaKaRa). Twelve long amplicons, of sizes ranging from 6600 bp to 7800 bp, were obtained under the following PCR conditions: 94° C. for 5 minutes, 35 cycles of 98° C. for 10 seconds and 68° C. for 8 minutes, and a final extension at 72° C. for 10 minutes. Amplicons were cleaned using AMPure beads (Beckman Coulter) and eluted with 20-µL of TE. All 12 amplicons per sample were normalized and pooled together.

An individual indexed library was constructed from each sample (comprising the pool of the 12 long amplicons from MLL2). Approximately 500 ng of each pooled DNA sample was sheared for 10 min using a Sonic Dismembrator 550 with a power setting of "7" in pulses of 30 seconds interspersed with 30 seconds of cooling (Cup Horn, Fisher Scientific) and then analysed on 8% PAGE gels. The 200 to 300 bp DNA fraction was excised and eluted from the gel slice overnight at 4° C. in 300 µL of elution buffer (5:1 (vol/vol) LoTE buffer (3 mM Tris-HCl, pH 7.5, 0.2 mM EDTA)/7.5 M ammonium acetate) and was purified using a Spin-X FilterTube (Fisher Scientific) and by ethanol precipitation. Indexed libraries were prepared using a modified paired-end protocol. This involved DNA end-repair reactions at room temperature 20-25° C. for 30 minutes (5 U T4 DNA polymerase, 1 U Klenow DNA polymerase (exonuclease minus), 100 U T4 polynucleotide kinase and 0.4 mM dNTP mix (Invitrogen). End-repair reactions were purified using AMPure beads, and dATP was added to the 3' ends using 5 U Klenow DNA polymerase (exonuclease minus)

and 0.2 mM dATP in 1× Klenow Buffer (Invitrogen) with 30-minute incubation at 37° C. in a Tetrad thermal cycler (MJ Research). DNA was again purified on AMPure beads using a Biomek FX. Adapter ligation (10:1 ratio) was completed with 0.03 µM adapter (multiplexing adapters 1 and 2), 100 ng DNA, 5 U T4 DNA ligase, 0.2 mM ATP and 1×T4 DNA Ligase Buffer (Invitrogen) for 30 minutes at room temperature. Adapter-ligated DNA was again purified using AMPure beads on a Biomek FX. A selection of DNA samples were quantified on a Qubit (Invitrogen). 15-cycle indexing enrichment PCR was performed using Phusion DNA polymerase and Primers 1.0 and 2.0 (IDT) and 96 custom indexing primers. PCR cycles were: 98° C. for 60 seconds, followed by 15 cycles of 98° C. for 10 seconds, 65° C. for 15 seconds and 72° C. for 30 seconds. The PCR products were purified using AMPure beads and eluted in 40 µL elution buffer EB (Qiagen). Product quality was assessed by quality-control gels with 1.75% SeaKem LE agarose in 1×TAE (0.2 µL of every amplicon) and on a 2100 Bioanalyzer (Agilent Technologies).

Indexed libraries were pooled together and sequenced on two lanes of a flowcell using an Illumina $GA_{II}$ platform. Individual indexes allowed the deconvolution of reads deriving from individual samples in multiplexed libraries such that many cases were concurrently sequenced in the same flow cell lane. The reads were matched to patient samples using the index read and were aligned with BWA to the human reference genome (hg18). Point mutations were identified using SNVMix with stringent post-filtration including a requirement for dual-strand coverage and requiring at least 10% of the aligned reads at a candidate variant to be non-reference. Insertions and deletions were identified using the SAMtools indel calling algorithm with similar filters. Only insertions and deletions supported by at least 2 reads on each strand were considered valid. The reported average coverage for each sample was calculated as the average depth of aligned reads across each of the coding (CDS) positions in the MLL2 locus.

Re-Confirmation of MLL2 Mutations in Patient Samples and DLBCL Cell Lines

MLL2 mutations found by targeted sequencing of MLL2 in lymphoma samples were validated by Sanger sequencing of the region surrounding each mutation, except in 15 cases. To do so, primers were designed to amplify 400-600 bp regions by PCR. Validating forward and reverse primers carried T7 and M13Reverse 5' tails, respectively. PCR conditions used were 94° C. for 2 minutes, 30 cycles of 94° C. for 30 seconds, 600C for 30 seconds and 72° C. for 1 minute, and a final extension at 72° C. for 8 minutes. To determine the somatic or germline origin of the mutations, mutations were re-sequenced in both tumour and constitutional DNA, the latter obtained from peripheral blood or negative sort cells. The sequencing reactions consisted of 50 cycles of 96° C. for 10 sec, 43° C. (for M13Reverse) or 48° C. (T7) for 5 seconds and 60° C. for 4 minutes and were analysed using an AB 3730XL. Variants were visually inspected to confirm their presence in tumour and absence from germline traces. In 8 of the patient samples that carried 2 mutations in MLL2, to establish whether one allele contained both mutations or each allele contained one, we sequenced both candidate mutations using DNA from BAC clones from FL patient libraries. The primers and PCR conditions were the same as those used for the validation of each of those mutations.

Targeted Resequencing of MEF2B Coding Exons 1 and 2

Coding exons 1 and 2 of MEF2B were PCR amplified using MEF2B_1F/R and MEF2B_2F/R primers using the same conditions for MLL2 (previous paragraph). Priming sites for T7 and M13Reverse were added to their 5' ends to allow direct Sanger sequencing of amplicons. Amplicons were produced from whole genome amplified tumour genomic DNA from lymphoma patients and DLBCL cell lines. Whole genome amplification was performed using REPLI-G® Screening kit reagents (Qiagen), following the manufacturer instructions. All capillary traces were visually inspected.

Identification of Structural Aberrations Involving BCL2 and BCL6

The presence of translocations involving MYC, BCL2 and BCL6 was determined for 49 of the DLBCL cases (FIG. 2) using commercial dual color "break-apart" probes from Abbott Molecular (Abbott Park, IL) on formalin fixed paraffin embedded tissue in tissue microarrays using the described method [74]. Additional fusion transcripts involving BCL2 or BCL6 were detected in these and the remaining libraries directly from the RNA-seq data using both Trans-ABySS [48] and deFuse.

Analysis of Impact of COO and Mutation Status on Outcome in DLBCL

The analysis included only patients treated with curative intent who received at least one cycle of R-CHOP. Overall survival (OS) was calculated as the time from date of diagnosis until death from any cause. Patients were censored at the time they were last known to be alive. OS was assessed using the Kaplan-Meier method and the log rank test was used for comparison between groups. Data were analysed using SPSS software (SPSS version 14.0 for Windows; SPSS Inc, Chicago, Ill.).

TABLE 1

Overview of cSNVs and confirmed somatic mutations in most frequently mutated genes.

| Gene | Cases | | | Total | | | Somatic cSNVs (RNA-seq cohort)* | P (raw) | q | NS SP | T SP | Skew (M, WT, both)*** |
| --- | --- | --- | --- | --- | --- | --- | --- | --- | --- | --- | --- | --- |
| | NS | S | T | NS | S | T | | | | | | |
| MLL2† | 16 | 8 | 17 | 17 | 8 | 18 | 10 | $6.85 \times 10^{-8}$ | $8.50 \times 10^{-7}$ | 0.834 | 14.4 | WT |
| TNFRSF14$^{G†}$ | 7 | 1 | 7 | 8 | 1 | 7 | 11 | $6.85 \times 10^{-8}$ | $8.50 \times 10^{-7}$ | 7.52 | 118 | both |
| SGK1$^{G†}$ | 18 | 6 | 6 | 37 | 10 | 6 | 9 | $6.85 \times 10^{-8}$ | $8.50 \times 10^{-7}$ | 19.5 | 61.7 | — |
| BCL10† | 2 | 0 | 4 | 3 | 0 | 4 | 4 | $6.85 \times 10^{-8}$ | $8.50 \times 10^{-7}$ | 3.62 | 112 | WT |
| GNA13$^{G†}$ | 21 | 1 | 2 | 33 | 1 | 2 | 5 | $6.85 \times 10^{-8}$ | $8.50 \times 10^{-7}$ | 24.1 | 25.7 | both |
| TP53$^{G†}$ | 20 | 2 | 1 | 23 | 3 | 1 | 22 | $6.85 \times 10^{-8}$ | $8.50 \times 10^{-7}$ | 15.6 | 14.1 | both |
| EZH2$^{G†}$ | 33 | 0 | 0 | 33 | 0 | 0 | 33 | $6.85 \times 10^{-8}$ | $8.50 \times 10^{-7}$ | 11.4 | 0.00 | both |
| BTG2† | 12 | 6 | 1 | 14 | 6 | 1 | 2 | $6.85 \times 10^{-8}$ | $8.50 \times 10^{-7}$ | 23.9 | 35.1 | — |
| BCL2$^{G†}$ | 42 | 45 | 0 | 96 | 105 | 0 | 43 | $9.35 \times 10^{-8}$ | $8.50 \times 10^{-7}$ | 3.78 | 0.00 | M |

TABLE 1-continued

Overview of cSNVs and confirmed somatic mutations in most frequently mutated genes.

| Gene | Cases NS | Cases S | Cases T | Total NS | Total S | Total T | Somatic cSNVs (RNA-seq cohort)* | P (raw) | q | NS SP | T SP | Skew (M, WT, both)*** |
|---|---|---|---|---|---|---|---|---|---|---|---|---|
| BCL6† | 11 | 2 | 0 | 12 | 2 | 0 | 2 | 9.35 × 10⁻⁸** | 8.50 × 10⁻⁷ | 0.175 | 0.00 | M |
| CIITA† | 5 | 3 | 0 | 6 | 3 | 0 | 2 | 9.35 × 10⁻⁸** | 8.50 × 10⁻⁷ | 0.086 | 0.00 | |
| FAS† | 2 | 0 | 4 | 3 | 0 | 4 | 2 | 1.52 × 10⁻⁷ | 1.17 × 10⁻⁶ | 2.54 | 66.5 | WT |
| BTG1† | 11 | 6 | 2 | 11 | 7 | 2 | 10 | 1.52 × 10⁻⁷ | 1.17 × 10⁻⁶ | 17.5 | 52.5 | both |
| MEF2B^G† | 20 | 2 | 0 | 20 | 2 | 0 | 10 | 2.05 × 10⁻⁷ | 1.47 × 10⁻⁶ | 14.2 | 0.00 | M |
| IRF8† | 11 | 5 | 3 | 14 | 5 | 3 | 3 | 4.55 × 10⁻⁷ | 3.03 × 10⁻⁶ | 8.82 | 28.2 | WT |
| TMEM30A† | 1 | 0 | 4 | 1 | 0 | 4 | 4 | 6.06 × 10⁻⁷ | 3.79 × 10⁻⁶ | 0.785 | 65.0 | WT |
| CD58† | 2 | 0 | 3 | 2 | 0 | 3 | 2 | 2.42 × 10⁻⁶ | 1.43 × 10⁻⁵ | 2.29 | 69.2 | — |
| KLHL6† | 10 | 2 | 2 | 12 | 2 | 2 | 4 | 1.00 × 10⁻⁵ | 5.26 × 10⁻⁵ | 5.42 | 16.4 | — |
| MYD88^A† | 13 | 2 | 0 | 14 | 2 | 0 | 9 | 1.00 × 10⁻⁵ | 5.26 × 10⁻⁵ | 12.4 | 0.00 | WT |
| CD70† | 5 | 0 | 1 | 5 | 0 | 2 | 3 | 1.70 × 10⁻⁵ | 8.48 × 10⁻⁵ | 7.08 | 44.0 | — |
| CD79B^A† | 7 | 2 | 1 | 9 | 2 | 1 | 5 | 2.00 × 10⁻⁵ | 9.52 × 10⁻⁵ | 10.9 | 18.3 | M |
| CCND3† | 7 | 1 | 2 | 7 | 1 | 2 | 6 | 2.80 × 10⁻⁵ | 1.27 × 10⁻⁴ | 6.55 | 36.3 | WT |
| CREBBP† | 20 | 7 | 4 | 24 | 7 | 4 | 9 | 1.00 × 10⁻⁴ | 4.35 × 10⁻⁴ | 2.72 | 6.04 | both |
| HIST1H1C† | 9 | 0 | 0 | 10 | 0 | 0 | 6 | 1.80 × 10⁻⁴ | 7.50 × 10⁻⁴ | 11.9 | 0.00 | both |
| B2M† | 7 | 0 | 0 | 7 | 0 | 0 | 4 | 3.90 × 10⁻⁴ | 1.56 × 10⁻³ | 16.6 | 0.00 | WT |
| ETS1† | 10 | 1 | 0 | 10 | 1 | 0 | 4 | 4.10 × 10⁻⁴ | 1.58 × 10⁻³ | 5.76 | 0.00 | WT |
| CARD11† | 14 | 3 | 0 | 14 | 3 | 0 | 3 | 1.90 × 10⁻³ | 7.04 × 10⁻³ | 3.37 | 0.00 | both |
| FAT2†** | 2 | 1 | 0 | 2 | 1 | 0 | 2 | 6.30 × 10⁻³ | 2.25 × 10⁻² | 0.128 | 0.00 | — |
| IRF4†** | 9 | 4 | 0 | 26 | 5 | 0 | 5 | 7.00 × 10⁻³ | 2.41 × 10⁻² | 0.569 | 0.00 | both |
| FOXO1† | 8 | 4 | 0 | 10 | 4 | 0 | 4 | 7.60 × 10³ | 2.53 × 10⁻² | 4.02 | 0.00 | — |
| STAT3 | 9 | 0 | 0 | 9 | 0 | 0 | 4 | 2.19 × 10⁻² | 6.08 × 10⁻² | — | — | both |
| RAPGEF1 | 8 | 3 | 0 | 10 | 3 | 0 | 3 | 2.98 × 10⁻² | 7.45 × 10⁻² | — | — | WT |
| ABCA7 | 12 | 3 | 0 | 15 | 3 | 0 | 2 | 7.76 × 10⁻² | 1.67 × 10⁻¹ | — | — | WT |
| RNF213 | 10 | 8 | 0 | 10 | 8 | 0 | 2 | 7.87 × 10⁻² | 1.67 × 10⁻¹ | — | — | — |
| MUC16 | 17 | 12 | 0 | 39 | 25 | 0 | 2 | 8.32 × 10⁻² | 1.73 × 10⁻¹ | — | — | — |
| HDAC7 | 8 | 4 | 0 | 8 | 4 | 0 | 2 | 8.94 × 10⁻² | 1.82 × 10⁻¹ | — | — | WT |
| PRKDC | 7 | 3 | 0 | 7 | 4 | 0 | 2 | 1.06 × 10⁻¹ | 2.05 × 10⁻¹ | — | — | — |
| SAMD9 | 9 | 2 | 0 | 9 | 2 | 0 | 2 | 1.79 × 10⁻¹ | 3.01 × 10⁻¹ | — | — | — |
| TAF1 | 10 | 0 | 0 | 10 | 0 | 0 | 2 | 3.03 × 10⁻¹ | 4.74 × 10⁻¹ | — | — | — |
| PIM1 | 20 | 19 | 0 | 33 | 34 | 0 | 11 | 3.40 × 10⁻¹ | 5.23 × 10⁻¹ | — | — | WT |
| COL4A2 | 8 | 2 | 0 | 8 | 2 | 0 | 2 | 7.64 × 10⁻¹ | 8.99 × 10⁻¹ | — | — | — |
| EP300 | 8 | 7 | 1 | 8 | 7 | 1 | 3 | 9.54 × 10⁻¹ | 1.00 | — | — | WT |

Individual cases with nonsynonymous (NS), synonymous (S) and truncating (T) mutations and total number of mutations of each class is shown separately as some genes contained multiple mutations in the same case.
The P values indicated in bold are the upper limit on the P value for that gene determined with the approach described by Greenman et al (see Methods) [19],
q is the Benjamini-corrected q value, and NS, SP and T SP refer to selective pressure estimates from this model for the acquisition of nonsynonymous or truncating mutations, respectively.
†genes significant at an FDR of 0.03. SNVs in BCL2 and previously confirmed hot spot mutations in EZH2 and CD798 are likely somatic in these samples based on published observations of others.
*Additional somatic mutations identified in larger cohorts and insertion/deletion mutations are not included in this total.
**Selective pressure estimates are both <1 indicating purifying selection rather than positive selection acting on this gene.
***"both" indicates we observed separate cases in which skewed expression was seen but where this skew was not consistent for the mutant or wild-type allele.
Genes with a superscript of either A or G were found to have mutations significantly enriched in ABC or GCB cases, respectively (P < 0.05, Fisher Exact test).

TABLE 2

Summary of types of MLL2 somatic mutations.

| Sample Type | FL | DLBCL | DLBCL cell-line | Centroblast |
|---|---|---|---|---|
| Truncation | 18 | 4 | 7 | 0 |
| Indel with frameshift | 22 | 8 | 6 | 0 |
| Splice site | 4 | 2 | 0 | 0 |
| SNV | 3 | 2 | 2 | 0 |
| Any mutation (number of cases) | 31/35 | 12/37 | 10/17 | 0/8 |
| Percentage | 89% | 32% | 59% | 0% |

TABLE 3

Mutations in selected B-cell NHL biomarkers from exome and genome sequencing.

| Gene symbol | Ensembl id | Detection method | Base change | Annotation | Total cSNVs in gene |
|---|---|---|---|---|---|
| ABCA7 | ENSG00000064687 | genome | G > A | E1322K | 13 |
| ABCA7 | ENSG00000064687 | RNA-seq | C > T | S268L | 13 |

TABLE 3-continued

Mutations in selected B-cell NHL biomarkers from exome and genome sequencing.

| Gene symbol | Ensembl id | Detection method | Base change | Annotation | Total cSNVs in gene |
|---|---|---|---|---|---|
| B2M | ENSG00000166710 | RNA-seq | T > A | Y86N | 12 |
| B2M | ENSG00000166710 | RNA-seq | T > G | M1R | 12 |
| B2M | ENSG00000166710 | RNA-seq | A > T | M1L | 12 |
| B2M | ENSG00000166710 | genome | T > A | L12Q | 12 |
| BCL10 | ENSG00000142867 | genome | A > C | L225* | 4 |
| BCL10 | ENSG00000142867 | genome | T > A | T229S | 4 |
| BCL10 | ENSG00000142867 | genome | G > A | S227L | 4 |
| BCL10 | ENSG00000142867 | RNA-seq | G > C | S136* | 4 |
| BCL10 | ENSG00000142867 | RNA-seq | T > A | R135* | 4 |
| BCL10 | ENSG00000142867 | RNA-seq | T > A | K146* | 4 |
| BCL10 | ENSG00000142867 | RNA-seq | T > A | L225F | 4 |
| BCL2 | ENSG00000171791 | exome | C > T | A2T | 42 |
| BCL2 | ENSG00000171791 | exome | G > C | H3D | 42 |
| BCL2 | ENSG00000171791 | RNA-seq | C > A | R6I | 42 |
| BCL2 | ENSG00000171791 | RNA-seq | G > A | P57S | 42 |
| BCL2 | ENSG00000171791 | RNA-seq | C > T | V35M | 42 |
| BCL2 | ENSG00000171791 | RNA-seq | A > C | M16R | 42 |
| BCL2 | ENSG00000171791 | RNA-seq | A > G | F104L | 42 |
| BCL2 | ENSG00000171791 | RNA-seq | G > A | A131V | 42 |
| BCL2 | ENSG00000171791 | RNA-seq | C > T | A61T | 42 |
| BCL2 | ENSG00000171791 | RNA-seq | C > T | A2T | 42 |
| BCL2 | ENSG00000171791 | RNA-seq | T > A | Y28F | 42 |
| BCL2 | ENSG00000171791 | RNA-seq | G > A | A60V | 42 |
| BCL2 | ENSG00000171791 | RNA-seq | G > A | L86F | 42 |
| BCL2 | ENSG00000171791 | RNA-seq | A > G | F49S | 42 |
| BCL2 | ENSG00000171791 | RNA-seq | A > C | H20Q | 42 |
| BCL2 | ENSG00000171791 | RNA-seq | C > T | R146K | 42 |
| BCL2 | ENSG00000171791 | RNA-seq | C > G | E135D | 42 |
| BCL2 | ENSG00000171791 | RNA-seq | C > T | G47D | 42 |
| BCL2 | ENSG00000171791 | RNA-seq | T > A | N11Y | 42 |
| BCL2 | ENSG00000171791 | RNA-seq | C > T | D31N | 42 |
| BCL2 | ENSG00000171791 | RNA-seq | G > A | A37V | 42 |
| BCL2 | ENSG00000171791 | RNA-seq | C > T | R129H | 42 |
| BCL2 | ENSG00000171791 | RNA-seq | T > C | M16V | 42 |
| BCL2 | ENSG00000171791 | RNA-seq | G > A | P59L | 42 |
| BCL2 | ENSG00000171791 | RNA-seq | G > C | L119V | 42 |
| BCL2 | ENSG00000171791 | RNA-seq | A > T | M16K | 42 |
| BCL2 | ENSG00000171791 | RNA-seq | T > A | T125S | 42 |
| BCL2 | ENSG00000171791 | RNA-seq | G > A | T74I | 42 |
| BCL2 | ENSG00000171791 | RNA-seq | A > G | S51P | 42 |
| BCL2 | ENSG00000171791 | RNA-seq | C > A | K17N | 42 |
| BCL2 | ENSG00000171791 | RNA-seq | C > A | G5V | 42 |
| BCL2 | ENSG00000171791 | RNA-seq | G > A | P59S | 42 |
| BCL2 | ENSG00000171791 | RNA-seq | G > C | P57A | 42 |
| BCL2 | ENSG00000171791 | RNA-seq | T > C | D34G | 42 |
| BCL2 | ENSG00000171791 | RNA-seq | T > C | I48V | 42 |
| BCL2 | ENSG00000171791 | RNA-seq | G > C | A60G | 42 |
| BCL2 | ENSG00000171791 | RNA-seq | G > C | N11K | 42 |
| BCL2 | ENSG00000171791 | RNA-seq | T > C | T69A | 42 |
| BCL2 | ENSG00000171791 | RNA-seq | C > T | A76T | 42 |
| BCL2 | ENSG00000171791 | RNA-seq | G > A | A60V | 42 |
| BCL2 | ENSG00000171791 | RNA-seq | A > C | H20Q | 42 |
| BCL2 | ENSG00000171791 | RNA-seq | A > C | S167A | 42 |
| BCL2 | ENSG00000171791 | RNA-seq | G > A | T187I | 42 |
| BCL2 | ENSG00000171791 | RNA-seq | C > T | S87N | 42 |
| BCL2 | ENSG00000171791 | RNA-seq | A > T | H20Q | 42 |
| BCL2 | ENSG00000171791 | RNA-seq | C > G | E13D | 42 |
| BCL2 | ENSG00000171791 | RNA-seq | A > G | V156A | 42 |
| BCL2 | ENSG00000171791 | RNA-seq | G > C | F104L | 42 |
| BCL2 | ENSG00000171791 | RNA-seq | T > C | N172S | 42 |
| BCL2 | ENSG00000171791 | RNA-seq | A > G | S50P | 42 |
| BCL2 | ENSG00000171791 | RNA-seq | G > A | P59L | 42 |
| BCL2 | ENSG00000171791 | RNA-seq | G > A | P59S | 42 |
| BCL2 | ENSG00000171791 | RNA-seq | C > A | R107L | 42 |
| BCL2 | ENSG00000171791 | RNA-seq | A > G | Y21H | 42 |
| BCL2 | ENSG00000171791 | RNA-seq | T > C | Q52R | 42 |
| BCL2 | ENSG00000171791 | RNA-seq | G > C | T7R | 42 |
| BCL2 | ENSG00000171791 | RNA-seq | C > T | E165K | 42 |
| BCL2 | ENSG00000171791 | RNA-seq | G > A | A80V | 42 |
| BCL2 | ENSG00000171791 | RNA-seq | C > T | R146K | 42 |
| BCL2 | ENSG00000171791 | RNA-seq | A > G | F49L | 42 |
| BCL2 | ENSG00000171791 | RNA-seq | A > C | F49C | 42 |
| BCL2 | ENSG00000171791 | RNA-seq | C > G | K17N | 42 |
| BCL2 | ENSG00000171791 | RNA-seq | G > A | P65S | 42 |

TABLE 3-continued

Mutations in selected B-cell NHL biomarkers from exome and genome sequencing.

| Gene symbol | Ensembl id | Detection method | Base change | Annotation | Total cSNVs in gene |
|---|---|---|---|---|---|
| BCL2 | ENSG00000171791 | RNA-seq | G > T | A60D | 42 |
| BCL2 | ENSG00000171791 | RNA-seq | G > T | S51Y | 42 |
| BCL2 | ENSG00000171791 | RNA-seq | G > A | P71S | 42 |
| BCL2 | ENSG00000171791 | RNA-seq | G > A | A43V | 42 |
| BCL2 | ENSG00000171791 | RNA-seq | G > A | P59S | 42 |
| BCL2 | ENSG00000171791 | RNA-seq | C > T | G27D | 42 |
| BCL2 | ENSG00000171791 | RNA-seq | G > C | A131G | 42 |
| BCL2 | ENSG00000171791 | RNA-seq | C > T | S87N | 42 |
| BCL2 | ENSG00000171791 | RNA-seq | A > T | L169Q | 42 |
| BCL2 | ENSG00000171791 | RNA-seq | G > A | A131V | 42 |
| BCL2 | ENSG00000171791 | RNA-seq | C > A | A45S | 42 |
| BCL2 | ENSG00000171791 | RNA-seq | C > T | A60T | 42 |
| BCL2 | ENSG00000171791 | RNA-seq | T > G | T69P | 42 |
| BCL2 | ENSG00000171791 | RNA-seq | G > C | S117R | 42 |
| BCL2 | ENSG00000171791 | RNA-seq | A > G | F49L | 42 |
| BCL2 | ENSG00000171791 | RNA-seq | C > T | G47D | 42 |
| BCL2 | ENSG00000171791 | RNA-seq | C > T | V66I | 42 |
| BCL2 | ENSG00000171791 | RNA-seq | G > C | P46A | 42 |
| BCL2 | ENSG00000171791 | RNA-seq | G > A | P59S | 42 |
| BCL2 | ENSG00000171791 | RNA-seq | G > C | P59A | 42 |
| BCL2 | ENSG00000171791 | RNA-seq | G > C | P46A | 42 |
| BCL2 | ENSG00000171791 | RNA-seq | G > A | A131V | 42 |
| BCL2 | ENSG00000171791 | RNA-seq | T > A | Y9F | 42 |
| BCL2 | ENSG00000171791 | RNA-seq | A > G | V159A | 42 |
| BCL2 | ENSG00000171791 | RNA-seq | G > A | T7I | 42 |
| BCL2 | ENSG00000171791 | RNA-seq | G > A | P53S | 42 |
| BCL2 | ENSG00000171791 | RNA-seq | G > C | S87R | 42 |
| BCL2 | ENSG00000171791 | RNA-seq | G > T | T7K | 42 |
| BCL2 | ENSG00000171791 | RNA-seq | C > T | R164Q | 42 |
| BCL2 | ENSG00000171791 | RNA-seq | G > A | T7I | 42 |
| BCL2 | ENSG00000171791 | RNA-seq | T > A | I48F | 42 |
| BCL2 | ENSG00000171791 | RNA-seq | T > C | Y21C | 42 |
| BCL2 | ENSG00000171791 | RNA-seq | T > A | T132S | 42 |
| BCL2 | ENSG00000171791 | RNA-seq | T > C | N143S | 42 |
| BCL2 | ENSG00000171791 | RNA-seq | G > A | A60V | 42 |
| BCL2 | ENSG00000171791 | RNA-seq | G > A | A60V | 42 |
| BCL2 | ENSG00000171791 | RNA-seq | T > G | Y108S | 42 |
| BCL6 | ENSG00000113916 | genome | C > T | A587T | 11 |
| BCL6 | ENSG00000113916 | RNA-seq | C > T | A587T | 11 |
| BTG1 | ENSG00000133639 | genome | G > C | L94V | 13 |
| BTG1 | ENSG00000133639 | RNA-seq | G > A | P58L | 13 |
| BTG1 | ENSG00000133639 | RNA-seq | C > G | Q36H | 13 |
| BTG1 | ENSG00000133639 | RNA-seq | G > A | H2Y | 13 |
| BTG1 | ENSG00000133639 | RNA-seq | C > G | Q36H | 13 |
| BTG1 | ENSG00000133639 | RNA-seq | A > T | C149* | 13 |
| BTG1 | ENSG00000133639 | RNA-seq | C > T | R27H | 13 |
| BTG1 | ENSG00000133639 | RNA-seq | C > G | A49P | 13 |
| BTG1 | ENSG00000133639 | RNA-seq | G > C | Q38E | 13 |
| BTG1 | ENSG00000133639 | RNA-seq | C > G | E46D | 13 |
| BTG2 | ENSG00000159388 | RNA-seq | C > A | A45E | 13 |
| BTG2 | ENSG00000159388 | RNA-seq | G > A | A45T | 13 |
| CARD11 | ENSG00000198286 | exome | C > G | E86Q; E93Q; E110Q | 14 |
| CARD11 | ENSG00000198286 | exome | A > G | L244P; L251P; L268P | 14 |
| CARD11 | ENSG00000198286 | RNA-seq | T > C | Q364R; Q371R; Q388R | 14 |
| CARD11 | ENSG00000198286 | RNA-seq | A > T | M353K; M360K; M377K | 14 |
| CARD11 | ENSG00000198286 | RNA-seq | A > T | F123I; F130I; F147I | 14 |
| CARD11 | ENSG00000198286 | RNA-seq | A > T | F108I; F115I; F132I | 14 |
| CARD11 | ENSG00000198286 | RNA-seq | C > T | D394N; D401N; D418N | 14 |
| CARD11 | ENSG00000198286 | RNA-seq | A > C | Y333D; Y340D; Y357D | 14 |
| CARD11 | ENSG00000198286 | RNA-seq | A > C | N230K; N237K; N254K | 14 |
| CARD11 | ENSG00000198286 | RNA-seq | C > T | D223N; D230N; D247N | 14 |
| CARD11 | ENSG00000198286 | RNA-seq | T > G | Q242P; Q249P; Q266P | 14 |
| CARD11 | ENSG00000198286 | RNA-seq | A > C | F123C; F130C; F147C | 14 |
| CARD11 | ENSG00000198286 | RNA-seq | T > G | Q242P; Q249P; Q266P | 14 |
| CARD11 | ENSG00000198286 | RNA-seq | C > T | G116D; G123D; G140D | 14 |
| CCND3 | ENSG00000112576 | RNA-seq | G > A | P234L; P280L; P284L | 10 |
| CCND3 | ENSG00000112576 | RNA-seq | G > A | Q226*; Q272*; Q276* | 10 |
| CCND3 | ENSG00000112576 | RNA-seq | G > A | Q226*; Q272*; Q276* | 10 |
| CCND3 | ENSG00000112576 | RNA-seq | A > C | I240R; I286R; I290R | 10 |
| CCND3 | ENSG00000112576 | RNA-seq | A > T | V237D; V283D; V287D | 10 |
| CCND3 | ENSG00000112576 | RNA-seq | T > G | T233P; T279P; T283P | 10 |
| CD58 | ENSG00000116815 | genome | G > A | Q141* | 6 |
| CD58 | ENSG00000116815 | RNA-seq | C > A | C131F | 6 |
| CD70 | ENSG00000125726 | exome | A > C | L60R | 9 |

TABLE 3-continued

Mutations in selected B-cell NHL biomarkers from exome and genome sequencing.

| Gene symbol | Ensembl id | Detection method | Base change | Annotation | Total cSNVs in gene |
|---|---|---|---|---|---|
| CD70 | ENSG00000125726 | RNA-seq | A > G | F186S | 9 |
| CD70 | ENSG00000125726 | RNA-seq | C > G | G66R | 9 |
| CD79B | ENSG00000007312 | RNA-seq | T > G | Y92S; Y196S; Y197S | 8 |
| CD79B | ENSG00000007312 | RNA-seq | A > G | Y92H; Y196H; Y197H | 8 |
| CD79B | ENSG00000007312 | RNA-seq | T > A | Y92F; Y196F; Y197F | 8 |
| CD79B | ENSG00000007312 | RNA-seq | A > G | Y92H; Y196H; Y197H | 8 |
| CD79B | ENSG00000007312 | RNA-seq | T > C | Y92C; Y196C; Y197C | 8 |
| CIITA | ENSG00000179583 | exome | A > T | D748V; D777V | 12 |
| CIITA | ENSG00000179583 | RNA-seq | T > A | L810Q; L839Q | 12 |
| COL4A2 | ENSG00000134871 | genome | G > A | G441D; G447D | 8 |
| COL4A2 | ENSG00000134871 | RNA-seq | G > A | G97E | 8 |
| CREBBP | ENSG00000005339 | exome | C > T | E1012K; E1042K | 23 |
| CREBBP | ENSG00000005339 | exome | A > G | Y71H; Y1482H; Y1512H | 23 |
| CREBBP | ENSG00000005339 | RNA-seq | C > T | S25N; S1436N; S1466N | 23 |
| CREBBP | ENSG00000005339 | RNA-seq | A > T | L88Q; L1499Q; L1529Q | 23 |
| CREBBP | ENSG00000005339 | RNA-seq | A > G | Y92H; Y1503H; Y1533H | 23 |
| CREBBP | ENSG00000005339 | RNA-seq | G > C | P77R; P1488R; P1518R | 23 |
| CREBBP | ENSG00000005339 | RNA-seq | A > G | L88P; L1499P; L1529P | 23 |
| CREBBP | ENSG00000005339 | RNA-seq | G > A | R35C; R1446C; R1476C | 23 |
| CREBBP | ENSG00000005339 | RNA-seq | A > T | Y71N; Y1482N; Y1512N | 23 |
| CREBBP | ENSG00000005339 | RNA-seq | T > C | M1625V; M1655V | 23 |
| CREBBP | ENSG00000005339 | genome | G > A | Q1104*; Q1134* | 23 |
| EP300 | ENSG00000100393 | RNA-seq | T > A | Y1467N | 10 |
| EP300 | ENSG00000100393 | RNA-seq | T > C | Y1467H | 10 |
| EP300 | ENSG00000100393 | RNA-seq | G > A | A1498T | 10 |
| EP300 | ENSG00000100393 | genome | T > C | L415P | 10 |
| ETS1 | ENSG00000134954 | RNA-seq | G > A | L23F | 12 |
| ETS1 | ENSG00000134954 | RNA-seq | G > A | L23F | 12 |
| ETS1 | ENSG00000134954 | RNA-seq | C > G | E22D | 12 |
| ETS1 | ENSG00000134954 | RNA-seq | T > C | M1V | 12 |
| ETS1 | ENSG00000134954 | genome | G > C | T12S | 12 |
| EZH2 | ENSG00000106462 | genome | G > C | A638G; A682G | 33 |
| EZH2 | ENSG00000106462 | RNA-seq | G > A | A648V; A692V | 33 |
| EZH2 | ENSG00000106462 | exome | T > G | Y602S; Y646S | 33 |
| EZH2 | ENSG00000106462 | genome | T > A | Y602F; Y646F | 33 |
| EZH2 | ENSG00000106462 | exome | A > G | Y602H; Y646H | 33 |
| EZH2 | ENSG00000106462 | RNA-seq | T > A | Y602F; Y646F | 33 |
| EZH2 | ENSG00000106462 | RNA-seq | T > G | Y602S; Y646S | 33 |
| EZH2 | ENSG00000106462 | RNA-seq | A > T | Y602N; Y646N | 33 |
| EZH2 | ENSG00000106462 | RNA-seq | A > T | Y602N; Y646N | 33 |
| EZH2 | ENSG00000106462 | RNA-seq | A > T | Y602N; Y646N | 33 |
| EZH2 | ENSG00000106462 | RNA-seq | A > G | Y602H; Y646H | 33 |
| EZH2 | ENSG00000106462 | RNA-seq | A > G | Y602H; Y646H | 33 |
| EZH2 | ENSG00000106462 | RNA-seq | T > A | Y602F; Y646F | 33 |
| EZH2 | ENSG00000106462 | RNA-seq | A > G | Y602H; Y646H | 33 |
| EZH2 | ENSG00000106462 | RNA-seq | A > T | Y602N; Y646N | 33 |
| EZH2 | ENSG00000106462 | RNA-seq | A > T | Y602N; Y646N | 33 |
| EZH2 | ENSG00000106462 | RNA-seq | T > A | Y602F; Y646F | 33 |
| EZH2 | ENSG00000106462 | RNA-seq | T > G | Y602S; Y646S | 33 |
| EZH2 | ENSG00000106462 | RNA-seq | A > G | Y602H; Y646H | 33 |
| EZH2 | ENSG00000106462 | RNA-seq | T > A | Y602F; Y646F | 33 |
| EZH2 | ENSG00000106462 | RNA-seq | A > G | Y602H; Y646H | 33 |
| EZH2 | ENSG00000106462 | RNA-seq | A > T | Y602N; Y646N | 33 |
| EZH2 | ENSG00000106462 | RNA-seq | A > T | Y602N; Y646N | 33 |
| EZH2 | ENSG00000106462 | RNA-seq | T > A | Y602F; Y646F | 33 |
| EZH2 | ENSG00000106462 | RNA-seq | T > G | Y602S; Y646S | 33 |
| EZH2 | ENSG00000106462 | RNA-seq | A > T | Y602N; Y646N | 33 |
| EZH2 | ENSG00000106462 | RNA-seq | A > T | Y602N; Y646N | 33 |
| EZH2 | ENSG00000106462 | RNA-seq | A > T | Y602N; Y646N | 33 |
| EZH2 | ENSG00000106462 | RNA-seq | T > A | Y602F; Y646F | 33 |
| EZH2 | ENSG00000106462 | RNA-seq | A > T | Y602N; Y646N | 33 |
| EZH2 | ENSG00000106462 | RNA-seq | T > A | Y602F; Y646F | 33 |
| EZH2 | ENSG00000106462 | RNA-seq | A > T | Y602N; Y646N | 33 |
| FAS | ENSG00000026103 | exome | C > T | Q255*; Q276*; Q303* | 6 |
| FAS | ENSG00000026103 | RNA-seq | T > G | Y211*; Y232*; Y259* | 6 |
| FAS | ENSG00000026103 | genome | G > C | V224L; V245L; V272L | 6 |
| FAS | ENSG00000026103 | genome | A > G | D244G; D265G; D292G | 6 |
| FAT2 | ENSG00000086570 | exome | C > T | D1287N | 2 |
| FAT2 | ENSG00000086570 | exome | C > T | G994R | 2 |
| FOXO1 | ENSG00000150907 | RNA-seq | C > T | S203N | 10 |
| FOXO1 | ENSG00000150907 | RNA-seq | T > C | M1V | 10 |
| FOXO1 | ENSG00000150907 | RNA-seq | G > A | T24I | 10 |
| FOXO1 | ENSG00000150907 | RNA-seq | G > T | S193R | 10 |

TABLE 3-continued

Mutations in selected B-cell NHL biomarkers from exome and genome sequencing.

| Gene symbol | Ensembl id | Detection method | Base change | Annotation | Total cSNVs in gene |
|---|---|---|---|---|---|
| FOXO1 | ENSG00000150907 | RNA-seq | T > C | T24A | 10 |
| GNA13 | ENSG00000120063 | RNA-seq | G > A | L296F | 22 |
| GNA13 | ENSG00000120063 | RNA-seq | T > C | K292R | 22 |
| GNA13 | ENSG00000120063 | RNA-seq | T > C | T262A | 22 |
| GNA13 | ENSG00000120063 | RNA-seq | A > G | *378R | 22 |
| GNA13 | ENSG00000120063 | RNA-seq | T > A | K42* | 22 |
| GNA13 | ENSG00000120063 | RNA-seq | T > G | H345P | 22 |
| GNA13 | ENSG00000120063 | RNA-seq | T > C | T203A | 22 |
| GNA13 | ENSG00000120063 | RNA-seq | G > A | S31F | 22 |
| GNA13 | ENSG00000120063 | genome | A > T | I158K | 22 |
| HDAC7 | ENSG00000061273 | genome | G > A | S155F; S194F | 9 |
| HDAC7 | ENSG00000061273 | RNA-seq | C > T | A786T; A788T; A825T | 9 |
| HIST1H1C | ENSG00000187837 | genome | G > C | A185G | 10 |
| HIST1H1C | ENSG00000187837 | genome | C > G | A180P | 10 |
| HIST1H1C | ENSG00000187837 | RNA-seq | G > A | P118S | 10 |
| HIST1H1C | ENSG00000187837 | RNA-seq | C > G | V132L | 10 |
| HIST1H1C | ENSG00000187837 | RNA-seq | G > C | L107V | 10 |
| HIST1H1C | ENSG00000187837 | RNA-seq | C > T | E74K | 10 |
| HIST1H1C | ENSG00000187837 | genome | C > G | G103A | 10 |
| IKZF3 | ENSG00000161405 | RNA-seq | T > G | N73T; N160T | 7 |
| IRF4 | ENSG00000137265 | RNA-seq | G > C | S18T | 9 |
| IRF4 | ENSG00000137265 | RNA-seq | C > G | L40V | 9 |
| IRF4 | ENSG00000137265 | RNA-seq | A > G | I32V | 9 |
| IRF4 | ENSG00000137265 | RNA-seq | A > G | N2S | 9 |
| IRF4 | ENSG00000137265 | RNA-seq | C > A | Q60K | 9 |
| IRF4 | ENSG00000137265 | RNA-seq | C > G | S18R | 9 |
| IRF4 | ENSG00000137265 | RNA-seq | G > C | Q60H | 9 |
| IRF4 | ENSG00000137265 | RNA-seq | A > C | S48R | 9 |
| IRF4 | ENSG00000137265 | RNA-seq | C > A | S48R | 9 |
| IRF8 | ENSG00000140968 | genome | T > G | S55A | 14 |
| IRF8 | ENSG00000140968 | genome | G > C | S34T | 14 |
| IRF8 | ENSG00000140968 | RNA-seq | A > T | *427L | 14 |
| KLHL6 | ENSG00000172578 | genome | C > G | S83T; S94T | 13 |
| KLHL6 | ENSG00000172578 | RNA-seq | G > C | T53S; T64S | 13 |
| KLHL6 | ENSG00000172578 | RNA-seq | A > T | L45*; L56* | 13 |
| KLHL6 | ENSG00000172578 | RNA-seq | G > A | T53I; T64I | 13 |
| KLHL6 | ENSG00000172578 | RNA-seq | G > C | L54V; L65V | 13 |
| MEF2B | ENSG00000064489 | exome | T > C | Y69C | 20 |
| MEF2B | ENSG00000064489 | RNA-seq | T > A | D83V | 20 |
| MEF2B | ENSG00000064489 | RNA-seq | T > A | D83V | 20 |
| MEF2B | ENSG00000064489 | RNA-seq | A > C | L67R | 20 |
| MEF2B | ENSG00000064489 | RNA-seq | A > G | Y69H | 20 |
| MEF2B | ENSG00000064489 | RNA-seq | T > A | D83V | 20 |
| MEF2B | ENSG00000064489 | RNA-seq | T > G | D83A | 20 |
| MEF2B | ENSG00000064489 | RNA-seq | T > A | N81Y | 20 |
| MEF2B | ENSG00000064489 | genome | G > T | N81K | 20 |
| MLL2 | ENSG00000167548 | genome | G > A | Q3391* | 29 |
| MLL2 | ENSG00000167548 | RNA-seq | C > G | A4607P | 29 |
| MLL2 | ENSG00000167548 | RNA-seq | C > T | R2547H | 29 |
| MLL2 | ENSG00000167548 | RNA-seq | G > A | R2250* | 29 |
| MLL2 | ENSG00000167548 | RNA-seq | G > A | P3583S | 29 |
| MLL2 | ENSG00000167548 | RNA-seq | G > A | R4634C | 29 |
| MLL2 | ENSG00000167548 | RNA-seq | G > A | R3956* | 29 |
| MLL2 | ENSG00000167548 | RNA-seq | G > A | Q3333* | 29 |
| MLL2 | ENSG00000167548 | RNA-seq | G > A | R4921* | 29 |
| MLL2 | ENSG00000167548 | RNA-seq | G > A | R2107* | 29 |
| MLL2 | ENSG00000167548 | genome | G > A | Q3394* | 29 |
| MUC16 | ENSG00000181143 | genome | A > G | S2928P | 17 |
| MUC16 | ENSG00000181143 | genome | T > G | S1055R | 17 |
| MUC16 | ENSG00000181143 | genome | G > T | S464Y; S2725Y; S4093Y; S8460Y | 17 |
| MYD88 | ENSG00000172936 | RNA-seq | C > G | S206C | 14 |
| MYD88 | ENSG00000172936 | RNA-seq | T > C | L252P | 14 |
| MYD88 | ENSG00000172936 | RNA-seq | T > C | L252P | 14 |
| MYD88 | ENSG00000172936 | RNA-seq | T > C | L252P | 14 |
| MYD88 | ENSG00000172936 | RNA-seq | T > C | L252P | 14 |
| MYD88 | ENSG00000172936 | RNA-seq | C > G | S206C | 14 |
| MYD88 | ENSG00000172936 | RNA-seq | G > A | S230N | 14 |
| MYD88 | ENSG00000172936 | genome | G > A | S230N | 14 |
| PIM1 | ENSG00000137193 | RNA-seq | C > G | L164V; L255V | 21 |
| PIM1 | ENSG00000137193 | RNA-seq | C > G | L164V; L255V | 21 |
| PIM1 | ENSG00000137193 | RNA-seq | C > G | L25V; L116V | 21 |
| PIM1 | ENSG00000137193 | RNA-seq | C > T | L164F; L255F | 21 |

TABLE 3-continued

Mutations in selected B-cell NHL biomarkers from exome and genome sequencing.

| Gene symbol | Ensembl id | Detection method | Base change | Annotation | Total cSNVs in gene |
|---|---|---|---|---|---|
| PIM1 | ENSG00000137193 | RNA-seq | G > C | E181D; E272D | 21 |
| PIM1 | ENSG00000137193 | RNA-seq | G > A | S97N; S188N | 21 |
| PIM1 | ENSG00000137193 | RNA-seq | G > A | S97N; S188N | 21 |
| PIM1 | ENSG00000137193 | RNA-seq | G > C | E79D; E170D | 21 |
| PIM1 | ENSG00000137193 | RNA-seq | G > C | K24N; K115N | 21 |
| PIM1 | ENSG00000137193 | RNA-seq | C > G | S146R; S237R | 21 |
| PIM1 | ENSG00000137193 | RNA-seq | G > C | Q37H; Q128H | 21 |
| PIM1 | ENSG00000137193 | RNA-seq | C > G | S146R; S237R | 21 |
| PIM1 | ENSG00000137193 | RNA-seq | C > T | L2F; L93F | 21 |
| PIM1 | ENSG00000137193 | RNA-seq | C > G | L2V; L93V | 21 |
| PIM1 | ENSG00000137193 | RNA-seq | G > C | Q37H; Q128H | 21 |
| PLCG2 | ENSG00000197943 | exome | C > A | S16R | 7 |
| PRKDC | ENSG00000121031 | genome | A > C | F1854V | 7 |
| PRKDC | ENSG00000121031 | RNA-seq | A > C | F3973V; F4004V | 7 |
| RAPGEF1 | ENSG00000107263 | RNA-seq | C > T | S53N; S284N; S358N; S375N; S376N | 8 |
| RAPGEF1 | ENSG00000107263 | RNA-seq | A > T | Y265N; Y496N; Y570N; Y587N; Y588N | 8 |
| RAPGEF1 | ENSG00000107263 | RNA-seq | C > G | V16L; V297L; V528L; V602L; V619L; V620L | 8 |
| RAPGEF1 | ENSG00000107263 | genome | A > T | M250K; M481K; M555K; M572K; M573K | 8 |
| RFTN1 | ENSG00000131378 | exome | C > A | S224I | 6 |
| RFTN1 | ENSG00000131378 | RNA-seq | G > A | P205S | 6 |
| RNF213 | ENSG00000173821 | genome | T > A | N2194K | 11 |
| RNF213 | ENSG00000173821 | RNA-seq | G > A | R2286Q | 11 |
| SAMD9 | ENSG00000205413 | genome | T > A | N615Y | 11 |
| SAMD9 | ENSG00000205413 | RNA-seq | A > G | I1578T | 11 |
| SGK1 | ENSG00000118515 | exome | C > G | A105P; A115P; A129P; A210P | 20 |
| SGK1 | ENSG00000118515 | RNA-seq | T > C | R21G; R31G; R45G; R126G | 20 |
| SGK1 | ENSG00000118515 | RNA-seq | C > T | A115E; A125E; A139E; A220E | 20 |
| SGK1 | ENSG00000118515 | RNA-seq | G > T | H153Q; H163Q; H177Q; H258Q | 20 |
| SGK1 | ENSG00000118515 | RNA-seq | G > C | A193G; A203G; A217G; A298G | 20 |
| SGK1 | ENSG00000118515 | RNA-seq | A > T | N34K; N44K; N58K; N139K | 20 |
| SGK1 | ENSG00000118515 | RNA-seq | G > C | F113L; F123L; F137L; F218L | 20 |
| SGK1 | ENSG00000118515 | RNA-seq | C > G | S242T; S252T; S266T; S347T | 20 |
| SGK1 | ENSG00000118515 | RNA-seq | G > A | P67S; P77S; P91S; P172S | 20 |
| SGK1 | ENSG00000118515 | RNA-seq | T > A | K19M; K29M; K43M; K124M | 20 |
| SGK1 | ENSG00000118515 | RNA-seq | G > A | Q30*; Q40*; Q54*; Q135* | 20 |
| SGK1 | ENSG00000118515 | RNA-seq | G > A | T5I | 20 |
| SGK1 | ENSG00000118515 | RNA-seq | C > A | E136*; E146*; E160*; E241* | 20 |
| SGK1 | ENSG00000118515 | RNA-seq | G > A | P65S; P75S; P89S; P170S | 20 |
| SGK1 | ENSG00000118515 | RNA-seq | G > A | P63S; P73S; P87S; P168S | 20 |
| SGK1 | ENSG00000118515 | RNA-seq | C > A | R22M; R32M; R46M; R127M | 20 |
| SGK1 | ENSG00000118515 | RNA-seq | G > T | T229N; T239N; T253N; T334N | 20 |
| SGK1 | ENSG00000118515 | RNA-seq | C > G | R211T; R221T; R235T; R316T | 20 |
| SGK1 | ENSG00000118515 | genome | C > T | C183Y; C193Y; C207Y; C288Y | 20 |
| SGK1 | ENSG00000118515 | genome | G > T | R6S | 20 |
| SGK1 | ENSG00000118515 | genome | C > A | E338*; E348*; E362*; E443* | 20 |
| SGK1 | ENSG00000118515 | genome | G > A | P81L; P91L; P105L; P186L | 20 |
| SGK1 | ENSG00000118515 | genome | G > A | P11L | 20 |
| STAT3 | ENSG00000168610 | exome | G > C | S614R | 9 |
| STAT3 | ENSG00000168610 | RNA-seq | A > T | N567K | 9 |
| STAT3 | ENSG00000168610 | RNA-seq | C > T | E616K | 9 |
| STAT3 | ENSG00000168610 | RNA-seq | C > T | D566N | 9 |
| STAT6 | ENSG00000166888 | exome | G > T | Q286K | 6 |
| STAT6 | ENSG00000166888 | RNA-seq | T > C | D419G | 6 |
| TAF1 | ENSG00000147133 | genome | T > C | L1000P; L1021P | 10 |
| TAF1 | ENSG00000147133 | RNA-seq | T > C | F1047S; F1068S | 10 |
| TMEM30A | ENSG00000112697 | genome | A > T | D155E; D191E | 4 |
| TMEM30A | ENSG00000112697 | genome | A > C | Y157*; Y193* | 4 |
| TMEM30A | ENSG00000112697 | RNA-seq | G > T | S280*; S316* | 4 |
| TMEM30A | ENSG00000112697 | RNA-seq | G > A | R254*; R290* | 4 |
| TMEM30A | ENSG00000112697 | RNA-seq | C > T | W281*; W317* | 4 |
| TNFRSF14 | ENSG00000157873 | RNA-seq | C > T | W12* | 14 |
| TNFRSF14 | ENSG00000157873 | RNA-seq | G > T | C57* | 14 |
| TNFRSF14 | ENSG00000157873 | RNA-seq | G > C | S112C | 14 |
| TNFRSF14 | ENSG00000157873 | RNA-seq | C > T | W201* | 14 |
| TNFRSF14 | ENSG00000157873 | RNA-seq | T > A | N110Y | 14 |
| TNFRSF14 | ENSG00000157873 | RNA-seq | C > T | W12* | 14 |
| TNFRSF14 | ENSG00000157873 | RNA-seq | G > A | Q95* | 14 |
| TNFRSF14 | ENSG00000157873 | RNA-seq | A > G | C53R | 14 |
| TNFRSF14 | ENSG00000157873 | RNA-seq | G > T | Y47* | 14 |
| TNFRSF14 | ENSG00000157873 | genome | C > T | W7* | 14 |
| TNFRSF14 | ENSG00000157873 | genome | C > T | G60D | 14 |
| TP53 | ENSG00000141510 | RNA-seq | C > T | V50M; V143M | 21 |
| TP53 | ENSG00000141510 | RNA-seq | A > C | C83G; C176G | 21 |
| TP53 | ENSG00000141510 | RNA-seq | T > C | Y127C; Y220C | 21 |

TABLE 3-continued

Mutations in selected B-cell NHL biomarkers from exome and genome sequencing.

| Gene symbol | Ensembl id | Detection method | Base change | Annotation | Total cSNVs in gene |
|---|---|---|---|---|---|
| TP53 | ENSG00000141510 | RNA-seq | A > T | Y112N; Y205N | 21 |
| TP53 | ENSG00000141510 | RNA-seq | A > C | Y107D | 21 |
| TP53 | ENSG00000141510 | RNA-seq | T > C | Y141C; Y234C | 21 |
| TP53 | ENSG00000141510 | RNA-seq | A > T | Y141N; Y234N | 21 |
| TP53 | ENSG00000141510 | RNA-seq | G > A | R155W; R248W | 21 |
| TP53 | ENSG00000141510 | RNA-seq | A > C | Y107D | 21 |
| TP53 | ENSG00000141510 | RNA-seq | A > C | S122R; S215R | 21 |
| TP53 | ENSG00000141510 | RNA-seq | A > C | Y107D | 21 |
| TP53 | ENSG00000141510 | RNA-seq | G > A | R155W; R248W | 21 |
| TP53 | ENSG00000141510 | RNA-seq | C > A | G262V | 21 |
| TP53 | ENSG00000141510 | RNA-seq | A > G | F41L; F134L | 21 |
| TP53 | ENSG00000141510 | RNA-seq | C > T | R65H; R158H | 21 |
| TP53 | ENSG00000141510 | RNA-seq | A > C | Y33D; Y126D | 21 |
| TP53 | ENSG00000141510 | RNA-seq | C > T | G152D; G245D | 21 |
| TP53 | ENSG00000141510 | RNA-seq | T > C | T18A | 21 |
| TP53 | ENSG00000141510 | RNA-seq | C > A | C83F; C176F | 21 |
| TP53 | ENSG00000141510 | RNA-seq | T > A | K319* | 21 |
| TP53 | ENSG00000141510 | RNA-seq | G > A | R155W; R248W | 21 |
| TP53 | ENSG00000141510 | RNA-seq | T > C | Y141C; Y234C | 21 |
| TP53 | ENSG00000141510 | RNA-seq | T > A | I255F | 21 |
| TP53 | ENSG00000141510 | RNA-seq | G > A | P278L | 21 |
| TP53 | ENSG00000141510 | RNA-seq | T > A | M144L; M237L | 21 |

TABLE 4

Mutation hotspots in genes identified using RNA-seq.

| Codon | Number of Samples | Distinct mutations | Gene Name |
|---|---|---|---|
| 602; 646 | 30 | 4 | EZH2 |
| 83§ | 9 | 2 | MEF2B |
| 69§ | 4 | 2 | MEF2B |
| 81§ | 2 | 2 | MEF2B |
| 1482§ | 3 | 2 | CREBBP |
| 1499§ | 2 | 2 | CREBBP |
| 1467§ | 2 | 2 | EP300 |
| 287§ | 2 | 1 | HLA-C |
| 1 | 8 | 5 | BCL7A‡ |
| 206§ | 4 | 1 | MYD88‡ |
| 230§ | 2 | 1 | MYD88‡ |
| 252§ | 6 | 1 | MYD88‡ |
| 59 | 7 | 3 | BCL2\* |
| 92; 196; 197 | 5 | 4 | CD79B‡ |
| 73; 160§ | 4 | 2 | IKZF3‡ |
| 164; 255§ | 3 | 2 | PIM1‡ |
| 97; 188 | 3 | 2 | PIM1‡ |
| 18§ | 3 | 2 | IRF4‡ |
| 587§ | 3 | 2 | BCL6 |
| 45§ | 3 | 2 | BTG2‡ |
| 141; 234 | 3 | 2 | TP53‡ |
| 24§ | 2 | 2 | FOXO1‡ |
| 1§ | 3 | 3 | FOXO1‡ |
| 12§ | 2 | 1 | TNFRSF14 |
| 226§ | 2 | 2 | CCND3‡ |
| 233§ | 2 | 2 | CCND3‡ |
| 1§ | 3 | 3 | B2M‡ |

§This mutation was proven to be somatic in at least one case; that is, present in tumour DNA but absent in matched constitutional DNA.
‡Not mutated in any of the fourteen genomes or exomes sequenced.
* Additional hot spots in BCL2 were excluded to simplify the table. Genes indicated in bold are previously described targets of somatic mutation in lymphoma. Although known to be mutated, hot spots have not, to our knowledge, been described in BCL7A. Note that Tyr641 as previously described [13] is based on the Uniprot sequence Q15910, whereas this site corresponds to residue 602 and 646 in the Refseq annotations.

TABLE 5

Mutations affecting CREBBP or EP300 detected using RNA-seq data.

| Library | Disease | Gene | Annotation | EP300 position |
|---|---|---|---|---|
| HS0841 | DLBCL line | CREBBP | E1238*; E1268* | E1202 |
| HS0842 | DLBCL line | CREBBP | A436V | A420 |
| HS0842 | DLBCL line | CREBBP | Q170*; Q238* | not conserved |
| HS0806 | FL | CREBBP | Y71H; Y1482H; Y1512H§ | Y1446 |
| HS1185 | FL | CREBBP | G1411E; G1441E | G1375 |
| HS1200 | FL | CREBBP | Y92F; Y1503F; Y1533F | Y1467 |
| HS1360 | FL | CREBBP | R35C; R1446C; R1476C | R1410 |
| HS1361 | FL | CREBBP | S25N; S1436N; S1466N§ | S1400 |
| HS0637 | DLBCL | CREBBP | Q1104*; Q1134* | Q1068 |
| HS0641 | DLBCL | CREBBP | L88Q; L1499Q; L1529Q§ | L1463 |
| HS0649 | DLBCL | CREBBP | P77R; P1488R; P1518R§ | P1452 |
| HS0649 | DLBCL | CREBBP | A687V; A717V | not conserved |
| HS0749 | DLBCL | CREBBP | N1589K; N1619K | N1552 |
| HS0933 | DLBCL | CREBBP | R370*; R438* | R354 |
| HS0939 | DLBCL | CREBBP | M1625V; M1655V§ | M1588 |
| HS1135 | DLBCL | CREBBP | V1342E; V1372E | V1306 |
| HS1460 | DLBCL | CREBBP | L88P; L1499P; L1529P§ | L1463 |
| HS1977 | DLBCL | CREBBP | C1283R; C1313R | C1247 |
| HS1979 | DLBCL | CREBBP | N513S; N1978S; N2008S | not conserved |
| HS2059 | DLBCL | CREBBP | Y71N; Y1482N; Y1512N§ | Y1446 |
| HS2249 | DLBCL | CREBBP | A442T; A1907T; A1937T | not conserved |
| HS2249 | DLBCL | CREBBP | Y92H; Y1503H; Y1533H§ | Y1467 |
| HS2606 | DLBCL | CREBBP | R35C; R1446C; R1476C§ | R1410 |
| HS0653 | DLBCL | EP300 | Q1904* | — |
| HS0939 | DLBCL | EP300 | A1498T§ | — |
| HS1133 | DLBCL | EP300 | L415P | |

TABLE 5-continued

Mutations affecting CREBBP or EP300 detected using RNA-seq data.

| Library | Disease | Gene | Annotation | EP300 position |
|---|---|---|---|---|
| HS1462 | DLBCL | EP300 | Y1467H[§] | — |
| HS2049 | DLBCL | EP300 | P925T[‡] | — |
| HS2607 | DLBCL | EP300 | P925T[‡] | — |
| HS1199 | FL | EP300 | D1485V | — |
| HS1201 | FL | EP300 | Q1455L | — |
| HS1202 | FL | EP300 | Y1467N[§] | — |
| HS0841 | DLBCL line | EP300 | Q160* | — |
| HS0900 | DLBCL line | EP300 | R1627W | — |

[§] mutation was proven to be somatic (absent in matched constitutional DNA);
[‡] was also found in the matched constitutional DNA (inherited variant); bold indicates mutation hot spots.

TABLE 6

Mutations in MLL2 found by targeted MLL2 resequencing.

| Chromosome locus | Mutation | Event | Lymphoma | Somatic status |
|---|---|---|---|---|
| chr12:47731299 | GAG > TAG | E812* | FL | somatic |
| chr12:47720827 | -A | Frameshift deletion | FL | somatic |
| chr12:47731577 | -GCTGGAGGAGTCACCC (SEQ ID NO: 2) | Frameshift deletion | FL | somatic |
| chr12:47719922 | TCA > TAA | S2633* | FL | somatic |
| chr12:47728117 | -AT | Frameshift deletion | FL | somatic |
| chr12:47718602 | TCA > TGA | S2935* | FL | somatic |
| chr12:47706246 | GAC > GTC | D5257V_FYRC domain | FL | somatic |
| chr12:47706727 | CGA > TGA | R5097* | FL | somatic |
| chr12:47719661 | CGA > TGA | R2685* | FL | somatic |
| chr12:47731461 | GAG > TAG | E758* | FL | somatic |
| chr12:47733524 | T > C | SS end6 | FL | somatic |
| chr12:47729734 | CAG > TAG | Q1302* | FL | somatic |
| chr12:47719040 | G > A | SS beg34 | FL | somatic |
| chr12:47721300 | CAG > TAG | Q2174* | FL | somatic |
| chr12:47728117 | -AT | Frameshift deletion | FL | somatic |
| chr12:47707855 | CAG > TAG | Q4881* | FL | somatic |
| chr12:47718680 | -AAGT | Frameshift deletion | FL | somatic |
| chr12:47717409 | CAG > TAG | Q3333* | FL | somatic |
| chr12:47724315 | -CA | Frameshift deletion ++ | FL | somatic |
| chr12:47711008 | CGA > TGA | R4536* | FL | somatic |
| chr12:47734195 | -GCAGCGCTG | Frameshift deletion (SSbeg5) | FL | somatic |
| chr12:47711624 | TGG > TGA | W4377* | FL | somatic |
| chr12:47719271 | G > A | SS end33 | FL | somatic |
| chr12:47718918 | CGA > TGA | R2830* | FL | somatic |
| chr12:47713018 | CAG > TAG | Q3913* | FL | somatic |
| chr12:47720103 | -G | Frameshift deletion ++ | FL | somatic |
| chr12:47702684 | CGG > TGG | R5432W_SET domain | FL | somatic |
| chr12:47713509 | -ACAG | Frameshift deletion | FL | somatic |
| chr12:47731159 | +T | Frameshift insertion | FL | somatic |

TABLE 6-continued

Mutations in MLL2 found by targeted MLL2 resequencing.

| Chromosome locus | Mutation | Event | Lymphoma | Somatic status |
|---|---|---|---|---|
| chr12:47717445 | CGA > TGA | R3321* | FL | somatic |
| chr12:47709482 | +AT | Frameshift insertion | FL | somatic |
| chr12:47714889 | -G +TA | Frameshift in-del | FL | somatic |
| chr12:47717767 | +T | Frameshift deletion | FL | somatic |
| chr12:47722866 | CGA > TGA | R1903* | FL | somatic |
| chr12:47720228 | -C | Frameshift deletion | FL | somatic |
| chr12:47704937 | CGA > TGA | R5282* | FL | undetermined |
| chr12:47726475 | G > A | SS beg16 | FL | undetermined |
| chr12:47702165 | -CG +T | Frameshift deletion in-del | FL | undetermined |
| chr12:47713960 | CAG > TAG | Q3599* | FL | undetermined |
| chr12:47713064 | +T | Frameshift insertion | FL | undetermined |
| chr12:47723788 | -C | Frameshift deletion | FL | undetermined |
| chr12:47704873 | CGC > CAC | R5303H_FYRC domain | FL | undetermined |
| chr12:47719320 | +CGACTCT | Frameshift insertion | FL | undetermined |
| chr12:47702170 | -TG | Frameshift deletion | FL | undetermined |
| chr12:47718081 | +G | Frameshift insertion | FL | undetermined |
| chr12:47704646 | +G | Frameshift insertion | FL | undetermined |
| chr12:47714203 | +A | Frameshift insertion | FL | undetermined |
| chr12:47718680 | -AAGT | Frameshift deletion | GCB-DLBCL | somatic |
| chr12:47726113 | T > G | SS end17 | GCB-DLBCL | somatic |
| chr12:47730448 | +G | Frameshift insertion | GCB-DLBCL | somatic |
| chr12:47724460 | TAT > TAA | Y1692* | GCB-DLBCL | somatic |
| chr12:47712844 | CAA > TAA | Q3971* | GCB-DLBCL | somatic |
| chr12:47724319 | -A | Frameshift deletion | ABC-DLBCL | somatic |
| chr12:47706936 | CGA > CAA | R5027L_FYRC domain | GCB-DLBCL | somatic |
| chr12:47723144 | -ACAG | Frameshift deletion | GCB-DLBCL | undetermined |
| chr12:47710329 | G > A | SS end42 | GCB-DLBCL | undetermined |
| chr12:47719628 | CAG > TAG | Q2696* | GCB-DLBCL | somatic |
| chr12:47732160 | -AG | Frameshift deletion | GCB-DLBCL | undetermined |
| chr12:47718251 | -TA | Frameshift deletion | GCB-DLBCL | somatic |
| chr12:47719327 | CGA > TGA | R2771* | ABC-DLBCL | somatic |
| chr12:47710444 | +C | Frameshift insertion | ABC-DLBCL | undetermined |
| chr12:47709214 | -G | Frameshift deletion | GCB-DLBCL | somatic |
| chr12:47733683 | CGC > GGC | R228G_PHD domain | GCB-DLBCL | undetermined |
| chr12:47719508 | CAG > TAG | Q2736* | GCB-DLBCL[cl] | cell line |
| chr12:47732295 | -C | Frameshift deletion | GCB-DLBCL[cl] | cell line |
| chr12:47717574 | CAA > TAA | Q3278* | GCB-DLBCL[cl] | cell line |

TABLE 6-continued

Mutations in MLL2 found by targeted MLL2 resequencing.

| Chromosome locus | Mutation | Event | Lymphoma | Somatic status |
|---|---|---|---|---|
| chr12:47717760 | GAG > TAG | E3216* | ABC-DLBCL[cl] | cell line |
| chr12:47720598 | +A | Frameshift insertion | ABC-DLBCL[cl] | cell line |
| chr12:47702767 | TCC > TTC | S5404F_SET domain | GBC-DLBCL[cl] | cell line |
| chr12:47712865 | CAG > TAG | Q3964* | ABC-DLBCL[cl] | cell line |
| chr12:47729996 | -G | Frameshift deletion | ABC-DLBCL[cl] | cell line |
| chr12:47722866 | CGA > TGA | A1903* | GBC-DLBCL[cl] | cell line |
| chr12:47707230 | -C | Frameshift deletion | GBC-DLBCL[cl] | cell line |
| chr12:47717493 | -GTTTGGCTGGGTCCCA (SEQ ID NO: 3) | Frameshift deletion ++ | GBC-DLBCL[cl] | cell line |
| chr12:47734070 | CAG > TAG | Q211* | GCB-DLBCL[cl] | cell line |
| chr12:47709228 | GAG > TAG | E4712* | GBC-DLBCL[cl] | cell line |
| chr12:47731793 | +C | Frameshift insertion ++ | ABC-DLBCL[cl] | cell line |
| chr12:47706741 | TGC > TAC | C5092Y_PHD domain | GBC-DLBCL[cl] | cell line |

Additional mutations at splice sites in MLL2 detected by Trans-ABySS

| chr12:47733693 | T > G | SS end38 | DLBCL | n/a |
| chr12:47714115 | T > G | SS beg6 | DLBCL | n/a |

++ homozygous mutations; SS Splice site mutations;
*not detected by RNA-seq automated analysis;
** indels and mutations at splice sites were not part of our automated analysis of RNA-seq, n/a refers to samples for which either RNA-seq or targeted resequencing was not performed.

TABLE 7

All MEF2B mutations detected.

| Case (res_id) | Position (chromosome) | Change (DNA) | Change (protein) | Diagnosis and subtype (subtyping method) |
|---|---|---|---|---|
| 03-31934 | chr19:19122543 | T > A | M1K | FL |
| 02-17440 | chr19:19122535 | A > G | K4E | GCB DLBCL (GEP) |
| 98-17403 | chr19:19122535 | A > G | K4E | DLBCL |
| 06-20044 | chr19:19122535[§] | A > G | K4E | FL |
| 06-23741 | chr19:19122535[§] | A > G | K4E | FL |
| 07-14540 | chr19:19122535 | A > G | K4E | FL |
| 98-14740 | chr19:19122535 | A > G | K4E | FL |
| 05-15463 | chr19:19122532 | A > G | K5E | FL |
| 03-28045 | chr19:19122523 | A > G | I8V | DLBCL |
| 92-59893 | chr19:19122502 | A > G | R15G | DLBCL |
| 02-28712 | chr19:19122492 | C > T | Q18* | DLBCL |
| 05-22052 | chr19:19121225 | A > G | K23R | DLBCL |
| 07-10201 | chr19:19121222 | G > A | R24Q | FL |
| SPEC1187 | chr19:19121217 | T > G | F26V | GCB DLBCL (GEP) |
| 06-20952 | chr19:19121195 | A > C | Y33S | FL |
| 03-18669 | chr19:19121153 | T > C | I47T | DLBCL |
| 03-33888 | chr19:19121135 | G > A | R53H | DLBCL |

TABLE 7-continued

All MEF2B mutations detected.

| Case (res_id) | Position (chromosome) | Change (DNA) | Change (protein) | Diagnosis and subtype (subtyping method) |
|---|---|---|---|---|
| 01-16433 | chr19:19121093[§] | T > G | L67R | FL |
| 00-15694 | chr19:19121088[§] | A > G | Y69H | GCB DLBCL (GEP) |
| 05-11328 | chr19:19121088 | A > G | Y69H | GCB DLBCL (GEP) |
| 06-12968 | chr19:19121087[§] | T > C | Y69O | FL |
| 06-18193 | chr19:19121087 | T > C | Y69O | FL |
| 08-10448 | chr19:19121087 | T > C | Y69O | FL |
| 99-30068 | chr19:19121087 | T > C | Y69O | FL |
| 05-11369 | chr19:19121066 | -GGGGCT | E74-P75-H76 > D | FL |
| 06-23851 | chr19:19121066 | A > G | H76R | FL |
| 07-21828 | chr19:19121064 | G > A | E77K | DLBCL |
| 07-30109 | chr19:19121063 | A > G | E77G | Composite FL |
| 06-30145 | chr19:19121052[§] | A > T | N81Y | GCB DLBCL (GEP) |
| 05-23110 | chr19:19121050[§] | C > A | N81K | GCB DLBCL (GEP) |
| 00-13940 | chr19:19121045 | T > G | D83A | GCB DLBCL (IHC) |
| 06-15922 | chr19:19121045[§] | T > G | D83A | GCB DLBCL (GEP) |
| 07-23804 | chr19:19121045 | T > G | D83A | GCB DLBCL (GEP) |
| 00-22287 | chr19:19121045 | T > A | D83V | GCB DLBCL (IHC) |
| 01-18672 | chr19:19121045 | T > A | D83V | GCB DLBCL (IHC) |
| 02-30647 | chr19:19121045 | T > A | D83V | GCB DLBCL (GEP) |
| 03-11110 | chr19:19121045 | T > A | D83V | DLBCL |
| 03-26817 | chr19:19121045 | T > A | D83V | GCB DLBCL (GEP) |
| 03-30438 | chr19:19121045 | T > A | D83V | GCB DLBCL (GEP) |
| 05-24666 | chr19:19121045 | T > A | D83V | GCB DLBCL (GEP) |
| 06-30025 | chr19:19121045[§] | T > A | D83V | GCB DLBCL (GEP) |
| 06-33777 | chr19:19121045[§] | T > A | D83V | GCB DLBCL (GEP) |
| 78-60284 | chr19:19121045 | T > A | D83V | GCB DLBCL (IHC) |
| 95-32814 | chr19:19121045[§] | T > A | D83V | GCB DLBCL (GEP) |
| 97-10270 | chr19:19121045 | T > A | D83V | DLBCL |
| DB (cell line) | chr19:19121045 | T > A | D83V | GCB DLBCL (GEP) |
| 06-11109 | chr19:19121045 | T > G | D83A | FL |
| 07-20462 | chr19:19121045 | T > G | D83A | FL |
| 91-34915 | chr19:19121045 | T > G | D83A | FL |
| 03-16286 | chr19:19121045 | T > C | D83G | FL |
| 05-12024 | chr19:19121045 | T > A | D83V | FL |
| 06-22766 | chr19:19121045 | T > A | D83V | FL |
| 06-33903 | chr19:19121045 | T > A | D83V | FL |
| 89-30159 | chr19:19121045 | T > A | D83V | FL |

TABLE 7-continued

All MEF2B mutations detected.

| Case (res_id) | Position (chromosome) | Change (DNA) | Change (protein) | Diagnosis and subtype (subtyping method) |
|---|---|---|---|---|
| 91-53679 | chr19:19121045 | T > A | D83V | FL |
| 97-23234 | chr19:19121045 | T > A | D83V | FL |
| 99-21548 | chr19:19121045 | T > A | D83V | FL |
| 01-24821 | chr19:19119600 | +A | L100 Frameshift | FL |
| 85-31959 | chr19:19119578 | C > A | E108* | FL |
| 06-16716 | chr19:19119559‡ | C > T | R114Q | ABC DLBCL (GEP) |
| 02-18484 | chr19:19119539 | 10 bp del | G121 Frameshift | FL |
| 91-53679 | chr19:19118877 | -GGAA | F170 Frameshift | FL |
| 08-15460 | chr19:19118875 | -AAGG | P169 Frameshift | DLBCL |
| 06-10398 | chr19:19118406 | +GG | G242 Frameshift | ABC DLBCL (GEP) |
| 06-30389 | chr19:19118365 | -C | P256 Frameshift | FL |
| 07-18609 | chr19:19117831 | A > C | S294R† | FL |
| 05-20543 | chr19:19117794 | G > T | R307S† | ABC DLBCL (GEP) |
| 05-14545 | chr19:19117608 | A > G | *369G† | FL |
| 06-23851 | chr19:19117608 | A > C | *369E† | FL |
| 06-12557 | chr19:19117606 | C > G | *369Y† | FL |

† annotation is unique to NM_001145785, representing the longest MEF2B isoform,
§ was proven to be somatic (absent in matched constitutional DNA);
‡ was also found in the matched constitutional DNA (inherited variant).

TABLE 8

Catalogue of MEF2B cSNVs in FL and DLBCL.

| Amino Acid Change | FL | DLBCL | Total | % variants |
|---|---|---|---|---|
| M1K | 1 | 0 | 1 | 1.4 |
| K4E§ | 4 | 2 | 6 | 8.7 |
| K5E | 1 | 0 | 1 | 1.4 |
| I8V | 0 | 1 | 1 | 1.4 |
| R15G | 0 | 1 | 1 | 1.4 |
| K23R | 0 | 1 | 1 | 1.4 |
| R24Q | 1 | 0 | 1 | 1.4 |
| F26V | 0 | 1 | 1 | 1.4 |
| Y33S | 1 | 0 | 1 | 1.4 |
| I47T | 0 | 1 | 1 | 1.4 |
| R53H | 0 | 1 | 1 | 1.4 |
| L67R | 1 | 0 | 1 | 1.4 |
| Y69C/H§ | 4 | 2 | 6 | 8.7 |
| E74-P75-H76 > D | 1 | 0 | 1 | 1.4 |
| H76R | 1 | 0 | 1 | 1.4 |
| E77K | 0 | 1 | 1 | 1.4 |
| N81K/Y§ | 0 | 2 | 2 | 2.9 |
| D83A/G/V§ | 11 | 16 | 27 | 39.1 |
| R114Q | 0 | 1 | 1 | 1.4 |
| S294Y | 1 | 0 | 1 | 1.4 |
| R307S | 0 | 1 | 1 | 1.4 |
| *369Y/E/G | 3 | 0 | 3 | 4.3 |
| Truncation | 5 | 3 | 8 | 11.6 |
| Any mutation | 35 | 34 | 69 | 100.0 |
| Total cases sequenced | 261 | 292 | | |
| Prevalence | 13.41% | 11.64% | | |

§ at least one representative mutation at this position has been confirmed as a somatic mutation.

TABLE 9

All cSNVs detected in 10 DLBCL cell lines using RNA-seq data.

| Gene name | Ensembl gene | Mutation | Effect (all isoforms) | Cell Line |
|---|---|---|---|---|
| HLA-C | ENSG00000204525 | C > G | W188S; W191S | OCI-Ly19 |
| AFF1 | ENSG00000172493 | C > T | P866P | OCI-Ly7 |
| AQR | ENSG00000021776 | G > C | A1013G | DB |

TABLE 9-continued

All cSNVs detected in 10 DLBCL cell lines using RNA-seq data.

| Gene name | Ensembl gene | Mutation | Effect (all isoforms) | Cell Line |
|---|---|---|---|---|
| ASCC3L1 | ENSG00000144028 | T > C | M387V | OCI-Ly1 |
| ASCC3L1 | ENSG00000144028 | T > C | N313D | OCI-Ly7 |
| BCL2 | ENSG00000171791 | G > A | N172N | DB |
| BCL2 | ENSG00000171791 | G > A | L119L | DB |
| BCL2 | ENSG00000171791 | C > G | R183R | Karpas422 |
| BCL2 | ENSG00000171791 | G > A | P59L | Karpas422 |
| BCL2 | ENSG00000171791 | C > T | G47D | Karpas422 |
| BCL2 | ENSG00000171791 | C > T | R63R | NU-DHL-1 |
| BCL2 | ENSG00000171791 | C > T | A2T | NU-DHL-1 |
| BCL2 | ENSG00000171791 | C > T | L72L | SU-DHL-6 |
| BCL2 | ENSG00000171791 | C > T | P71P | SU-DHL-6 |
| BCL2 | ENSG00000171791 | T > A | I48F | SU-DHL-6 |
| BCL2 | ENSG00000171791 | T > G | T69P | WSU-DLCL2 |
| BCL2 | ENSG00000171791 | C > G | E13D | WSU-DLCL2 |
| BCL2 | ENSG00000171791 | G > A | T187I | OCI-Ly1 |
| BCL2 | ENSG00000171791 | G > A | S161S | OCI-Ly1 |
| BCL2 | ENSG00000171791 | G > A | A131V | OCI-Ly1 |
| BCL2 | ENSG00000171791 | G > A | S87S | OCI-Ly1 |
| BCL2 | ENSG00000171791 | C > T | A85A | OCI-Ly1 |
| BCL2 | ENSG00000171791 | A > G | F49L | OCI-Ly1 |
| BCL2 | ENSG00000171791 | A > G | H20H | OCI-Ly1 |
| BCL2 | ENSG00000171791 | A > G | D10D | OCI-Ly1 |
| BCL2 | ENSG00000171791 | C > T | G5G | OCI-Ly1 |
| BCL6 | ENSG00000113916 | G > T | A587D | OCI-Ly7 |
| BCL6 | ENSG00000113916 | T > G | N588H | OCI-Ly19 |
| BCL7A | ENSG00000110987 | T > G | M1R | OCI-Ly1 |
| BCL7A | ENSG00000110987 | C > T | R29C | OCI-Ly7 |
| CARD11 | ENSG00000198286 | C > T | D223N; D230N; D247N | Karpas422 |
| CARS | ENSG00000110619 | G > A | H147H; H157H; H240H | OCI-Ly7 |
| CCND3 | ENSG00000112576 | G > A | P234S; P280S; P284S | NU-DHL-1 |
| CCND3 | ENSG00000112576 | T > C | T233A; T279A; T283A | OCI-Ly7 |
| CCND3 | ENSG00000112576 | C > G | A239P; A285P; A289P | OCI-Ly19 |
| CENPP | ENSG00000188312 | G > A | R141H; R182H | NU-DUL-1 |
| CREBBP | ENSG00000005339 | C > A | E1238*; E1268* | Karpas422 |
| CREBBP | ENSG00000005339 | G > A | A436V | NU-DHL-1 |
| CREBBP | ENSG00000005339 | G > A | Q170*; Q238* | NU-DHL-1 |
| CSTF2T | ENSG00000177613 | T > A | L428F | DOHH-2 |
| DBN1 | ENSG00000113758 | C > T | R226Q; R228Q | DB |
| DDX56 | ENSG00000136271 | G > A | L14L | WSU-DLCL2 |
| EGLN1 | ENSG00000135766 | T > G | S166R | OCI-Ly19 |
| EZH2 | ENSG00000106462 | A > T | Y602N; Y646N | DB |
| EZH2 | ENSG00000106462 | A > T | Y602N; Y646N | Karpas422 |
| EZH2 | ENSG00000106462 | A > T | Y602N; Y646N | SU-DHL-6 |
| EZH2 | ENSG00000106462 | T > A | Y602F; Y646F | WSU-DLCL2 |
| EZH2 | ENSG00000106462 | A > T | Y602N; Y646N | OCI-Ly1 |
| FAT4 | ENSG00000196159 | C > A | I1760I; I3462I | Karpas422 |
| FOXO1 | ENSG00000150907 | T > C | I10V | OCI-Ly1 |
| FOXO1 | ENSG00000150907 | T > A | M1L | OCI-Ly1 |
| GCN1L1 | ENSG00000089154 | A > G | L2229L | OCI-Ly1 |
| GNA13 | ENSG00000120063 | G > C | Y89* | DOHH-2 |
| GNA13 | ENSG00000120063 | T > G | Y308S | SU-DHL-6 |
| GNA13 | ENSG00000120063 | A > G | F245S | WSU-DLCL2 |
| GNA13 | ENSG00000120063 | A > T | L197Q | OCI-Ly1 |
| GNA13 | ENSG00000120063 | A > G | I34T | OCI-Ly1 |
| GTF3C1 | ENSG00000077235 | C > T | R403Q; R405Q | OCI-Ly7 |
| HNRNPA1 | ENSG00000135486 | T > G | G234G | OCI-Ly19 |
| IFNGR2 | ENSG00000159128 | A > C | I77L; I156L; I175L | OCI-Ly1 |
| IKZF3 | ENSG00000161405 | T > C | N73S; N160S | DOHH-2 |
| IKZF3 | ENSG00000161405 | A > C | L75R; L162R | NU-DUL-1 |
| LSP1 | ENSG00000130592 | G > A | R187H; R249H; R253H; R256H; R377H | WSU-DLCL2 |
| MAST1 | ENSG00000105613 | G > A | A74T | DB |
| MEF2B | ENSG00000064489 | T > A | D83V | DB |
| MEF2C | ENSG00000081189 | A > G | Y69H | DB |
| MEF2C | ENSG00000081189 | T > G | E14A | OCI-Ly1 |
| MEF2C | ENSG00000081189 | T > G | K5T | OCI-Ly1 |
| MKI67 | ENSG00000148773 | T > G | K617N; K977N | SU-DHL-6 |
| MLL2 | ENSG00000167548 | C > A | L3496L | DB |
| MLL2 | ENSG00000167548 | G > A | Q2156* | DB |
| MLL2 | ENSG00000167548 | G > A | S4824F | NU-DHL-1 |
| MLL2 | ENSG00000167548 | G > A | R1323* | OCI-Ly1 |
| MLL2 | ENSG00000167548 | G > A | Q3384* | NU-DUL-1 |
| MLL2 | ENSG00000167548 | C > A | D635Y | NU-DUL-1 |
| NCKAP1L | ENSG00000123338 | A > G | V105V | OCI-Ly19 |
| PCDHGC5 | ENSG00000081853 | A > G | L726L | WSU-DLCL2 |
| PLCG2 | ENSG00000197943 | C > T | G426G | OCI-Ly7 |
| PRDM15 | ENSG00000141956 | G > C | L361V; L398V; L727V | SU-DHL-6 |

TABLE 9-continued

All cSNVs detected in 10 DLBCL cell lines using RNA-seq data.

| Gene name | Ensembl gene | Mutation | Effect (all isoforms) | Cell Line |
|---|---|---|---|---|
| PSAP | ENSG00000197746 | A > T | L260H | WSU-DLCL2 |
| RBM39 | ENSG00000131051 | A > G | I240T; I247T; I397T | OCI-Ly7 |
| RFTN1 | ENSG00000131378 | T > A | H83L | OCI-Ly1 |
| RFXDC2 | ENSG00000181827 | C > T | W685* | NU-DUL-1 |
| RNF14 | ENSG00000013561 | G > T | Q133H; Q259H | OCI-Ly1 |
| SMG6 | ENSG00000070366 | G > A | R767C | OCI-Ly1 |
| SOS2 | ENSG00000100485 | T > C | S271G | Karpas422 |
| SPTBN1 | ENSG00000115306 | C > A | D1318E; D1331E; D1344E | DB |
| STAT6 | ENSG00000166888 | T > C | Q286R | NU-DHL-1 |
| STAT6 | ENSG00000166888 | C > G | G375R | OCI-Ly1 |
| TNFAIP3 | ENSG00000118503 | G > A | G367G | DOHH-2 |
| TP53 | ENSG00000141510 | G > A | R155W; R248W | DB |
| TP53 | ENSG00000141510 | T > A | K319* | Karpas422 |
| TP53 | ENSG00000141510 | T > C | Y141C; Y234C | SU-DHL-6 |
| TP53 | ENSG00000141510 | A > C | C83G; C176G | OCI-Ly1 |
| TP53 | ENSG00000141510 | C > T | R65H; R158H | OCI-Ly1 |
| TP53 | ENSG00000141510 | C > T | G152D; G245D | OCI-Ly7 |
| TP53 | ENSG00000141510 | C > T | V50M; V143M | NU-DUL-1 |
| TSEN54 | ENSG00000182173 | C > T | R490W | OCI-Ly1 |
| TSEN54 | ENSG00000182173 | G > C | G525A | OCI-Ly1 |
| USP34 | ENSG00000115464 | T > A | S1685S; S1837S | SU-DHL-6 |
| ZMYND8 | ENSG00000101040 | C > G | V518L; V537L; V538L; V543L; V563L | OCI-Ly7 |

CITATIONS FOR REFERENCES REFERRED TO IN THE SPECIFICATION

1. Anderson, J. R., Armitage, J. O. & Weisenburger, D. D. Epidemiology of the non-Hodgkin's lymphomas: distributions of the major subtypes differ by geographic locations. Non-Hodgkin's Lymphoma Classification Project. Ann. Oncol. 9, 717-720 (1998).
2. Lenz, G. & Staudt, L. M. Aggressive lymphomas. N Engl J Med 362, 1417-1429 (2010).
3. Horsman, D. E. et al. Follicular lymphoma lacking the t(14;18)(q32;q21): identification of two disease subtypes. Br J Haematol 120, 424-433 (2003).
4. Iqbal, J. et al. BCL2 translocation defines a unique tumor subset within the germinal center B-cell-like diffuse large B-cell lymphoma. Am J Pathol 165, 159-166 (2004).
5. Lenz, G. et al. Molecular subtypes of diffuse large B-cell lymphoma arise by distinct genetic pathways. Proc Natl Acad Sci USA 105, 13520-13525 (2008).
6. Pasqualucci, L. et al. Inactivation of the PRDM1/BLIMP1 gene in diffuse large B cell lymphoma. J Exp Med 203, 311-317 (2006).
7. Kato, M. et al. Frequent inactivation of A20 in B-cell lymphomas. Nature 459, 712-716 (2009).
8. Compagno, M. et al. Mutations of multiple genes cause deregulation of NF-kappaB in diffuse large B-cell lymphoma. Nature 459, 717-721 (2009).
9. Davis, R. E. et al. Chronic active B-cell-receptor signalling in diffuse large B-cell lymphoma. Nature 463, 88-92 (2010).
10. Ngo, V. N. et al. Oncogenically active MYD88 mutations in human lymphoma. Nature 470, 115-119 (2011).
11. Mardis, E. R. et al. Recurring mutations found by sequencing an acute myeloid leukemia genome. N Engl J Med 361, 1058-1066 (2009).
12. Shah, S. P. et al. Mutational evolution in a lobular breast tumour profiled at single nucleotide resolution. Nature 461, 809-813 (2009).
13. Morin, R. D. et al. Somatic mutations altering EZH2 (Tyr641) in follicular and diffuse large B-cell lymphomas of germinal-center origin. Nat Genet 42, 181-185 (2010).
14. Futreal, P. A. et al. A census of human cancer genes. Nat Rev Cancer 4, 177-183 (2004).
15. Pasqualucci, L. et al. Inactivating mutations of acetyltransferase genes in B-cell lymphoma. Nature 471, 189-195 (2011).
16. Yusuf, I., Zhu, X., Kharas, M. G., Chen, J. & Fruman, D. A. Optimal B-cell proliferation requires phosphoinositide 3-kinase-dependent inactivation of FOXO transcription factors. Blood 104, 784-787 (2004).
17. Saito, M. et al. BCL6 suppression of BCL2 via Miz1 and its disruption in diffuse large B cell lymphoma. Proc Natl Acad Sci USA 106, 11294-11299 (2009).
18. Lenz, G. et al. Oncogenic CARD11 mutations in human diffuse large B cell lymphoma. Science 319, 1676-1679 (2008).
19. Greenman, C., Wooster, R., Futreal, P. A., Stratton, M. R. & Easton, D. F. Statistical analysis of pathogenicity of somatic mutations in cancer. Genetics 173, 2187-2198 (2006).
20. Cheung, K. J. et al. Acquired TNFRSF14 mutations in follicular lymphoma are associated with worse prognosis. Cancer Res 70, 9166-9174 (2010).
21. Du, M. Q. et al. BCL10 gene mutation in lymphoma. Blood 95, 3885-3890 (2000).
22. Kreutz, B., Hajicek, N., Yau, D. M., Nakamura, S. & Kozasa, T. Distinct regions of Galpha13 participate in its regulatory interactions with RGS homology domain-containing RhoGEFs. Cell Signal 19, 1681-1689 (2007).
23. Bhattacharyya, R. & Wedegaertner, P. Galpha 13 requires palmitoylation for plasma membrane localization, Rho-dependent signaling, and promotion of p115-RhoGEF membrane binding. J Biol Chem 275, 14992-14999 (2000).
24. Manganello, J. M., Huang, J., Kozasa, T., Voyno-Yasenetskaya, T. A. & Le Breton, G. C. Protein kinase A-mediated phosphorylation of the Galpha13 switch I region alters the Galphabetagamma13-G protein-coupled receptor complex and inhibits Rho activation. J Biol Chem 278, 124-130 (2003).
25. Brunet, A. et al. Protein Kinase SGK Mediates Survival Signals by Phosphorylating the Forkhead Transcription Factor FKHRL1 (FOXO3a). Mol Cell Biol 21, 952-965 (2001).

26. Tai, D. J. C., Su, C., Ma, Y. & Lee, E. H. Y. SGK1 phosphorylation of IkappaB Kinase alpha and p300 Up-regulates NF-kappaB activity and increases N-Methyl-D-aspartate receptor NR2A and NR2B expression. *J Biol Chem* 284, 4073-4089 (2009).

27. Mo, J. et al. Serum- and glucocorticoid-inducible kinase 1 (SGK1) controls Notch1 signaling by downregulation of protein stability through Fbw7 ubiquitin ligase. *J Cell Sci* 124, 100-112 (2011).

28. Young, K. H. et al. Structural profiles of TP53 gene mutations predict clinical outcome in diffuse large B-cell lymphoma: an international collaborative study. *Blood* 112, 3088-3098 (2008).

29. Shilatifard, A. Molecular implementation and physiological roles for histone H3 lysine 4 (H3K4) methylation. *Current Opinion in Cell Biology* 20, 341-348 (2008).

30. Milne, T. et al. MLL Targets SET Domain Methyltransferase Activity to Hox Gene Promoters. *Mol Cell* 10, 1107-1117 (2002).

31. Krumlauf, R. Hox genes in vertebrate development. *Cell* 78, 191-201 (1994).

32. Canaani, E. et al. ALL-1//MLL1, a homologue of Drosophila TRITHORAX, modifies chromatin and is directly involved in infant acute leukaemia. *Br J Cancer* 90, 756-760 (2004).

33. Wiedemann, L. et al. Global Analysis of H3K4 Methylation Defines MLL Family Member Targets and Points to a Role for MLL1-Mediated H3K4 Methylation in the Regulation of Transcriptional Initiation by RNA Polymerase II. *Mol Cell Biol* 29, 6074-6085 (2009).

34. Issaeva, I. et al. Knockdown of ALR (MLL2) Reveals ALR Target Genes and Leads to Alterations in Cell Adhesion and Growth. *Mol Cell Biol* 27, 1889-1903 (2007).

35. Pleasance, E. D. et al. A small-cell lung cancer genome with complex signatures of tobacco exposure. *Nature* 463, 184-190 (2010).

36. Dalgliesh, G. L. et al. Systematic sequencing of renal carcinoma reveals inactivation of histone modifying genes. *Nature* 463, 360-363 (2010).

37. Parsons, D. W. et al. The Genetic Landscape of the Childhood Cancer Medulloblastoma. *Science* 331, 435-439 (2011).

38. Iqbal, J. et al. Distinctive patterns of BCL6 molecular alterations and their functional consequences in different subgroups of diffuse large B-cell lymphoma. *Leukemia* 21, 2332-2343 (2007).

39. Pasini, D. et al. Characterization of an antagonistic switch between histone H3 lysine 27 methylation and acetylation in the transcriptional regulation of Polycomb group target genes. *Nucleic Acids Res* (2010). doi:10.1093/nar/gkq244

40. Giordano, A. & Avantaggiati, M. p300 and CBP: partners for life and death. *J Cell Physiol* 181, 218-230 (1999).

41. Han, A., He, J., Wu, Y., Liu, J. O. & Chen, L. Mechanism of recruitment of class II histone deacetylases by myocyte enhancer factor-2. *J Mol Biol* 345, 91-102 (2005).

42. Youn, H. & Liu, J. Cabin1 represses MEF2-dependent Nur77 expression and T cell apoptosis by controlling association of histone deacetylases and acetylases with MEF2. *Immunity* 13, 85-94 (2000).

43. Yap, D. B. et al. Somatic mutations at EZH2 Y641 act dominantly through a mechanism of selectively altered PRC2 catalytic activity, to increase H3K27 trimethylation. *Blood* 117, 2451-2459 (2011).

44. Sneeringer, C. J. et al. Coordinated activities of wild-type plus mutant EZH2 drive tumor-associated hypertrimethylation of lysine 27 on histone H3 (H3K27) in human B-cell lymphomas. *Proc Natl Acad Sci USA* 107, 20980-20985 (2010).

45. Li, H. & Durbin, R. Fast and accurate short read alignment with Burrows-Wheeler transform. *Bioinformatics* 25, 1754-1760 (2009).

46. Goya, R. et al. SNVMix: predicting single nucleotide variants from next-generation sequencing of tumors. *Bioinformatics* 26, 730-736 (2010).

47. Robertson, G. et al. De novo assembly and analysis of RNA-seq data. *Nat Meth* 7, 909-912 (2010).

48. Mortazavi, A., Williams, B. A., Mccue, K., Schaeffer, L. & Wold, B. Mapping and quantifying mammalian transcriptomes by RNA-Seq. *Nat Meth* 5, 621-628 (2008).

49. Wright, G. et al. A gene expression-based method to diagnose clinically distinct subgroups of diffuse large B cell lymphoma. *Proc Natl Acad Sci USA* 100, 9991-9996 (2003).

50. He, J. et al. Structure of p300 bound to MEF2 on DNA reveals a mechanism of enhanceosome assembly. *Nucleic Acids Res* (2011). doi:10.1093/nar/gkr030

51. Beckwith, M., Longo, D. L., O'Connell, C. D., Moratz, C. M. & Urba, W. J. Phorbol ester-induced, cell-cycle-specific, growth inhibition of human B-lymphoma cell lines. *J. Natl. Cancer Inst.* 82, 501-509 (1990).

52. Kluin-Nelemans, H. C., Limpens, J., Meerabux, J., Beverstock, G. C., Jansen, J. H., et al. A new non-Hodgkin's B-cell line (DoHH2) with a chromosomal translocation t(14;18)(q32;q21). *Leukemia* 5, 221-224 (1991).

53. Dyer, M. J., Fischer, P., Nacheva, E., Labastide, W. & Karpas, A. A new human B-cell non-Hodgkin's lymphoma cell line (Karpas 422) exhibiting both t (14;18) and t(4;11) chromosomal translocations. *Blood* 75, 709-714 (1990).

54. Winter, J. N., Variakojis, D. & Epstein, A. L. Phenotypic analysis of established diffuse histiocytic lymphoma cell lines utilizing monoclonal antibodies and cytochemical techniques. *Blood* 63, 140-146 (1984).

55. Epstein, A., Variakojis, D., Berger, C. & Hecht, B. Use of novel chemical supplements in the establishment of three human malignant lymphoma cell lines (NU-DHL-1, NUDUL-1, and NU-AMB-1) with chromosome 14 translocations. International Journal of *Cancer* 35, 619-627 (1985).

56. Al-Katib, A. M., Smith, M. R., Kamanda, W. S., Pettit, G. R., Hamdan, M., et al. Bryostatin 1 down-regulates mdr1 and potentiates vincristine cytotoxicity in diffuse large cell lymphoma xenografts. *Clin Cancer Res* 4, 1305-1314 (1998).

57. Mehra, S., Messner, H., Minden, M. & Chaganti, R. S. K. Molecular cytogenetic characterization of non-Hodgkin lymphoma cell lines. Genes Chromosom. *Cancer* 33, 225-234 (2002).

58. Levy, S., Sutton, G., Ng, P., Feuk, L., Halpern, A., et al. The diploid genome sequence of an individual human. *PLoS Biol* 5, e254-e254 (2007).

59. Wheeler, D. A., Srinivasan, M., Egholm, M., Shen, Y., Chen, L., et al. The complete genome of an individual by massively parallel DNA sequencing. *Nature* 452, 872-876 (2008).

60. Wang, J., Wang, W., Li, R., Li, Y., Tian, G., et al. The diploid genome sequence of an Asian individual. *Nature* 456, 60-65 (2008).

61. Bentley, D. R., Balasubramanian, S., Swerdlow, H. P., Smith, G. P., Milton, J., et al. Accurate whole human genome sequencing using reversible terminator chemistry. *Nature* 456, 53-59 (2008).
62. Robinson, J. T., Thorvaldsdóttir, H., Winckler, W., Guttman, M., Lander, E. S., et al. Integrative genomics viewer. *Nat Biotechnol* 29, 24-26 (2011).
63. Robinson, M. D. & Oshlack, A. A scaling normalization method for differential expression analysis of RNA-seq data. 1-9 (2010).
64. Staden, R. The Staden sequence analysis package. *Mol. Biotechnol.* 5, 233-241 (1996).
65. Pasqualucci, L., Guglielmino, R., Malek, S. N., Novak, U., Compagno, M., et al. Aberrant Somatic Hypermutation Targets an Extensive Set of Genes in Diffuse Large B-Cell Lymphoma. *ASH Annual Meeting Abstracts* 104, 1528-1528 (2004).
66. Pasqualucci, L., Neumeister, P., Goossens, T., Nanjangud, G., Chaganti, R., et al. Hypermutation of multiple proto-oncogenes in B-cell diffuse large-cell lymphomas. *Nature* 412, 341-346 (2001).
67. Pasqualucci, L., Migliazza, A., Basso, K., Houldsworth, J., Chaganti, R. S. K., et al. Mutations of the BCL6 proto-oncogene disrupt its negative autoregulation in diffuse large B-cell lymphoma. *Blood* 101, 2914-2923 (2003).
68. Jones, S. J., Laskin, J., Li, Y. Y., Griffith, O. L., An, J., et al. Evolution of an adenocarcinoma in response to selection by targeted kinase inhibitors. *Genome Biol* 11, R82-R82 (2010).
69. Krzywinski, M., Schein, J., Birol, I., Connors, J., Gascoyne, R., et al. Circos: an information aesthetic for comparative genomics. *Genome Res* 19, 1639-1645 (2009).
70. Birol, I., Jackman, S., Nielsen, C., Qian, J., Varhol, R., et al. De novo Transcriptome Assembly with ABySS. *Bioinformatics* (2009). doi:btp367 [pii]10.1093/bioinformatics/btp367
71. Robertson, G., Hirst, M., Bainbridge, M., Bilenky, M., Zhao, Y., et al. Genome-wide profiles of STAT1 DNA association using chromatin immunoprecipitation and massively parallel sequencing. *Nat Meth* 4, 651-657 (2007).
72. Wiegand, K. C., Shah, S. P., Al-Agha, O. M., Zhao, Y., Tse, K., et al. ARID1A mutations in endometriosis-associated ovarian carcinomas. *N Engl J Med* 363, 1532-1543 (2010).
73. Gnirke, A., Melnikov, A., Maguire, J., Rogov, P., LePRoust, E., et al. Solution hybrid selection with ultra-long oligonucleotides for massively parallel targeted sequencing. *Nat Biotechnol* 27, 182-189 (2009).
74. Chin, S., Daigo, Y., Huang, H., Iyer, N. G., Callagy, G., et al. A simple and reliable pretreatment protocol facilitates fluorescent in situ hybridisation on tissue microarrays of paraffin wax embedded tumour samples. *MP, Mol. Pathol.* 56, 275-279 (2003).
75. Liu, X. et al. The structural basis of protein acetylation by the p300/CBP transcriptional coactivator. *Nature* 451, 846-850 (2008).
76. Lewis, B. P., Green, R. E. & Brenner, S. E. Evidence for the widespread coupling of alternative splicing and nonsense-mediated mRNA decay in humans. *Proc Natl Acad Sci USA* 100, 189-192 (2003).
77. Diehl, S. et al. STAT3-mediated up-regulation of BLIMP1 Is coordinated with BCL6 down-regulation to control human plasma cell differentiation. *J Immunol* 180, 4805-4815 (2008).
78. Ariel, O., Levi, Y. & Hollander, N. Signal transduction by CD58: The transmembrane isoform transmits signals outside lipid rafts independently of the GPI-anchored isoform. *Cell Signal* 21, 1100-1108 (2009).
79. Wilker, P. et al. Transcription factor Mef2c is required for B cell proliferation and survival after antigen receptor stimulation. *Nat Immunol* 9, 603-612 (2008).
80. Youn, H., Sun, L., Prywes, R. & Liu, J. Apoptosis of T cells mediated by Ca2+-induced release of the transcription factor MEF2. *Science* 286, 790-793 (1999).
81. Han, A. et al. Sequence-specific recruitment of transcriptional co-repressor Cabin1 by myocyte enhancer factor-2. *Nature* 422, 730-734 (2003).
82. Hunt, K. E., Hall, B. & Reichard, K. K. Translocations involving MUM1 are rare in diffuse large B-cell lymphoma. *Appl Immunohistochem Mol Morphol* 18, 109-112 (2010).
83. Linehan, L. A., Warren, W. D., Thompson, P. A., Grusby, M. J. & Berton, M. T. STAT6 is required for IL-4-induced germline Ig gene transcription and switch recombination. *J Immunol* 161, 302-310 (1998).
84. Saeki, K., Miura, Y., Aki, D., Kurosaki, T. & Yoshimura, A. The B cell-specific major raft protein, Raftlin, is necessary for the integrity of lipid raft and BCR signal transduction. *EMBO J* 22, 3015-3026 (2003).
85. Peled, J. U. et al. Requirement for cyclin D3 in germinal center formation and function. *Cell Res* 20, 631-646 (2010).
86. Srinivasan, L. et al. PI3 kinase signals BCR-dependent mature B cell survival. *Cell* 139, 573-586 (2009).
87. Cortes, M. & Georgopoulos, K. Aiolos is required for the generation of high affinity bone marrow plasma cells responsible for long-term immunity. *J Exp Med* 199, 209-219 (2004).
88. Shaffer, A. L. et al. Blimp-1 orchestrates plasma cell differentiation by extinguishing the mature B cell gene expression program. *Immunity* 17, 51-62 (2002).
89. Minegishi, Y. et al. Dominant-negative mutations in the DNA-binding domain of STAT3 cause hyper-IgE syndrome. *Nature* 448, 1058-1062 (2007).
90. Mullighan, C. G. et al. CREBBP mutations in relapsed acute lymphoblastic leukaemia. *Nature* 471, 235-239 (2011).
91. Janknecht, R. The versatile functions of the transcriptional coactivators p300 and CBP and their roles in disease. *Histol. Histopathol* 17, 657-668 (2002).
92. Potthoff, M. & Olson, E. MEF2: a central regulator of diverse developmental programs. *Development* 134, 4131-4140 (2007).
93. Youn, H. D., Chatila, T. A. & Liu, J. O. Integration of calcineurin and MEF2 signals by the coactivator p300 during T-cell apoptosis. *EMBO J* 19, 4323-4331 (2000).
94. Wu, W. et al. Conservation and evolution in and among SRF- and MEF2-type MADS domains and their binding sites. *Molecular biology and evolution* (2010). doi: 10.1093/molbev/msq214
95. Martin, J. et al. A Mef2 gene that generates a muscle-specific isoform via alternative mRNA splicing. *Mol Cell Biol* 14, 1647-1656 (1994).
96. Molkentin, J. D., Black, B. L., Martin, J. F. & Olson, E. N. Mutational analysis of the DNA binding, dimerization, and transcriptional activation domains of MEF2 C. *Mol Cell Biol* 16, 2627-2636 (1996).
97. van der Heide, L. P. & Smidt, M. P. Regulation of FoxO activity by CBP/p300-mediated acetylation. *Trends Biochem. Sci.* 30, 81-86 (2005).

98. Dequiedt, F. et al. HDAC7, a thymus-specific class II histone deacetylase, regulates Nur77 transcription and TCR-mediated apoptosis. *Immunity* 18, 687-698 (2003).
99. Eylenstein, A. et al. Stimulation of Ca2+-channel Orai1/STIM1 by serum- and glucocorticoid-inducible kinase 1 (SGK1). *FASEB J* 25, 2012-2021 (2011).
100. Dunleavy, K. et al. Differential efficacy of bortezomib plus chemotherapy within molecular subtypes of diffuse large B-cell lymphoma. *Blood* 113, 6069-76 (2009).
101. Hernandez-llizaliturri, F. J. et al. Higher response to lenalidomide in relapsed/refractory diffuse large B-cell lymphoma in nongerminal center b-cell-like than in germinal center B-cell-like phenotype. *Cancer* (2011)

The invention claimed is:

1. A method of treating B-cell non-Hodgkin lymphoma (NHL) comprising administering to a human subject identified as having B-cell NHL a B-cell NHL treatment, wherein the subject is identified as having B-cell NHL by testing a sample from the subject for a mutation in Enhancer of Zeste Homolog 2 (EZH2), wherein the presence of the mutation identifies the subject as having B-cell NHL, wherein the mutation in EZH2 is a non-synonymous substitution of Alanine (A) at position 682 (A682) of a wild-type EZH2 protein sequence and/or a non-synonymous substitution of Alanine (A) at position 692 (A692) of a wild-type EZH2 protein sequence.

2. The method of claim 1, wherein testing the sample comprises detecting one or more mutations in a nucleic acid coding for EZH2.

3. The method of claim 2, wherein detecting one or more mutations in a nucleic acid coding for EZH2 comprises PCR, primer extension, a microarray assay, sequencing, line probes or any combination thereof.

4. The method of claim 1, wherein the sample is a blood sample, a plasma sample or a tumor sample from a subject suspected of having B-cell non-Hodgkin lymphoma.

5. The method of claim 1, wherein the sample is a blood sample, a tumor sample or a plasma sample.

6. The method of claim 1, wherein the mutation in EZH2 is a non-synonymous substitution of Alanine (A) at position 692 (A692) of a wild-type EZH2 protein sequence, wherein the substitution mutation in EZH2 is A692V.

7. The method of claim 6, wherein the mutation in EZH2 further comprises a non-synonymous substitution of Alanine (A) at position 682 (A682) of the wild-type EZH2 protein sequence, wherein the substitution mutation is A682G.

8. The method of claim 1, wherein the mutation in EZH2 is a non-synonymous substitution of Alanine (A) at position 682 (A682) of a wild-type EZH2 protein sequence, wherein the substitution mutation in EZH2 is A682G.

9. The method of claim 8, wherein the mutation in EZH2 further comprises a non-synonymous substitution of Alanine (A) at position 692 (A692) of the wild-type EZH2 protein sequence, wherein the substitution mutation is A692V.

10. The method of claim 1, wherein testing the sample comprises detecting one or more mutations in an EZH2 polypeptide.

11. The method of claim 10, wherein detecting one or more mutations in an EZH2 polypeptide comprises mass spectrometry, multiple reaction monitoring (MRM) mass spectrometry, product-ion monitoring (PIM) mass spectrometry, an immunoassay, a Western Blot assay, an ELISA assay, immunoprecipitation followed by sodium-dodecyl sulfate polyacrylamide gel electrophoresis (SDS-PAGE) immunocytochemistry, protein sequencing or any combination thereof.

12. The method of claim 1, wherein the substitution mutation is a somatic mutation.

* * * * *